United States Patent
Seiki et al.

(10) Patent No.: US 6,780,412 B2
(45) Date of Patent: Aug. 24, 2004

(54) PROTEIN AND MONOCLONAL ANTIBODY SPECIFIC THERETO

(75) Inventors: Motoharu Seiki, Shinagawa (JP); Hiroshi Sato, Kanazawa (JP); Akira Shinagawa, Takaoka (JP)

(73) Assignee: Fuji Yakuhin Kogyo Kabushiki Kaisha, Toyama (JP)

( * ) Notice: Subject to any disclaimer, the term of this patent is extended or adjusted under 35 U.S.C. 154(b) by 165 days.

(21) Appl. No.: 09/734,002

(22) Filed: Dec. 12, 2000

(65) Prior Publication Data

US 2001/0016333 A1 Aug. 23, 2001

Related U.S. Application Data

(62) Division of application No. 09/000,041, filed as application No. PCT/JP96/01956 on Jul. 12, 1996, now Pat. No. 6,191,255.

(30) Foreign Application Priority Data

Jul. 14, 1995 (JP) ............................................. 7-200319
Jul. 14, 1995 (JP) ............................................. 7-200320

(51) Int. Cl.[7] ...................... A61K 39/395; C07K 16/00; C07K 16/40; G01N 33/53; C12P 21/04
(52) U.S. Cl. .................. 424/130.1; 435/7.1; 435/70.21; 530/387.9; 530/388.1; 530/389.1
(58) Field of Search ........................... 530/387.1, 387.7, 530/387.9, 388.1, 388.26, 388.8, 388.85, 389.1; 424/138.1, 139.1, 141.1, 146.1

(56) References Cited

PUBLICATIONS

Takino et al (Journal of Biological chemistry, Sep. 1995, vol. 270, pp. 23013–23020.*
Paul (Fundamental Immunology, (text), 1993, p. 460).*
Thrope and Rafferty (Preparation and Use of Radio labeled Antibodies and antigens, In: Immunochemistry LabFax, 1994, Kerr and Thrope Ed.s, pp. 115–126).*
Young et al. Fibrinolysis 8/Suppl. 1:p56, 1994.*
Serafini et al. The Journal of Nuclear Medicine, 34/3:533–536.*

A. Strongin et al., "Mechanism of cell surface activation of 72–kDa type IV collagenase" The Journal of Biological Chemistry, vol. 270, No. 10, pp. 5331–5338, Mar. 10, 1995.
H. Sato et al. "A matrix metalloproteinase expressed on the surface of invasive tumour cells", Nature, vol. 370, pp 61–65, Jul. 7, 1994.
H. Azzam, et al., "Association of MMP–2 Activation Potential With Metastatic Progression in Human Breast Cancer Cell Lines Independent of MMP–2 Production," Journal of the National Cancer Institute, vol, 85, No. 21, Nov. 3, 1993, pp. 1758–1764.
P.D. Brown, et al., "Expression of activated gelatinase in human invasive breast carcinoma," Clinical & Experimental Metastasis, vol. 11, No. 2, 1993, pp. 183–189.
A. Strongin, et al., "Plasma Membrane–dependent Activation of the 72–kDa Type IV Collagenase Is Prevented by Complex Formation with TIMP–2*," The Journal of Biological Chemistry, vol. 268, No. 19, Jul. 5, 1993, pp. 14033–14039.
T. Takino, et al., "Identification of the Second Membrane–type Matrix Metalloproteinase (MT–MMP–2) Gene from a Human Placenta cDNA Library," The Journal of Biological Chemistry, vol. 270, No. 39, Sep. 29, 1995, pp. 23013–23020.

* cited by examiner

Primary Examiner—Karen A. Canella
(74) Attorney, Agent, or Firm—Wenderoth, Lind & Ponack, L.L.P.

(57) ABSTRACT

A novel protein which is useful as diagnostic means for the studies relating to the diagnosis and treatment of cancer (detection of cancer cells, estimation of the malignity, etc.) and in other medicinal and physiological purposes; a gene encoding the same; and an antibody, in particular, a monoclonal antibody specific to the protein. MT-MMP-3, which is a pro MMP-2 activator having the ability to activate pro MMP-2 which is under expression specifically on the surface layer of a human cancer cell and falling within the category of MMP but being different from MT-MMP-1; a DNA containing the base sequence encoding the same; host cells transformed by the DNA; a process for producing a matrix metalloproteinase protein by using the host cells; a monoclonal antibody binding specifically to the matrix metalloproteinase protein; and use of the protein and antibody.

14 Claims, 14 Drawing Sheets

FIG. 1A-1

Signal peptide

```
MMP-1       MHSFPPLLLLLFWG----------------------VVSHSFP------ATLETQ
MMP-2       MEALMRGALTGPLRALCLLGCLLSHAAA------AP------SPIIKFPG
MMP-3       MKSLPILLLLCVAV--------------------------CSAYP-----LDGAARGE
MMP-7       MR--LTVLCAVCLL--------------------------PGSLALP--------LPQE
MMP-8       MFSLKTLPFLLLLH--------------------------VQISKAFP-------VSSK
MMP-9       MSLWQPLVLVLVLGCC------------------FAAPRQRQSTLVLFPG
MMP-10      MMHLAFLVLLCLPV--------------------------CSAYP-----LSGAAKEE
MMP-11      MAPAAWLRSAAARALLPPMLLLLQPPLLARALP-----------------
MMP-12      MKFLLILLQ-ATA-------------------------SGALP-----LNSSTSLE
MT-MMP-1    MSPAPRPSRCLLLPLLTLGTALASLGSAQSSSFSP---------------
MT-MMP-3    MILLTFSTGRRLDFVH----------------HSGVFFLQTLLWILCATVCG
Consensus   M..L..L.......................A.P................
```

Pro-peptide

```
MMP-1       DAETLKVMKQPRCGVPDVAQ-------------FVLTEGNPRWEQTHLT
MMP-2       DQNTIETMRKPRCGNPDVAN-------------YNFFPRKPKWDKNQIT
MMP-3       DSDTLEVMRKPRCGVPDVGH-------------FRTFPGIPKWRKTHLT
MMP-7       NSRVIEIMQKPRCGVPDVAE-------------YSLFPNSPKWTSKVVT
MMP-8       NEETLDMMKKPRCGVPDSGG-------------FMLTPGNPKWERTNLT
MMP-9       DSATLKAMRTPRCGVPDLGR-------------FQTFEGDLKWHHHNIT
MMP-10      DTDTLEVMRKPRCGVPDVGH-------------FSSFPGMPKWRKTHLT
MMP-11      APRPASSLRPPRCGVPDPSD-GLSARNRQKRFVLSGG--RWEKTDLT
MMP-12      DTSTLEMMHAPRCGVPDLHH-------------FREMPGGPVWRKHYIT
MT-MMP-1    DADTMKAMRRPRCGVPDKFGAEIKANVRRKRYAIQ-G-LKWQHNEIT
MT-MMP-3    DRNTIDWMKKPRCGVPDQTRGSSKFHIRRKRYALTGQ--KWQHKHIT
Consensus   D..TL..MRKPRCGVPD........................F...PG.PKW......T
```

```
                Pro-peptide
EQDVDLVQKYLEKYYNLKNDGRQVEKRRNSGPVV-EKLKQMQEFFGLKVTGKP      79
DVAPK-TDKELAVQYLNTF-YGCPKE-SCNLFVLKDTLKKMQKFFGLPQTGDL      89
DTSMNLVQKYLENYYDLKKDVKQFVRRKDSGPVV-KKIREMQKFIGLEVTGKL      79
AGGMSELQWEQAQDY-LKRFYLYDSETKNANSLE-AKLKEMQKFFGLPITGML      74
EKNTKTVQDYLEKFYQLPSNQYQSTR-KNGTNVIVEKLKEMQRFFGLNVTGKP      78
DLRTNLTDRQLAEEYLYRGYTRVAEMRGESKSLGPALLLLQKQLSLPETGEL      86
DSNKDLAQQYLEKYYNLEKDVKQFRRK-DSNLIV-KKIQGMQKFLGLEVTGKL      78
----------PDVHHLHAERRGPQ-----------PWHAALPSSPAPAPATQE      67
KNNVLFGERYLEKFYGLEINKLPVTKMKYSGNLMKEKIQEMQHFLGLKVTGQL      79
-----EAWLQQYGYLPPGDLRTHTQRSPQSLS-AAIAAMQKFYGLQVTGKA       80
TEQYFNVEVHLQKYGYLPPTSPRMSVVRSAETMQ-SALAAMQQFYGINMTGKV      88
........L..Y.L......-......-........KL..MQKF.GL.VTGKL    100
                Catalytic
YRIENYTPDLPRADVDHAIEKAFQLWSNVTPLTFTKV-------SEGQADIM     160
YRIIGYTPDLDPETVDDAFARAFQVWSDVTPLRFSRI-------HDGEADIM     170
YRIVNYTPDLPKDAVDSAVEKALKVWEEVTPLTFSRL-------YEGEADIM     160
YRIVSYTRDLPHITVDRIVSKALNMWGKEIPLHFRKV-------VWGTADIM     155
YRIRNYTPQLSEAEVERAIKDAFELWSVASPLIFTRI-------SQGEADIN     159
YWIQNYSEDLPRAVIDDAFARAFALWSAVTPLTFTRV-------YSRDADIV     167
YRIVNYTPDLPRDAVDSAIEKALKVWEEVTPLTFSRL-------YEGEADIM     159
YRILRFPWQLVQEQVRQTMAEALKVWSDVTPLTFTEV-------HEGRADIM     156
YRINNYTPDMNREDVDYAIRKAFQVWSNVTPLKFSKI-------NTGMADIL     160
FCIQNYTPKVGEYATYEAIRKAFRVWESATPLRFREVPYAYIREGHEKQADIM    178
YSIKNVTPKVGDPETRKAIRRAFDVWQNVTPLTFEEVPYSELENGK-RDVDIP    185
YRI.NYTPDL...VD.AI.KAF.VWS.VTPLTF..V-------..G.ADIM     200
                                ↑IS-2
```

FIG. 1B-1

```
                                                                    Catalytic
MMP-1       ISFVRGDHRDNSPFDGPGGNLAHAFQPGPGIGGDAHFDEHERWTN-NFTEYN
MMP-2       INFGRWEHGDYPFDGKDGLLAHAFAPGTGVGGDSHFDDDELWTLGEGQVVR
MMP-3       ISFAVREHGDFYPFDGPGNVLAHAYAPGPGINGDAHFDDDEQWTK-DTTGTN
MMP-7       IGFARGAHGDSYPFDGPGNTLAHAFAPGTGLGGDAHFDEDERWTDGSSLGIN
MMP-8       IAFYQRDHGDNSPFDGPNGILAHAFQPGPGQGIGGDAHFDAEETWTN-TSANYN
MMP-9       IQFGVAEHGDYPFDGKDGLLAHAFPPGPGIQGDAHFDDDELWSLGKGVVVP
MMP-10      ISFAVKEHGDFYSFDGPGHSLAHAYPPGPGLYGDIHFDDDEKWTE-DASGTN
MMP-11      IDFARYWDGDDLPFDGPGGILAHAFFPKTHREGDVHFDYDETWTIGDDQGTD
MMP-12      VVFARGAHGDFHAFDGKKGGILAHAFGPGSGIGGDAHFDEDEFWTT-HSGGTN
MT-MMP-1    IFFAEGFHGDSTPFDGEGGFLAHAYFPGPNIGGDTHFDSAEPWTV-RNEDLN
MT-MMP-3    IIFASGFHGDSSPFDGEGGFLAHAYFPGPGIGGDTHFDSDEPWTLGNPNHDG
Consensus   I.FA...HGD..PFDGPGG.LAHAF.PGPGIGGDAHFD.DE.WT.....N Catalytic
MMP-1       ----------------------------------------------------
MMP-2       YGFCPHEALFTMGGNAEGQPCKFPFRFQGTSYDSCTTEGRTDGYRWCGTTED
MMP-3       ----------------------------------------------------
MMP-7       ----------------------------------------------------
MMP-8       ----------------------------------------------------
MMP-9       FGFCPSERLYTRDGNADGKPCQFPFIFQGQSYSACTTDGRSDGYRWCATTAN
MMP-10      ----------------------------------------------------
MMP-11      ----------------------------------------------------
MMP-12      ----------------------------------------------------
MT-MMP-1    ----------------------------------------------------
MT-MMP-3    ----------------------------------------------------
Consensus   ----------------------------------------------------
```

FIG. IB-2

```
VKYGNADGEYCKFPFLFNGKEYNSCTDTGRSDGFLWCSTTYNFEKDGK   211
                                                  270
                                                  211
                                                  207
                                                  210
TRFGNADGAACHFPFIFEGRSYSACTTDGRSDGLPWCSTTANYDTDDR   267
                                                  210
                                                  208
                                                  211
                                                  229
                                                  237
                                                  300

YDRDKKYGFCPETAMSTV-GGNSEGAPCVFPFTFLGNKYESCTSAGRS   211
                                                  369
                                                  211
                                                  207
                                                  210
YDRDKLFGFCPTRADSTVMGGNSAGELCVFPFTFLGKEYSTCTSEGRG   367
                                                  210
                                                  208
                                                  211
                                                  229
                                                  237
                                                  400
```

FIG. 1C-1

```
                                                            Catalytic
MMP-1       ------------------------------LHRVAA-HELGHSLGLSHST
MMP-2       DGKMWCATTANYDDDDRKWGFCPDQGYSLFLVAA-HEFGHAMGLEHSQ
MMP-3       ------------------------------LFLVAA-HEIGHSLGLFHSA
MMP-7       ------------------------FLYAATHELGHSLGMGHSS
MMP-8       ------------------------------LFLVAA-HEFGHSLGLAHSS
MMP-9       DGRLWCATTSNFDSDKKWGFCPDQGYSLFLVAA-HEFGHALGLDHSS
MMP-10      ------------------------------LFLVAA-HELGHSLGLFHSA
MMP-11      ------------------------------LLQVAA-HEFGHVLGLQHTT
MMP-12      ------------------------------LFLTAV-HEIGHSLGLGHSS
MT-MMP-1    ---------------------GNDIFLVAV-HELGHALGLEHSS
MT-MMP-3    ---------------------NDLFLVAV-HELGHALGLEHSN
Consensus   ------------------------------LFLVAA-HE.GHSLGL.HS.

Hinge
MMP-1       ---------------------------------RSQNP
MMP-2       -------------------------ASPDIDLGTG
MMP-3       ---------------PPPDSPETPLVPTE
MMP-7       ------------------------------
MMP-8       ---------------------------------LSSNP
MMP-9       APPTVCPTGPPTVHPSERPTAGPTGPPSAGPTGPPTAGPSTA-TTVP
MMP-10      -----------------------------PPPASTEEPLVPTK
MMP-11      -------------QPWPTVTSRTPALGPQAGIDTNE
MMP-12      ---------------------------------DPKENQRL
MT-MMP-1    ----------GESGFPTKMPPQPRTTSRPSVP
MT-MMP-3    -------SPDKIPPPTRPLPTVPPHRSIPPADPRKNDRPKPPRPPT
Consensus   ------------------------------.
```

FIG. ID-1

Hemopexin

```
MMP-1       FTSVFWPQLPNGLEAAYEFADRDEVRF FKGNKYWAV-QGQNVLHGYPKDIYSSFGFPR
MMP-2       LVATFWPELPEKIDAVYEAPQEEKAVFFAGNEYWIY-SASTLERGYPKPLTS-LGLPP
MMP-3       LISSFWPSLPSGVDAAYEVTSKDLVFIFKGNQFWAI-RGNEVRAGYPRGIHT-LGFPP
MMP-7       ————————————————————————————————————————————————————————
MMP-8       FISLFWPSLPTGIQAAYEDFDRDLIFLFKGNQYWAL-SGYDILQGYPKDISN-YGFPS
MMP-9       LIADKWPALPRKLDSVFEEPLSKKLFFFSGRQVWVYTGASVL--G-PRRLDK-LGLGA
MMP-10      LISAFWPSLPSYLDAAYEVNSRDTVFIFKGNEFWAI-RGNEVQAGYPRGIHT-LGFPP
MMP-11      LASRHWQGLPSPVDAAFE-DAQGHIWFFQGAQYWVY-DGEKPVLG-PAPLTE-LGLVR
MMP-12      LISSLWPTLPSGIEAAYEIEARNQVFLFKDDKYWLI-SNLRPEPNYPKSIHS-FGFPN
MT-MMP-1    PIGQFWRGLPASINTAYERKDGKFVF-FKGDKHWVF-DEASLEPGYPKHIKE-LGRGL
MT-MMP-3    QITYFWRGLPPSIDAVYENSDGNFVF-FKGNKYWVF-KDTTLQPGYPHDLIT-LGSGI
Consensus   LIS.FWP.LP....DAAYE......VF.FKGN.YW........GYP.I...-LG.P.
```

Hemopexin →

```
MMP-1       MIAHDFPGIGHKVDAVFMKDGFF--YFFHGTRQYKFDPKT-KRILTL-QKANS-WFNC
MMP-2       LIADAWNAIPDNLDAVVDLQGGGHSYFFKGAYYLKLENQS-LKSVKF-GSIKSDWLGC
MMP-3       QIAEDFPGIDSKIDAVFEEFGFF--YFFTGSSQLEFDPNA-KKVTHT-LKSNS-WLNC
MMP-7       ————————————————————————————————————————————————————————
MMP-8       SISGAFPGIESKVDAVFQQEHFF--HVFSGPRYYAFDLIA-QRVTRV-ARGNK-WLNC
MMP-9       EVDRMFPGVPLDTHDVFQYREKA--YFCQDRFYWRVSSRSELNQVDQVGYVTYDILQC
MMP-10      LIADDFPGVEPKVDAVLQAFGFF--YFFSGSSQFEFDPNA-RMVTHI-LKSNS-WLHC
MMP-11      R-ATDWRGVPSEIDAAFQDADGYA-YFLRGRLYWKFDPVK-VKALEGFPRLVGPDFFG
MMP-12      LITKNFQGIGPKIDAVFYSKNKY-YYFFQGSNQFEYDFLL-QRITKT-LKSNS-WFGC
MT-MMP-1    NIKVWE-GIPESPRGSFMGSDEVFTYFYKGNKYKFNNQKLKVEPGYPKSALRDWMGC
MT-MMP-3    PITVWK-GIPESPQGAFVHKENGFTYFYKEGVLEIQTTRYSRLEPGHPRSILKDLSGC
Consensus   .I...F.GI....DAVF......YFF.G......FD........-W..C
```

FIG. 1D-2

```
TVKHIDAA-LSEENTGKTYFFVANKYWRYDEYKRSMDPGYPK      413
DVQRVDAA-FNWSKNKKTYIFAGDKFWRYNEVKKKMDPGFPK      604
TVRKIDAA-ISDKEKNKTYFFVEDKYWRFDEKRNSMEPGFPK      424
------------------------------------------      267
SVQAIDAA-VFYRS--KTYFFVNDQFWRYDNQRQFMEPGYPK      411
DVAQVIGA-LRSGR-GKMLLFSGRRLWRFDVKAQMVDPRSAS      648
TIRKIDAA-VSDKEKKKTYFFAADKYWRFDENSQSMEQGFPR      423
FP--VHAALVWGPEKNKIYFFRGRDYWRFHPSTRRVDSPVPR      424
FVKKIDAA-VFNPRFYRTYFFVDNQYWRYDERRQMMDPGYPK      416
PTDKIDAA-LFWMPNGKTYFFRGNKYYRFNEELRAVDSEYPK      451
PPHGIDSA-IWWEDVGKTYFFKGDRYWRYSEEMKTMDPGYPK      472
.V..IDAA-.....KIYFF....YWR.DE....MDPG.PK        700

RKN---------------------------------------      469
------------------------------------------      660
------------------------------------------      477
------------------------------------------      267
RYG---------------------------------------      467
PED---------------------------------------      707
------------------------------------------      476
CAEPANTFL---------------------------------      488
------------------------------------------      470
PSGGRPDEGTEEETE-VIIIEVDEEGGAVSAAAVVLPVLLL       549
DGPTDRVKEGHSPPDDVDIVIKLDNTASTVKAIAIVIPCILA     571
                            ←IS-3              800
```

FIG. IE

| | | |
|---|---|---|
| MMP-1 | ------------------- | 469 |
| MMP-2 | ------------------- | 660 |
| MMP-3 | ------------------- | 477 |
| MMP-7 | ------------------- | 267 |
| MMP-8 | ------------------- | 468 |
| MMP-9 | ------------------- | 708 |
| MMP-10 | ------------------- | 476 |
| MMP-11 | ------------------- | 489 |
| MMP-12 | ------------------- | 470 |
| MT-MMP-1 | LLVLAVGLAVFFFRRHGTPRRLLYCQRSLLDKV | 582 |
| MT-MMP-3 | LCLLVLVYTVFQFKRKGTPRHILYCKRSMQEWV | 604 |
| Consensus | ------------------- | 833 |

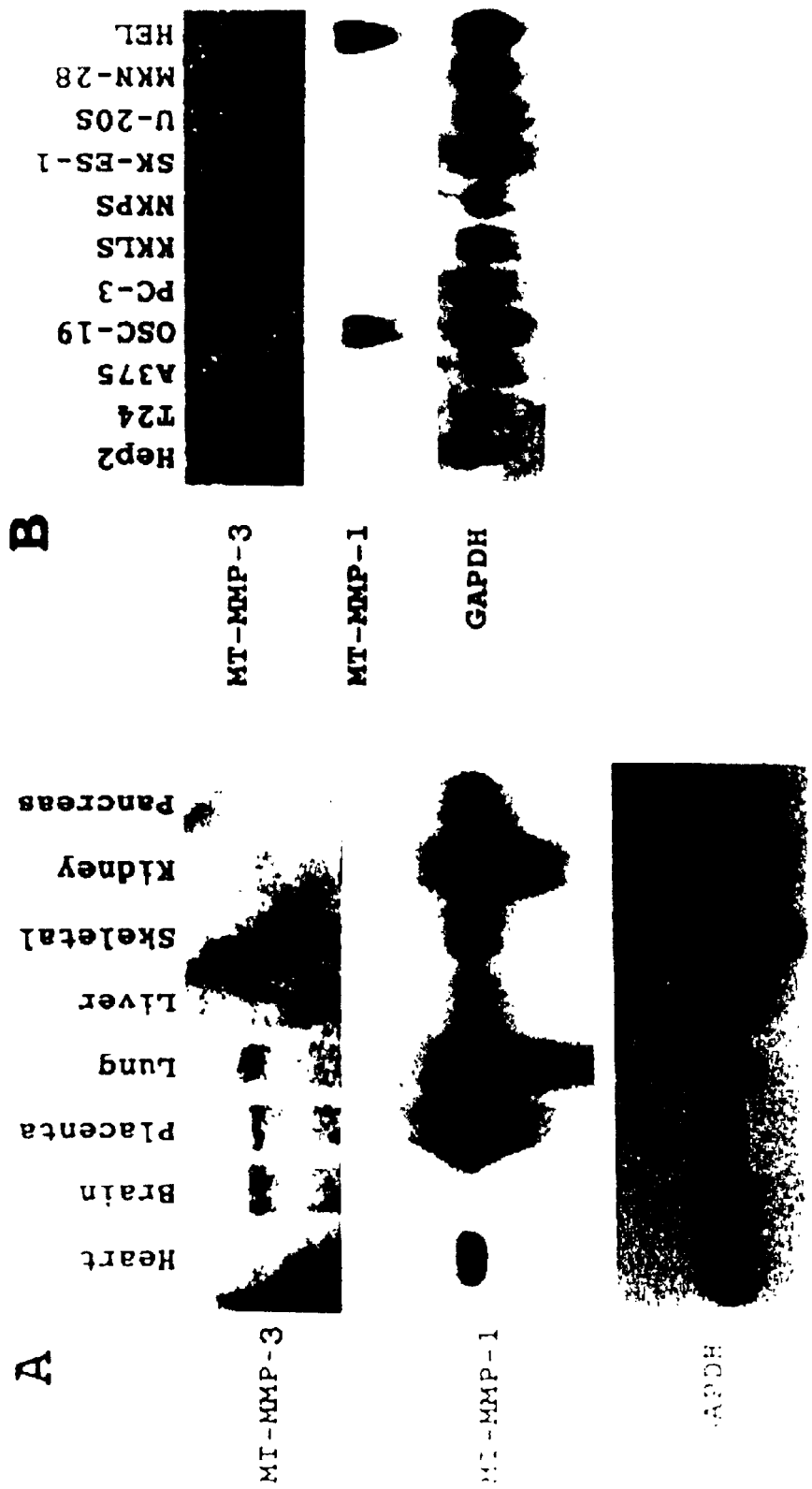

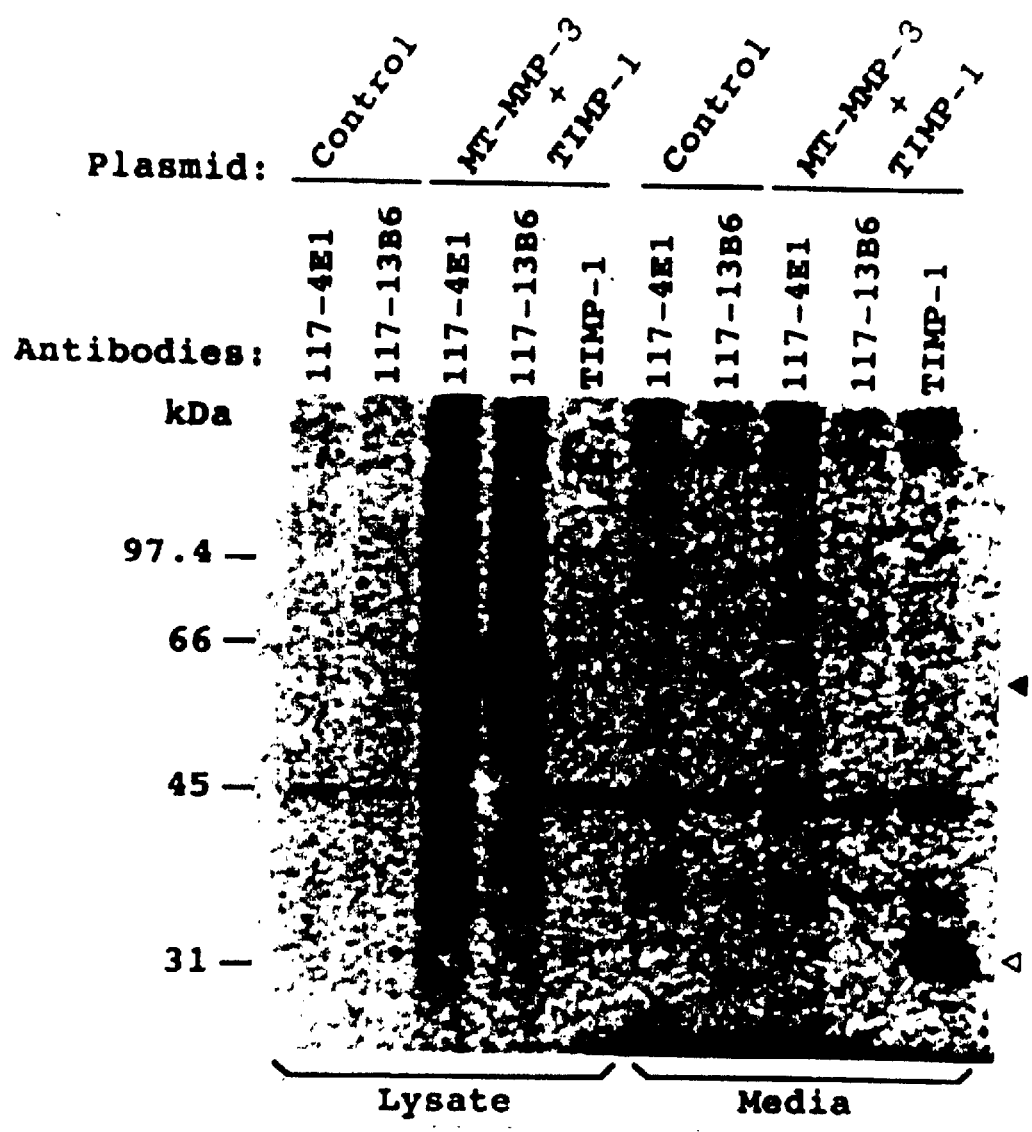

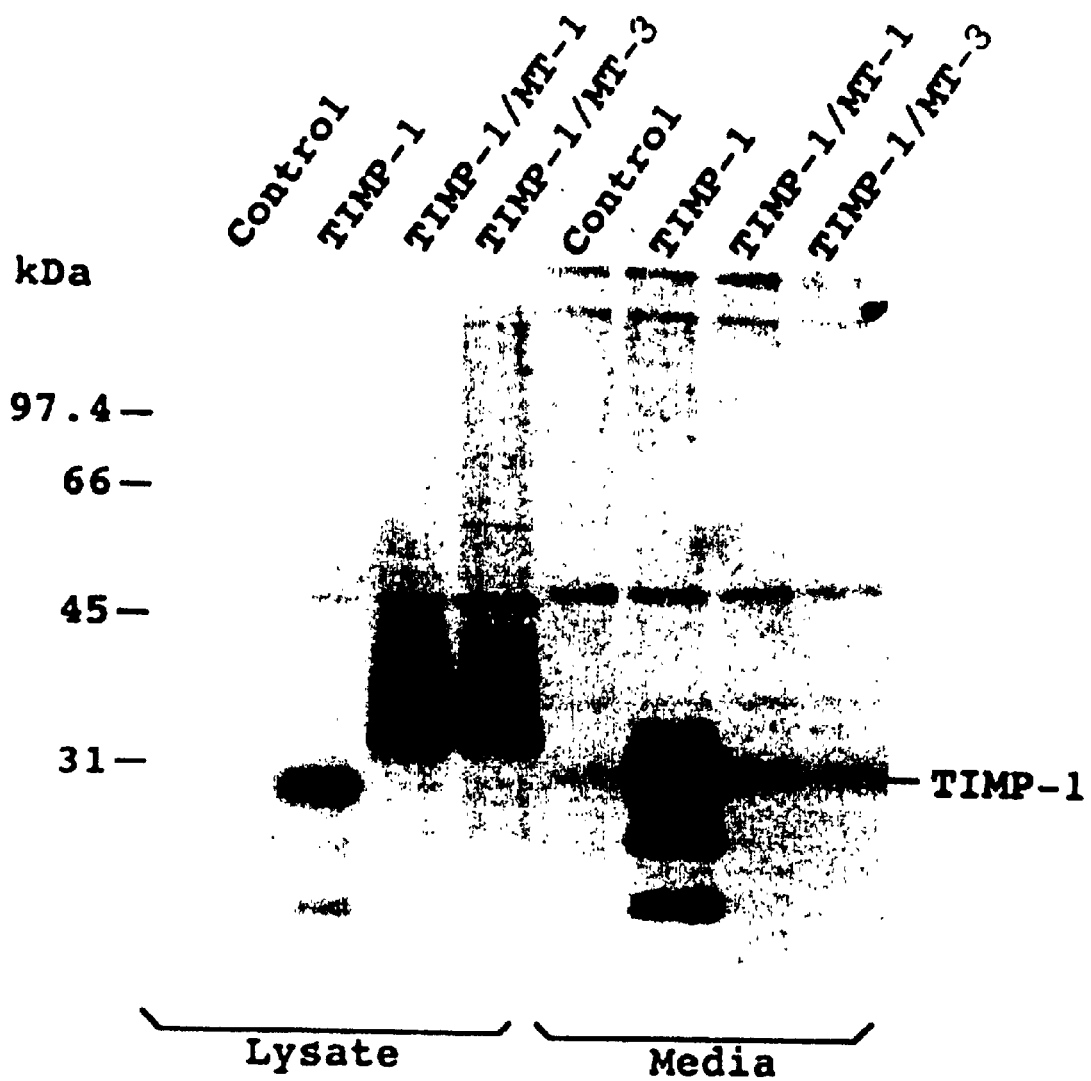

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 2116

(B) TYPE: Nucleic acid
(C) STRANDEDNESS: Double
(D) TOPOLOGY: Linear (ii) MOLECULE TYPE: cDNA (vi) ORIGINAL SOURCE:
    (A) ORGANISM: Human (xi) SEQUENCE DESCRIPTION: SEQ ID NO: 1:

```
GGCTCCTTAC CCACCCGGAG ACTTTTTTTT GAAAGGAAAC TAGGGAGGGAGGGAGAGGGA        60

GAGAGGGAGA AAACGAAGGG GAGCTCGTCC ATCCATTGAA GCACAGTTCA CT ATG          115
                                                          Met
                                                           1

ATC TTA CTC ACA TTC AGC ACT GGA AGA CGG TTG GAT TTC GTG CAT CAT        163
Ile Leu Leu Thr Phe Ser Thr Gly Arg Arg Leu Asp Phe Val His His
            5                  10                  15

TCG GGG GTG TTT TTC TTG CAA ACC TTG CTT TGG ATT TTA TGT GCT ACA        211
Ser Gly Val Phe Phe Leu Gln Thr Leu Leu Trp Ile Leu Cys Ala Thr
         20                  25                  30

GTC TGC GGA ACG GAG CAG TAT TTC AAT GTG GAG GTT TGG TTA CAA AAG        259
Val Cys Gly Thr Glu Gln Tyr Phe Asn Val Glu Val Trp Leu Gln Lys
 35                  40                  45

TAC GGC TAC CTT CCA CCG ACT GAC CCC AGA ATG TCA GTG CTG CGC TCT        307
Tyr Gly Tyr Leu Pro Pro Thr Asp Pro Arg Met Ser Val Leu Arg Ser
 50                  55                  60                  65

GCA GAG ACC ATG CAG TCT GCC CTA GCT GCC ATG CAG CAG TTC TAT GGC        355
Ala Glu Thr Met Gln Ser Ala Leu Ala Ala Met Gln Gln Phe Tyr Gly
             70                  75                  80

ATT AAC ATG ACA GGA AAA GTG GAC AGA AAC ACA ATT GAC TGG ATG AAG        403
Ile Asn Met Thr Gly Lys Val Asp Arg Asn Thr Ile Asp Trp Met Lys
             85                  90                  95

AAG CCC CGA TGC GGT GTA CCT GAC CAG ACA AGA GGT AGC TCC AAA TTT        451
Lys Pro Arg Cys Gly Val Pro Asp Gln Thr Arg Gly Ser Ser Lys Phe
            100                 105                 110

CAT ATT CGT CGA AAG CGA TAT GCA TTG ACA GGA CAG AAA TGG CAG CAC        499
His Ile Arg Arg Lys Arg Tyr Ala Leu Thr Gly Gln Lys Trp Gln His
        115                 120                 125

AAG CAC ATC ACT TAC AGT ATA AAG AAC GTA ACT CCA AAA GTA GGA GAC        547
Lys His Ile Thr Tyr Ser Ile Lys Asn Val Thr Pro Lys Val Gly Asp
130                 135                 140                 145

CCT GAG ACT CGT AAA GCT ATT CGC CGT GCC TTT GAT GTG TGG CAG AAT        595
Pro Glu Thr Arg Lys Ala Ile Arg Arg Ala Phe Asp Val Trp Gln Asn
                150                 155                 160

GTA ACT CCT CTG ACA TTT GAA GAA GTT CCC TAC AGT GAA TTA GAA AAT        643
Val Thr Pro Leu Thr Phe Glu Glu Val Pro Tyr Ser Glu Leu Glu Asn
                165                 170                 175

GGC AAA CGT GAT GTG GAT ATA ACC ATT ATT TTT GCA TCT GGT TTC CAT        691
Gly Lys Arg Asp Val Asp Ile Thr Ile Ile Phe Ala Ser Gly Phe His
            180                 185                 190

GGG GAC AGC TCT CCC TTT GAT GGA GAG GGA GGA TTT TTG GCA CAT GCC        739
Gly Asp Ser Ser Pro Phe Asp Gly Glu Gly Gly Phe Leu Ala His Ala
        195                 200                 205

TAC TTC CCT GGA CCA GGA ATT GGA GGA GAT ACC CAT TTT GAC TCA GAT        787
Tyr Phe Pro Gly Pro Gly Ile Gly Gly Asp Thr His Phe Asp Ser Asp
210                 215                 220                 225

GAG CCA TGG ACA CTA GGA AAT CCT AAT CAT GAT GGA AAT GAC TTA TTT        835
Glu Pro Trp Thr Leu Gly Asn Pro Asn His Asp Gly Asn Asp Leu Phe
                230                 235                 240

CTT GTA GCA GTC CAT GAA CTG GGA CAT GCT CTG GGA TTG GAG CAT TCC        883
Leu Val Ala Val His Glu Leu Gly His Ala Leu Gly Leu Glu His Ser
```

-continued

|     |     |     |     |     |     |     |     |     |     |     |     |     |     |     |     |
|---|---|---|---|---|---|---|---|---|---|---|---|---|---|---|---|
|  |  | 245 |  |  |  |  | 250 |  |  |  |  | 255 |  |  |  |

```
AAT GAC CCC ACT GCC ATC ATG GCT CCA TTT TAC CAG TAC ATG GAA ACA      931
Asn Asp Pro Thr Ala Ile Met Ala Pro Phe Tyr Gln Tyr Met Glu Thr
        260             265             270

GAC AAC TTC AAA CTA CCT AAT GAT GAT TTA CAG GGC ATC CAG AAA ATA      979
Asp Asn Phe Lys Leu Pro Asn Asp Asp Leu Gln Gly Ile Gln Lys Ile
        275             280             285

TAT GGT CCA CCT GAC AAG ATT CCT CCA CCT ACA AGA CCT CTA CCG ACA     1027
Tyr Gly Pro Pro Asp Lys Ile Pro Pro Pro Thr Arg Pro Leu Pro Thr
290             295             300             305

GTG CCC CCA CAC CGC TCT ATT CCT CCG GCT GAC CCA AGG AAA AAT GAC     1075
Val Pro Pro His Arg Ser Ile Pro Pro Ala Asp Pro Arg Lys Asn Asp
                310             315             320

AGG CCA AAA CCT CCT CGG CCT CCA ACC GGC AGA CCC TCC TAT CCC GGA     1123
Arg Pro Lys Pro Pro Arg Pro Pro Thr Gly Arg Pro Ser Tyr Pro Gly
        325             330             335

GCC AAA CCC AAC ATC TGT GAT GGG AAC TTT AAC ACT CTA GCT ATT CTT     1171
Ala Lys Pro Asn Ile Cys Asp Gly Asn Phe Asn Thr Leu Ala Ile Leu
        340             345             350

CGT CGT GAG ATG TTT GTT TTC AAG GAC CAG TGG TTT TGG CGA GTG AGA     1219
Arg Arg Glu Met Phe Val Phe Lys Asp Gln Trp Phe Trp Arg Val Arg
        355             360             365

AAC AAC AGG GTG ATG GAT GGA TAC CCA ATG CAA ATT ACT TAC TTC TGG     1267
Asn Asn Arg Val Met Asp Gly Tyr Pro Met Gln Ile Thr Tyr Phe Trp
370             375             380             385

CGG GGC TTG CCT CCT AGT ATC GAT GCA GTT TAT GAA AAT AGC GAC GGG     1315
Arg Gly Leu Pro Pro Ser Ile Asp Ala Val Tyr Glu Asn Ser Asp Gly
                390             395             400

AAT TTT GTG TTC TTT AAA GGT AAC AAA TAT TGG GTG TTC AAG GAT ACA     1363
Asn Phe Val Phe Phe Lys Gly Asn Lys Tyr Trp Val Phe Lys Asp Thr
        405             410             415

ACT CTT CAA CCT GGT TAC CCT CAT GAC TTG ATA ACC CTT GGA AGT GGA     1411
Thr Leu Gln Pro Gly Tyr Pro His Asp Leu Ile Thr Leu Gly Ser Gly
        420             425             430

ATT CCC CCT CAT GGT ATT GAT TCA GCC ATT TGG TGG GAG GAC GTC GGG     1459
Ile Pro Pro His Gly Ile Asp Ser Ala Ile Trp Trp Glu Asp Val Gly
        435             440             445

AAA ACC TAT TTC TTC AAG GGA GAC AGA TAT TGG AGA TAT AGT GAA GAA     1507
Lys Thr Tyr Phe Phe Lys Gly Asp Arg Tyr Trp Arg Tyr Ser Glu Glu
450             455             460             465

ATG AAA ACA ATG GAC CCT GGC TAT CCC AAG CCA ATC ACA GTC TGG AAA     1555
Met Lys Thr Met Asp Pro Gly Tyr Pro Lys Pro Ile Thr Val Trp Lys
                470             475             480

GGG ATC CCT GAA TCT CCT CAG GGA GCA TTT GTA CAC AAA GAA AAT GGC     1603
Gly Ile Pro Glu Ser Pro Gln Gly Ala Phe Val His Lys Glu Asn Gly
        485             490             495

TTT ACG TAT TTC TAC AAA GGA AAG GAG TAT TGG AAA TTC AAC AAC CAG     1651
Phe Thr Tyr Phe Tyr Lys Gly Lys Glu Tyr Trp Lys Phe Asn Asn Gln
        500             505             510

ATA CTC AAG GTA GAA CCT GGA CAT CCA AGA TCC ATC CTC AAG GAT TTT     1699
Ile Leu Lys Val Glu Pro Gly His Pro Arg Ser Ile Leu Lys Asp Phe
        515             520             525

ATG GGC TGT GAT GGA CCA ACA GAC AGA GTT AAA GAA GGA CAC AGC CCA     1747
Met Gly Cys Asp Gly Pro Thr Asp Arg Val Lys Glu Gly His Ser Pro
530             535             540             545

CCA GAT GAT GTA GAC ATT GTC ATC AAA CTG GAC AAC ACA GCC AGC ACT     1795
Pro Asp Asp Val Asp Ile Val Ile Lys Leu Asp Asn Thr Ala Ser Thr
                550             555             560

GTG AAA GCC ATA GCT ATT GTC ATT CCC TGC ATC TTG GCC TTA TGC CTC     1843
```

```
Val Lys Ala Ile Ala Ile Val Ile Pro Cys Ile Leu Ala Leu Cys Leu
            565                 570                 575

CTT GTA TTG GTT TAC ACT GTG TTC CAG TTC AAG AGG AAA GGA ACA CCC      1891
Leu Val Leu Val Tyr Thr Val Phe Gln Phe Lys Arg Lys Gly Thr Pro
            580                 585                 590

CGC CAC ATA CTG TAC TGT AAA CGC TCT ATG CAA GAG TGG GTG TGATGTA      1942
Arg His Ile Leu Tyr Cys Lys Arg Ser Met Gln Glu Trp Val
            595                 600                 605

GTTTTTTCTT CTTTCTTTCT TTTGCAGGAG TTTGTGGTAA CTTGAGATTC AAGACAAG      2002

CTGTTATGCT GTTCCTAGC TAGGAGCAGG CTTGTGGCAG CCTGATTCGG GGCTGACC       2062

TCAAACCAGA GGGTTGCTGG TCCTGCACAT GAGTGGAAAT ACACTCATGG GGAA          2116

(2) INFORMATION FOR SEQ ID NO: 2:

(i) SEQUENCE CHARACTERISTICS:
        (A) LENGTH: 607
        (B) TYPE: Amino acid
        (C) STRANDEDNESS: Single
        (D) TOPOLOGY: Linear (ii) MOLECULE TYPE: Protein (vi) ORIGINAL SOURCE:
        (A) ORGANISM: Human (xi) SEQUENCE DESCRIPTION: SEQ ID NO: 2:

Met Ile Leu Leu Thr Phe Ser Thr Gly Arg Arg Leu Asp Phe Val His
1               5                   10                  15

His Ser Gly Val Phe Phe Leu Gln Thr Leu Leu Trp Ile Leu Cys Ala
                20                  25                  30

Thr Val Cys Gly Thr Glu Gln Tyr Phe Asn Val Glu Val Trp Leu Gln
            35                  40                  45

Lys Tyr Gly Tyr Leu Pro Pro Thr Asp Pro Arg Met Ser Val Leu Arg
        50                  55                  60

Ser Ala Glu Thr Met Gln Ser Ala Leu Ala Ala Met Gln Gln Phe Tyr
65                  70                  75                  80

Gly Ile Asn Met Thr Gly Lys Val Asp Arg Asn Thr Ile Asp Trp Met
                85                  90                  95

Lys Lys Pro Arg Cys Gly Val Pro Asp Gln Thr Arg Gly Ser Ser Lys
            100                 105                 110

Phe His Ile Arg Arg Lys Arg Tyr Ala Leu Thr Gly Gln Lys Trp Gln
        115                 120                 125

His Lys His Ile Thr Tyr Ser Ile Lys Asn Val Thr Pro Lys Val Gly
    130                 135                 140

Asp Pro Glu Thr Arg Lys Ala Ile Arg Arg Ala Phe Asp Val Trp Gln
145                 150                 155                 160

Asn Val Thr Pro Leu Thr Phe Glu Glu Val Pro Tyr Ser Glu Leu Glu
                165                 170                 175

Asn Gly Lys Arg Asp Val Asp Ile Thr Ile Ile Phe Ala Ser Gly Phe
            180                 185                 190

His Gly Asp Ser Ser Pro Phe Asp Gly Glu Gly Gly Phe Leu Ala His
        195                 200                 205

Ala Tyr Phe Pro Gly Pro Gly Ile Gly Gly Asp Thr His Phe Asp Ser
    210                 215                 220

Asp Glu Pro Trp Thr Leu Gly Asn Pro Asn His Asp Gly Asn Asp Leu
225                 230                 235                 240

Phe Leu Val Ala Val His Glu Leu Gly His Ala Leu Gly Leu Glu His
```

-continued

```
                    245                 250                 255
Ser Asn Asp Pro Thr Ala Ile Met Ala Pro Phe Tyr Gln Tyr Met Glu
                260                 265                 270
Thr Asp Asn Phe Lys Leu Pro Asn Asp Leu Gln Gly Ile Gln Lys
            275                 280                 285
Ile Tyr Gly Pro Pro Asp Lys Ile Pro Pro Thr Arg Pro Leu Pro
        290                 295                 300
Thr Val Pro Pro His Arg Ser Ile Pro Pro Ala Asp Pro Arg Lys Asn
305                 310                 315                 320
Asp Arg Pro Lys Pro Arg Pro Pro Thr Gly Arg Pro Ser Tyr Pro
                325                 330                 335
Gly Ala Lys Pro Asn Ile Cys Asp Gly Asn Phe Asn Thr Leu Ala Ile
                340                 345                 350
Leu Arg Arg Glu Met Phe Val Phe Lys Asp Gln Trp Phe Trp Arg Val
            355                 360                 365
Arg Asn Asn Arg Val Met Asp Gly Tyr Pro Met Gln Ile Thr Tyr Phe
        370                 375                 380
Trp Arg Gly Leu Pro Pro Ser Ile Asp Ala Val Tyr Glu Asn Ser Asp
385                 390                 395                 400
Gly Asn Phe Val Phe Phe Lys Gly Asn Lys Tyr Trp Val Phe Lys Asp
                405                 410                 415
Thr Thr Leu Gln Pro Gly Tyr Pro His Asp Leu Ile Thr Leu Gly Ser
                420                 425                 430
Gly Ile Pro Pro His Gly Ile Asp Ser Ala Ile Trp Trp Glu Asp Val
            435                 440                 445
Gly Lys Thr Tyr Phe Phe Lys Gly Asp Arg Tyr Trp Arg Tyr Ser Glu
        450                 455                 460
Glu Met Lys Thr Met Asp Pro Gly Tyr Pro Lys Pro Ile Thr Val Trp
465                 470                 475                 480
Lys Gly Ile Pro Glu Ser Pro Gln Gly Ala Phe Val His Lys Glu Asn
                485                 490                 495
Gly Phe Thr Tyr Phe Tyr Lys Gly Lys Glu Tyr Trp Lys Phe Asn Asn
                500                 505                 510
Gln Ile Leu Lys Val Glu Pro Gly His Pro Arg Ser Ile Leu Lys Asp
            515                 520                 525
Phe Met Gly Cys Asp Gly Pro Thr Asp Arg Val Lys Glu Gly His Ser
        530                 535                 540
Pro Pro Asp Asp Val Asp Ile Val Ile Lys Leu Asp Asn Thr Ala Ser
545                 550                 555                 560
Thr Val Lys Ala Ile Ala Ile Val Ile Pro Cys Ile Leu Ala Leu Cys
                565                 570                 575
Leu Leu Val Leu Val Tyr Thr Val Phe Gln Phe Lys Arg Lys Gly Thr
                580                 585                 590
Pro Arg His Ile Leu Tyr Cys Lys Arg Ser Met Gln Glu Trp Val
            595                 600                 605
```

(2) INFORMATION FOR SEQ ID NO: 3:

(i) SEQUENCE CHARACTERISTICS:
        (A) LENGTH: 20
        (B) TYPE: Nucleic acid
        (C) STRANDEDNESS: Single
        (D) TOPOLOGY: Linear (ii) MOLECULE TYPE: Other nucleic acid
        Synthetic DNA (xi) SEQUENCE DESCRIPTION: SEQ ID NO: 3:

SGNVVNGCWG AYATMRTSAT                                                    20

(2) INFORMATION FOR SEQ ID NO: 4:

(i) SEQUENCE CHARACTERISTICS:
        (A) LENGTH: 27
        (B) TYPE: Nucleic acid
        (C) STRANDEDNESS: Single
        (D) TOPOLOGY: Linear (ii) MOLECULE TYPE: Other nucleic acid
            Synthetic DNA (xi) SEQUENCE DESCRIPTION: SEQ ID NO: 4:

YTCRTSNTCR TCRAARTGRR HRTCYCC                                            27

(2) INFORMATION FOR SEQ ID NO: 5:

(i) SEQUENCE CHARACTERISTICS:
        (A) LENGTH: 14
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO: 5:

Gln Thr Arg Gly Ser Ser Lys Phe His Ile Arg Arg Lys Arg
 1               5                  10

(2) INFORMATION FOR SEQ ID NO: 6:

(i) SEQUENCE CHARACTERISTICS:
        (A) LENGTH: 14
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO: 6:

Glu Glu Val Pro Tyr Ser Glu Leu Glu Asn Gly Lys Arg Asp
 1               5                  10

(2) INFORMATION FOR SEQ ID NO: 7:

(i) SEQUENCE CHARACTERISTICS:
        (A) LENGTH: 18
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO: 7:

Pro Thr Ser Pro Arg Met Ser Val Val Arg Ser Ala Glu Thr Met Gln
 1               5                  10                  15
Ser Ala (2) INFORMATION FOR SEQ ID NO: 8:

(i) SEQUENCE CHARACTERISTICS:
        (A) LENGTH: 14
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO: 8:

Thr Leu Gly Asn Pro Asn His Asp Gly Asn Asp Leu Phe Leu
  1               5                  10

(2) INFORMATION FOR SEQ ID NO: 9:

(i) SEQUENCE CHARACTERISTICS:
             (A) LENGTH: 7
             (B) TYPE: Amino acid
             (C) STRANDEDNESS: Single
             (D) TOPOLOGY: Linear (ii) MOLECULE TYPE: Peptide (xi) SEQUENCE DESCRIPTION: SEQ ID NO: 9:

Gly Glu Ala Asp Ile Leu Val
  1               5

(2) INFORMATION FOR SEQ ID NO: 10:

(i) SEQUENCE CHARACTERISTICS:
             (A) LENGTH: 9
             (B) TYPE: Amino acid
             (C) STRANDEDNESS: Single
             (D) TOPOLOGY: Linear (ii) MOLECULE TYPE: Peptide (xi) SEQUENCE DESCRIPTION: SEQ ID NO: 10:

Gly Asp Ala His Phe Asp Asp Asp Glu
  1               5

(2) INFORMATION FOR SEQ ID NO: 11:

(i) SEQUENCE CHARACTERISTICS:
             (A) LENGTH: 7
             (B) TYPE: Amino acid
             (C) STRANDEDNESS: Single
             (D) TOPOLOGY: Linear (ii) MOLECULE TYPE: Peptide (xi) SEQUENCE DESCRIPTION: SEQ ID NO: 11:

Gly Glu Ala Asp Ile Met Ile
  1               5

(2) INFORMATION FOR SEQ ID NO: 12:

(i) SEQUENCE CHARACTERISTICS:
             (A) LENGTH: 7
             (B) TYPE: Amino acid
             (C) STRANDEDNESS: Single
             (D) TOPOLOGY: Linear (ii) MOLECULE TYPE: Peptide (xi) SEQUENCE DESCRIPTION: SEQ ID NO: 12:

Pro Arg Cys Gly Val Pro Asp
  1               5

(2) INFORMATION FOR SEQ ID NO: 13:

(i) SEQUENCE CHARACTERISTICS:
             (A) LENGTH: 24
             (B) TYPE: Amino Acid
             (C) STRANDEDNESS: Single -continued

```
        (D) TOPOLOGY: Linear (ii) MOLECULE TYPE: Peptide (xi) SEQUENCE DESCRIPTION: SEQ ID NO: 13:

Ala Ile Ala Ile Val Ile Pro Cys Ile Leu Ala Leu Cys Leu Leu
 1               5                  10                  15

Val Leu Val Tyr Thr Val Phe Gln Phe
                20

(2) INFORMATION FOR SEQ ID NO: 14:

(i) SEQUENCE CHARACTERISTICS:
        (A) LENGTH: 4
        (B) TYPE: Amino Acid
        (C) STRANDEDNESS: Single
        (D) TOPOLOGY: Linear (ii) MOLECULE TYPE: Peptide (xi) SEQUENCE DESCRIPTION: SEQ ID NO: 14:

Arg Xaa Lys Arg
 1
```

PROTEIN AND MONOCLONAL ANTIBODY SPECIFIC THERETO

This application is a divisional application of patent application Ser. No. 09/000,041 filed Feb. 20, 1998, now allowed as U.S. Pat. No. 6,191,255, issued Feb. 20, 2001, which is a 371 of PCT/JP96/01956 filed Jul. 12, 1996.

FIELD OF THE INVENTION

The present invention relates to a novel protein useful as a diagnostic tool for studies and researches relating to diagnostic and therapeutic applications to tumors, including uses in detecting tumor cells, estimating cancer malignancies, etc., and/or useful in other medical and physiological uses; and to a novel gene encoding said protein. More specifically, the present invention relates to a new membrane-type protein which is one of the MMPs having the activation capability of pro-matrix metalloproteinase 2 (pro-MMP-2), i.e. an activator for pro MMP-2, provided that said protein is different from the first membrane-type matrix metalloproteinase (MT-MMP-1), and to a gene coding for said protein. The present invention also encompasses a novel matrix metalloproteinase being specifically expressed in a human tumor cell surface layer (the instant novel matrix metalloproteinase is named "membrane-type matrix metalloproteinase-3 (MT-MMP-3)"); DNA containing a nucleotide sequence coding the protein; a host cell transformed or transfected with the DNA, a process for producing the matrix metalloproteinase which comprises using said host cell, a monoclonal antibody capable of specifically binding with the matrix metalloproteinase protein, and applications of said protein and antibody.

RELATED ART

An extracellular matrix may block the transfer of tumor cells in the invasion and metastasis of tumor cells that are present in a primary nest tissue. In order for tumor cells to transfer and invade into tissues, they must deviate from the primary nest and destroy peripheral extracellular matrixes. The metastasis of tumor cells progresses via destruction of basement membranes, invasion into and effusion from blood vessels, successful implantation on secondary organs, further growth, etc. The extracellular matrix that blocks tumor metastasis is composed of various complex components, including type IV collagen, proteoglycans, elastin, fibronectin, laminin, heparan sulfate, etc. A family of enzymes, generally named "Matrix Metalloprotenase" (hereinafter briefly referred to as "MMP"), with distinct substrate specificities are responsible for the degradation of the extracellular matrix.

It has been reported that MMP includes fibroblast-type collagenase (MMP-1), 72 kDa gelatinase (referred to as type IV collagenase or gelatinase A; MMP-2), 92 kDa gelatinase (referred to as type IV collagenase or gelatinase B; MMP-9), stromelysin-1 (MMP-3), matrilysin (MMP-7), neutrophilic collagenase (MMP-8), stromelysin-2 (MMP-10), stromelysin-3 (MMP-11), etc. (Crit. Rev. Oral. Biol. Med., 4: 197 to 250, 1993). These MMPs form a family, and the primary structure of genes has been already reported. The reported amino-acid sequences deduced from cDNA data of these MMPs are recognized to be homologous, which are constituted of an N-terminal signal peptide basically removed during secretion and processing, followed by a propeptide domain, a $Zn^+$-binding catalytic domain, a proline-rich hinge domain composed of 5 to 50 amino acids, and a C-terminal hemopexin coagulation enzyme-like domain. There is no hemopexin-like domain in MMP-7. MMP-2 and MMP-9 include a gelatine-binding domain in addition to these.

Among these MMPs, it has been reported many times that type IV collagenase (MMP-2 and MMP-9) acting on, as a dominant substrate, type IV collagen that is a principal constituent for basement membranes is highly expressed in high metastatic tumor cells and there has been suggested that tumor cells are associated with tumor invasion into basement membrane invasion (Cell., 64: 327 to 336, 1991). The regulation of MMP activation is believed to be performed in steps including at least transcription level, a step for converting a proenzyme form wherein its enzymatic activity is latent into an active enzyme form, and controls by tissue inhibitor of metalloproteinase (TIMP) being a specific inhibitor against MMPs, etc. (Trends Genet., 6: 121 to 125, 1990).

All of the MMPs are secreted as inactive zymogens. In in vitro studies, activation of MMP-1 and MMP-9 is shown to be produced with serine proteinases such as plasmin, trypsin, cathepsin G. It has also been reported that activation of MMP-9 is caused by the action of active MMP-3 (J. Biol. Chem., 267: 3581 to 3584, 1992). However, since MMP-2 has no cleavage site sensitive to the above mentioned proteinase, activation of MMP-2 is believed not to be generated thereby (Curr. Opin. Cell Biol., 5: 891 to 897, 1993).

It has also been reported that these MMPs are produced by not only tumor cells but also circumferential fibroblasts and inflammatory cells which produce distinct MMPs, respectively (Breast Cancer Res. Treat., 24: 209 to 218, 1993; and Curr. Opin. Cell Biol., 5: 891 to 897, 1993).

It has previously been reported that, among them, MMP-2 is expressed in fibroblasts at a variety of sites accompanied with remodeling of tissue constructs and its activation is specifically generated in cancer tissues exemplified by lung cancer, in comparison with normal tissue and cancer tissue MMP-2s (Clin., Exp., Metastasis, 11: 183 to 189, 1993). In MMP-9, there is a low frequency that an active type is detected. In addition, there is proved in in vitro studies that active MMP-2 is localized at the apical site of tumor invasion (invadopodia) and it is suggested that the active MMP-2 has an important role on tumor invasion (Cancer Res., 53: 3159 to 3164, 1993; and Breast Cancer Res. Treat., 53: 3159 to 3164, 1994).

Under these backgrounds, attention has been focused on the activation mechanism of MMP-2. As described previously, however, activation of MMP-1 and MMP-9 is mediated by serine proteinases such as trypsin while the activation mechanism of MMP-2 is still undisclosed. In particular, an activating factor for MMP-2 remains unidentified. When HT1080 cells (MMP-2 producing cells) are treated with concanavalin A or 12-o-tetradecanoylphorbol 13-acetate (TPA), it is known that active MMP-2 appears in cultured medium, and it is believed that MMP-2 activating factors are induced in these cells (J. Natl. Cancer Inst., 85: 1758 to 1764, 1993; and Clin. Exp. Metastasis., 11: 183 to 189, 1993). Since this MMP-2 activation is induced by cellular membrane fractions and the activation is suppressed by chelating agents or TIMP, the MMP-2 activating factors have been presumed to be a membrane-type MMP (J. Biol. Chem., 268: 14033 to 14039, 1993).

The present inventors have previously cloned novel MMP genes using genetic engineering techniques, and obtained cloned genes coding for a new MMP having a typical transmembrane (TM) domain at the C-terminus thereof and being capable of activating MMP-2 (Nature, 370: 61 to 65, 1994). In fact, when this gene is expressed in cultured cells, the gene products are localized on the cell membrane without secretion. Thus, the present inventors have named such MMP as "membrane-type MMP (MT-MMP)".

Since, as described above, for MMPs, specifically MMP-2, the active form is found specifically in tumor cells, it is increasingly recognized that such should be targeted by anti-cancer or anti-metastatic drugs. Still, since MMP-2 exists relatively homeostatically as a zymogen in normal tissues, the regulation of MMP-2 activation resides in a process of activating it to active enzymes. Therefore, it is considered that the retrieval or identification of activating factors which are keys to this is extremely important in view of markers in the diagnosis of cancers and in the determination of malignancy and targets of anti-metastatic drugs against cancers.

In addition, it has been pointed out that MMP-2 may be involved in the cleavage of : β-amyloid protein which is associated with the crisis of Alzheimer's diseases. The βamyloid protein is a part of amyloid protein precursors, ¼ of β-amyloid protein area is included in the membrane-spanning (or transmembrane) area of the amyloid protein precursor, and the rest is outside the cells. It has been recently disclosed that several metabolic pathways of amyloid protein precursors exist, one of which is a process including a cleavage of inner sites of the β-amyloid protein area with a protease called "α-secretase" and a discharge outside cells. It has been recently found that an amyloid protein-degrading activity is present in MMP-2, with the possibility that MMP-2 would function as α-secretase or an extracellular β-amyloid protein-degrading enzyme (Nature, 362 : 839, 1993). The β-amyloid protein is the main component of senile macula observed in the brains of patients with Alzheimer's diseases, and forms the core of senile macula by self-aggregation and deposition thereof. Since functional reduction of β-amyloid protein-degrading enzymes may occur in the brain of the patient with Alzheimer's diseases, attention is focused on MMP-2. Here, the key is a process for activating MMP-2. The MT-MMP previously identified by the present inventors (newly named "MT-MMP-1" herein) is believed to be an activating factor for MMP-2, but the existence of unknown MMPs such as MT-MMP-1 can be anticipated from the fact that a variety of components exists in the extracellular matrix. The existence of activating factors for MMP-2, other than MT-MMP-1, is still undeniable.

SUMMARY OF THE INVENTION

A primary object of the present invention is to provide novel proteins which (i) belong to a member of MMPs having the capability of activating pro MMP-2, (ii) are different from MT-MMP-1, (iii) have the capability of activating pro MMP-2, and (iv) are an activator for pro MMP-2; genes encoding the same; processes for producing said novel pro MMP-2 activating factor proteins; applications of the protein and gene, etc.

The present inventors have observed that an activating factor (activator) for pro MMP-2 is assumed as a member of membrane-type MMPs since activation of pro MMP-2 is induced by tumor cell membrane fractions and the activation is inhibited by chelating agents or TIMP; the present inventors thus have isolated the gene coding for novel MMP-2 capable of activating pro MMP-2 in the prior research. However, the present inventors have hypothesized the existence of MMP acting as a MMP-2 activator in addition to the above, or MMP biochemically differing from the known MMPs. Following various researches using genetic engineering techniques, the present inventors successfully isolated a gene coding for MMP that is a novel activating factor for pro MMP-2, and completed the present invention.

It has been known that MT-MMP-1 is a member of MMPs capable of activating pro MMP-2; however, other activating factors for pro MMP-2 have been neither isolated nor identified. The present inventors have now cloned novel MMP genes, i.e. pro MMP-2 activating factor genes, and disclosed an entire nucleotide sequence of the gene and an entire amino acid sequence thereof. The inventors originally named this novel MMP as "MT-MMP-2" (Japanese Patent Application, Nos. Hei 7-200319 (or JP Appln. No. 200319/1995) and 7-200320 (or JP Appln. No. 200320/1995), both filed on Jul. 14, 1995). Later, at the Gordon Research Conference on Matrix Metalloproteinases (Andover, N.H., Jul. 16–21, 1995), it was agreed upon renaming "MT-MMP-3" (The Journal of Biological Chemistry, Vol. 270, pp. 23013–23020 (1995)). Therefore, the instant "MT-MMP-3" indicates the substance identical with MT-MMP-2 as described in Japanese Patent Application Nos. 7-200319 and 7-200320.

The present invention relates to novel proteins, i.e. MT-MMP-3 and analogs thereof. Further, the present invention relates to novel DNA sequences coding for all or part of MT-MMP-3, to vectors having such DNA sequences, and to host cells transformed or transfected with such vectors. The present invention also includes the production of recombinant MT-MMP-3 and uses of said recombinant MT-MMP-3. The present invention relates to antibodies which specifically bind with MT-MMP-3. In another aspect, the present invention relates to reagents for measurement or assay which contain said product and to detecting, measuring or assaying methods using such reagents. In particular, methods for detecting or measuring MT-MMP-3 in vivo and in vitro are provided.

The present invention relates to (1) proteins or a salt thereof which (i) belong to a member of MMPs capable of activating pro MMP-2 but are not MT-MMP-1, (ii) are an activator for pro MMP-2 and (iii) have an activity identical with or substantially equivalent to naturally-occurring MT-MMP, or a salt thereof; (2) characteristic partial peptides of said protein or a salt thereof; (3) genes (for example, nucleic acids including DNA, RNA, etc.) coding for said protein or peptide; (4) vectors or plasmids which contain said gene operably with gene recombination techniques; (5) host cells transformed or transfected with such vectors or the like; (6) processes for producing said protein or a salt thereof which comprises culturing said transformed or transfected host cell (transformant or transfectant); (7) antibodies (in particular, monoclonal antibodies) obtained using a member selected from the group consisting of the protein or a salt thereof thus obtained in the above process and the characteristic partial peptide of the protein or a salt thereof thus obtained in the above process; (8) hybridoma cells which produce the antibody; and (9) measuring (assaying) and/or diagnostic means (i) using the isolated gene (including, for example, DNA, RNA, etc.) as a probe or (ii) using the antibody.

Particularly, the present invention relates to (1) proteins which (i) belong to a member of MMPs capable of activating pro MMP-2, (ii) are an activator for pro MMP-2 but different from MT-MMP-1 and (iii) have an activity identical with or substantially equivalent to native MT-MMP-3, or a salt thereof; (2) characteristic partial peptides of said protein or a salt thereof; (3) genes (including, for example, DNA, RNA, etc.) coding for said protein or peptide; (4) vectors or plasmids wherein said gene is contained operably with gene recombination techniques; (5) host cells transformed or transfected with such a vector or the like; (6) processes for producing said protein or a salt thereof which comprises culturing said transformed or transfected host (transformant or transfectant)); (7) antibodies (in particular, monoclonal antibodies) obtained using a member selected from the group consisting of said protein or a salt thereof thus obtained and the unique partial peptide of said protein or a salt thereof thus obtained; (8) hybridoma cells which produce the antibody; and (9) measurement (assay) and/or diagnosis means (i) using the isolated gene (including, for example, DNA, RNA, etc.) as a probe or (ii) using the antibody.

Preferably, the present invention is related to MT-MMP-3 or a salt thereof which has (i) an amino acid sequence represented by SEQ ID NO: 2 in the Sequence Listing or (ii) an amino acid sequence substantially equivalent to SEQ ID NO: 2.

The present invention provides:

(1) a protein or a salt thereof, which (i) belongs to a member of MMPs having the activation capability of pro MMP-2, (ii) has an activity identical with or substantially equivalent to naturally-occurring MT-MMP, and (iii) is a pro MMP-2 activating factor, excluding MT-MMP-1;

(2) the protein according to above (1), wherein the protein has a biological property or primary structural conformation identical with or substantially equivalent to that of native MT-MMP-3 or a salt thereof;

(3) the protein according to above (1) or (2), wherein a C-terminal area of the protein has (i) an amino acid sequence from $Ala^{564}$ to $Phe^{587}$ in the sequence represented by SEQ ID NO: 2 in the Sequence Listing or (ii) an amino acid sequence substantially equivalent thereto;

(4) the protein according to any of above (1) to (3), wherein the protein is MT-MMP-3 or a salt thereof which has (i) an amino acid sequence represented by SEQ ID NO: 2 in the Sequence Listing or (ii) an amino acid sequence equivalent thereto;

(5) the protein according to any of above (1) to (4), wherein the protein is the product of prokaryotic or eukaryotic expression of an exogenous DNA sequence;

(6) the protein according to any of above (1) to (5), wherein the protein has (i) the amino acid sequence of SEQ ID NO: 2 in the Sequence Listing or (ii) the substantially same amino acid sequence;

(7) a partial peptide (or a peptide fragment) of the protein according to any of above (1) to (6) or a salt thereof;

(8) a nucleic acid comprising a nucleotide sequence coding for the protein or the partial peptide according to any of above (1) to (7);

(9) the nucleic acid according to above (8) which is a DNA gene having a nucleotide sequence coding for MT-MMP-3 according to any of above (2) to (4);

(10) the nucleic acid according to above (8) or (9), having (i) an open reading frame region of the nucleotide sequence represented by SEQ ID NO: 1 in the Sequence Listing or (ii) a nucleotide sequence having an activity substantially equivalent thereto;

(11) a vector comprising the nucleic acid according to any of above (8) to (10);

(12) a transformant or transfectant harboring (i) the nucleic acid according to any of above (8) to (10) or (ii) the vector according to above (11);

(13) a process for producing the protein according to any of above (1) to (6) or a partial peptide thereof, which comprises:
 (i) culturing the transformant or transfectant according to above (12) in a nutrient medium capable of growing said transformant or transfectant, and
 (ii) producing, as a recombinant species, the protein according to any of above (1) to (6) or a partial peptide thereof, including MT-MMP-3 or a salt thereof;

(14) an antibody against (a) a protein or a salt thereof which (i) belongs to a member of MMPs having the activation capability of pro MMP-2, (ii) has an activity identical with or substantially equivalent to naturally-occurring MT-MMP, and (iii) is a pro MMP-2 activating factor, excluding MT-MMP-1, or (b) a partial peptide of said protein or a salt thereof;

(15) the antibody according to above (14), wherein the antibody is against the protein which has an activity or a primary structural conformation identical with or substantially equivalent to that of MT-MMP-3 or a salt thereof;

(16) the antibody according to above (14) or (15), wherein the antibody is against the protein that is MT-MMP-3 or a salt thereof having (i) an amino acid sequence represented by SEQ ID NO: 2 in the Sequence Listing or (ii) an amino acid sequence substantially equivalent thereto;

(17) the antibody according to any of above (14) to (16), wherein the antibody is against the protein which is a product obtained by expressing a foreign DNA sequence in prokaryotic or eukaryotic cells;

(18) the antibody according to any of above (14) to (17), wherein the antibody is against the protein which has (i) the amino acid sequence of SEQ ID NO: 2 in the Sequence Listing or (ii) the substantially same amino acid sequence;

(19) the antibody according to any of above (14) to (18), wherein the antibody is against a partial peptide of the protein or a salt thereof;

(20) the antibody according to any of above (14) to (19), wherein the antibody is an anti-serum;

(21) the antibody according to any of above (14) to (19), wherein the antibody is monoclonal;

(22) the antibody according to any of above (14) to (19) and (21), which is a monoclonal antibody against MT-MMP-3 or a salt thereof;

(23) a method for producing an antibody against (a) a protein or a salt thereof which (i) belongs to a member of MMPs having the activation capability of pro MMP-2, (ii) has an activity identical with or substantially equivalent to naturally-occurring MT-MMP, and (iii) is a pro MMP-2 activating factor, excluding MT-MMP-1, or (b) a partial peptide of said protein or a salt thereof, which comprises employing an antigen selected from the group consisting of said protein, said partial peptide and a salt thereof to raise the antibody thereagainst;

(24) a method for producing the antibody according to above (21) or (22), which comprises
 (A) fusing an antibody-producing cell obtained from an immunized animal with an immortal cell, wherein said antibody is against (a) a protein or a salt thereof which (i) belongs to a member of MMPs having the activation capability of pro MMP-2, (ii) has an activity identical with or substantially equivalent to naturally-occurring MT-MMP, and (iii) is a pro MMP-2 activating factor, excluding MT-MMP-1, or (b) a partial peptide of said protein or a salt thereof and said animal is immunized with the protein, the partial peptide or a salt thereof, and
 (B) selecting an immortal hybrid cell capable of an antibody against a protein including MT-MMP-3;

(25) a method for detecting and/or measuring MT-MMP-3, which comprises using (A) a reagent selected from the group consisting of (a) a protein or a salt thereof which (i) belongs to a member of MMPs having the activation capability of pro MMP-2, (ii) has an activity identical with or substantially equivalent to naturally-occurring MT-MMP, and (iii) is a pro MMP-2 activating factor, excluding MT-MMP-1, and (b) a partial peptide of said protein or a salt thereof, or (B) a reagent selected from the group consisting of the antibodies according to any of above (14) to (22);

(26) a labeled antibody against MT-MMP-3 for the method for detecting and/or measuring MT-MMP-3 (the detection and/or measurement of MT-MMP-3) according to above (25);

(27) a labeled protein or a salt thereof, for the method for detecting and/or measuring MT-MMP-3 (the detection and/or measurement of MT-MMP-3) according to above (25), wherein said labeled protein (i) belongs to a member of MMPs having the activation capability of pro MMP-2, (ii) has an activity identical with or substantially equivalent to naturally-occurring MT-MMP, and (iii) is a pro MMP-2 activating factor, excluding MT-MMP-1, or a labeled partial peptide of said protein or a salt thereof, for the method according Lo above (25);

(28) a labeled nucleic acid for detection and/or measurement of MT-MMP-3 expressing cells and/or tissues, wherein said nucleic acid encodes (A) a protein which (i) belongs to a member of MMPs having the activation capability of pro MMP-2, (ii) has an activity identical with or substantially equivalent to naturally-occurring MT-MMP, and (iii) is a pro MMP-2 activating factor, excluding MT-MMP-1, or (B) a partial peptide of said protein; and

(29) the nucleic acid according to above (28), which is a probe for hybridization.

In particular, the present invention provides:

(30) MT-MMP-3 or a salt thereof which has an amino acid sequence represented by SEQ ID NO: 2 in the Sequence Listing or an amino acid sequence substantially equivalent thereto;

(31) a partial peptide of MT-MMP-3 or a salt thereof according to above (30);

(32) a DNA gene comprising a nucleotide sequence coding for MT-MMP-3 according to above (30);

(33) the DNA gene according to above (32), which has a nucleotide sequence represented by SEQ ID NO: 1 in the Sequence Listing;

(34) a vector comprising the gene according to above (32);

(35) a transformant (or transformed cell) harboring (i) the gene according to above (32) or (ii) the vector according to above (34);

(36) a process for producing MT-MMP-3 or a salt thereof, which comprises culturing the transformant according to above (35) in a nutrient medium capable of growing said transformant to produce, as a recombinant protein, said MT-MMP-3 or a salt thereof;

(37) a process for producing an antibody against MT-MMP-3 or a salt thereof, which comprises using an antigen selected from the group consisting of MT-MMP-3 or a salt thereof according to above (30) and a partial peptide of said MT-MMP-3 or a salt thereof to raise the antibody thereagainst;

(38) an antibody against MT-MMP-3 according to above (31);

(39) the antibody (anti-MT-MMP-3 antibody) according to above (38), which is anti-serum;

(40) the antibody (anti-MT-MMP-3 antibody) according to above (38), which is monoclonal;

(41) a process for producing a monoclonal antibody against MT-MMP-3 (monoclonal anti-MT-MMP-3 antibody; anti-MT-MMP-3 mAb) according to above (40), which comprises fusing an anti-MT-MMP-3 antibody-producing cell with an immortal cell and selecting an immortal hybrid cell (hybridoma cell) capable of producing anti-MT-MMP-3 mAb, wherein said anti-MT-MMP-3 antibody-producing cell is obtained from an animal immunized with a member selected from the group consisting of MT-MMP-3 or a salt thereof according to above (30) and a partial peptide of said MT-MMP-3 or a salt thereof;

(42) a method for detecting and/or measuring MT-MMP-3, which comprises using (A) a reagent selected from the group consisting of MT-MMP-3 or a salt thereof according to above (30) and a partial peptide of said MT-MMP-3 or a salt thereof, or (B) a reagent selected from the group consisting of anti-MT-MMP-3 antibodies according to above (38);

(43) Labeled MT-MMP-3 or a salt thereof, or a labeled partial peptide of MT-MMP-3, for the method for detecting and/or measuring MT-MMP-3 according to above (42); and

(44) a labeled antibody against MT-MMP-3 (labeled anti-MT-MMP-3 antibody) for the method for detecting and/or measuring MT-MMP-3 according to above (42).

BRIEF DESCRIPTION OF THE DRAWINGS

FIGS. 1A to 1E illustrate the domain structure of MT-MMP-3 according to the present invention, in comparison with the known MMP family members: MMP-1, MMP-2, MMP-3, MMP-7, MMP-8, MMP-10, MMP-11, MMP-12 and MT-MMP-1. An alignment of amino acid sequences of the MMP family members is shown wherein the homology among the amino acid sequence of MT-MMP-3 and the reported amino acid sequences of the known MMP family members: MMP-1, MMP-2, MMP-3, MMP-7, MMP-8, MMP-10, MMP-11, and MT-MMP-1 is compared. Each amino acid residue is indicated by a conventional single character symbol, and numbered, provided that the N-terminus of pre-type proteins is designated as the first amino acid residue.

FIG. 2 is photographs showing the electrophoretic results of Northern blotting.

A: RNA blot analysis of MT-MMP-3 mRNA in various human tissues by Northern blotting.

B: RNA blot analysis of MT-MMP-3 mRNA in various cultured human malignant cell lines by Northern blotting.

FIG. 3 is a photograph showing the electrophoretic results of immunoprecipitation of cell lysates and conditioned culture medium wherein MT-MMP-3 CDNA was expressed in COS-1 cells and MT-MMP-3 gene products (MT-MMP-3 proteins) were examined.

In autoradiography, MT-MMP-3 protein (64 kDa) and TIMP-1 protein (28 kDa) are indicated by arrows: ▲ and Δ respectively.

FIG. 4 is a photograph showing the electrophoretic results of the study that the fusion protein having a continuous sequence with TIMP-1/hydrophobic amino acid stretch at the C-terminus of MT-MMP-3 was prepared to examine the role of the continuous sequence composed of the hydrophobic amino acids at the C-terminus of MT-MMP-3 as a transmembrane (TM) domain.

The fusion proteins (chimeric proteins) constructed by gene engineering techniques were expressed in COS-1 cells and cell lysates and conditioned culture medium thereof were examined. The electrophoretic results detected by autoradiography are shown.

Figures 1, 1C, 2:
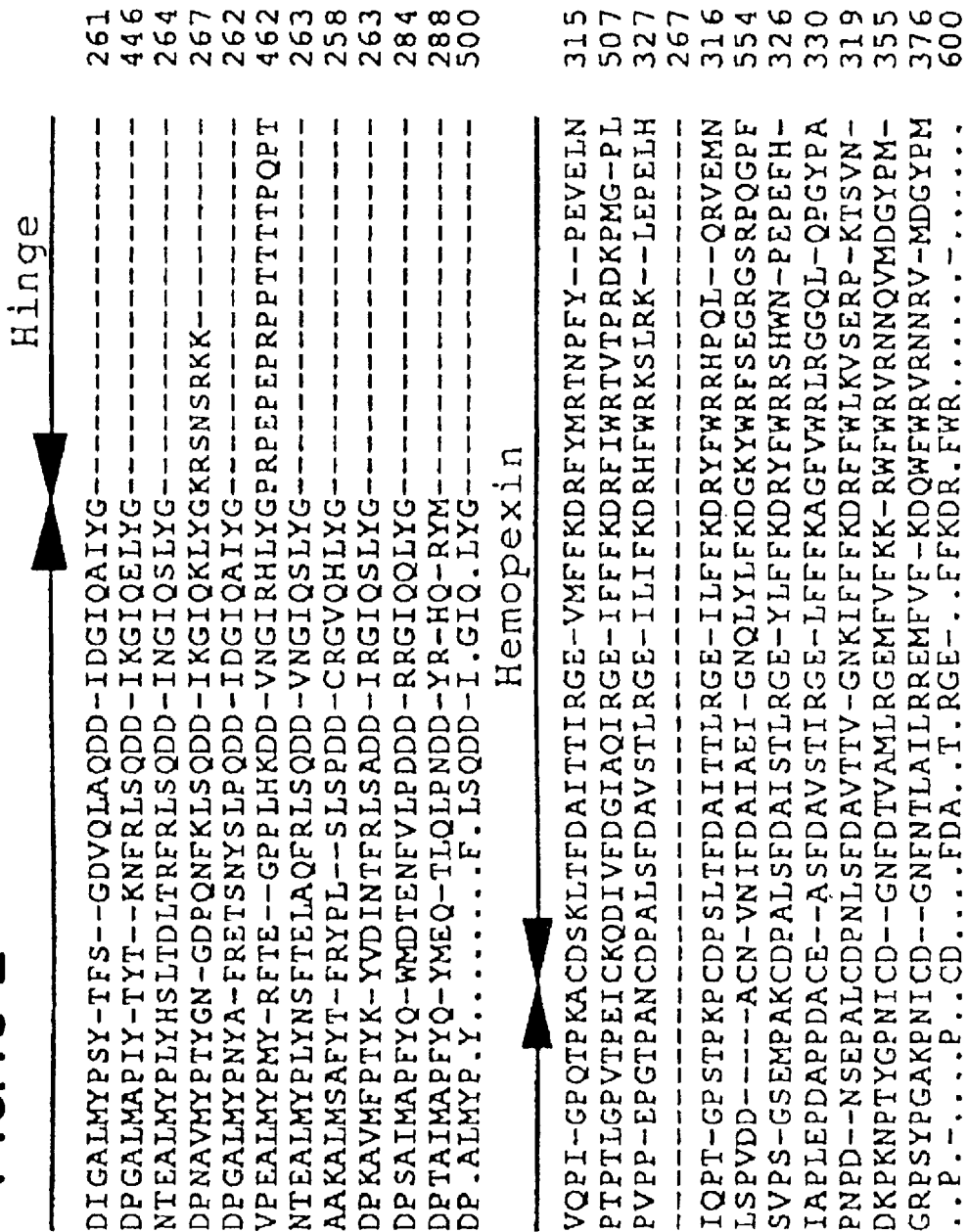
Figure 5:

FIG. 5 is photographs showing the results of immunofluorescence staining wherein the fusion protein having a continuous sequence with TIMP-1 hydrophobic amino acid stretch at the C-terminus of MT-MMP-3 was prepared to examine whether the continuous sequence composed of the hydrophobic amino acids at the C-terminus of MT-MMP-3 functions as a transmembrane (TM) domain.

Biological figures observed by immunofluorescence staining when the chimeric proteins having the continuous sequence with TIMP-1/hydrophobic amino acid stretch were expressed in COS-1 cells.

Figure 6:
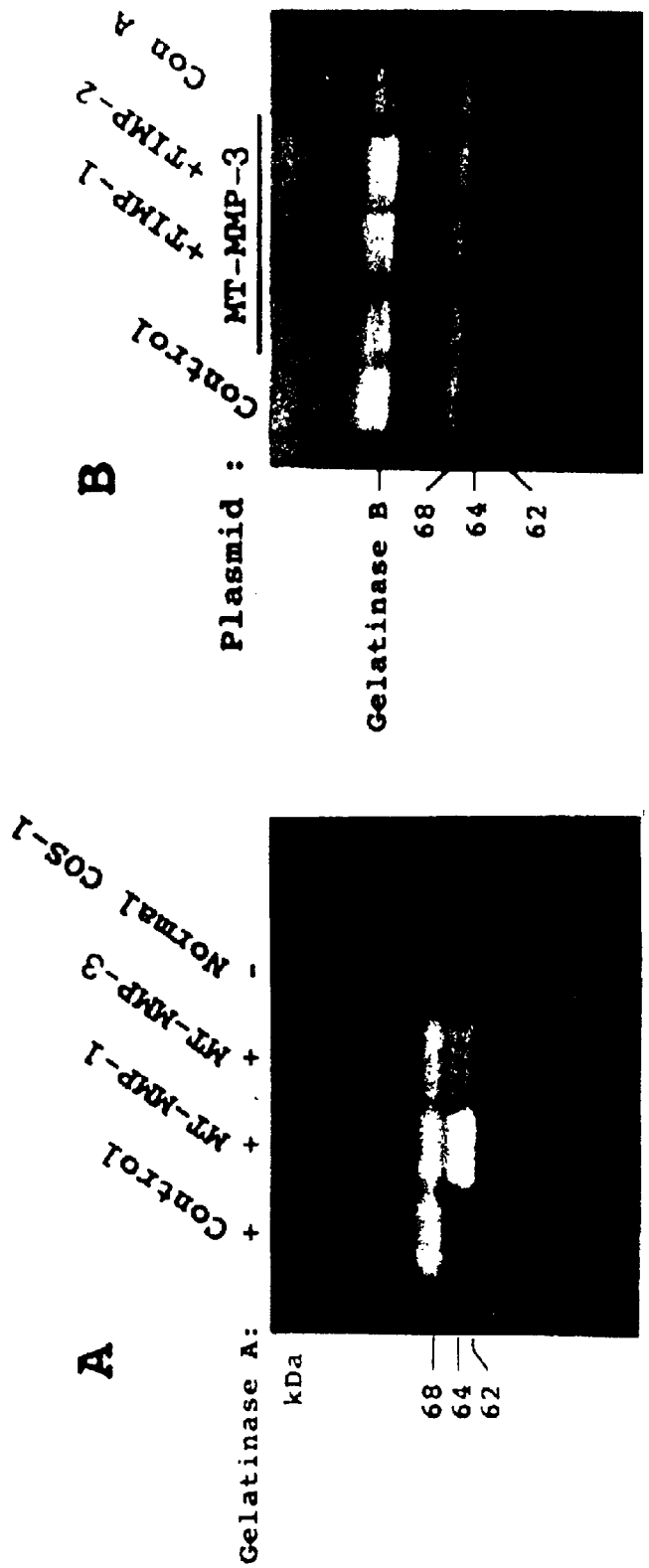

FIG. 6 is photographs showing the electrophoretic results of zymography analysis of activation of pro MMP-2 by MT-MMP-3 expression.

A: Activation of pro MMP-2 in COS-1 cells, wherein COS-1 cells cotransfected with MT-MMP-3 cDNA and pro MMP-2 cDNA.

B: Activation of pro MMP-2 by MT-MMP-3 and effect of TIMP-1 and TIMP-2 in HT 1080 cells into which MT-MMP-3 cDNA was cotransfected.

DESCRIPTION OF THE PREFERRED EMBODIMENTS

The present invention provides (1) a protein or a salt thereof (i) that is a member of MMPs capable of activating pro MMP-2 but is not MT-MMP-1, (ii) that has an activity identical with or substantially equivalent to native MT-MMP (for example, MT-MMP-3) which is a pro MMP-2 activation factor; (2) a specific partial peptide of that protein or a salt thereof; (3) a gene (such as DNA or RNA) coding for the same; (4) a vector or plasmid containing the gene operably by gene recombination techniques; (5) a host cell transformed by such a vector; and (6) a method for producing the protein or a salt thereof by culturing the host cell; (7) an antibody (in particular a monoclonal antibody) obtained using a species selected from the group consisting of the protein thus obtained or a salt thereof and partial peptides (peptide fragments) unique thereto or a salt thereof; (8) a hybridoma cell producing the antibody, and (9) measurement and diagnosis means using as a probe the isolated gene, such as DNA or RNA, or using the antibody.

More particularly, the present invention provides (i) MT-MMP-3 or a salt thereof which has the amino acid sequence of SEQ ID NO: 2 in the Sequence Listing. The MT-MMP-3 of the present invention may include those that are pro MMP-2 activating factors and have a new amino acid sequence as long as they are members of MMPs capable of activating pro MMP-2 but different from MT-MMP-1 and are capable of activating pro MMP-2. More preferably, the MT-MMP-3 of the present invention includes all substances having an amino acid sequence identical with or substantially equivalent to the amino acid sequence of SEQ ID NO: 2 in the Sequence Listing. Furthermore, the MT-MMP-3 of the present invention may have (i) as a pre portion, part or all of the amino acid sequence ranging from the first amino acid residue: Met to the 21st amino acid residue: Phe, and/or (ii) as a pro portion part or all of the amino acid sequence ranging from the 22nd amino acid residue: Phe to the 119th amino acid residue: Arg. All of MT-MMP-3 that have such a sequence may be included herein.

The MT-MMP-3 can be encoded by a nucleotide sequence comprising a region ranging between ATG from the 113th to 115th nucleotide residues of SEQ ID NO: 1 in the Sequence Listing and GTG from the 1931st to 1933rd nucleotide residues (termination codon: TGA from the 1934th to 1936th nucleotide residues may be replaced with TAA or TAG), and can also be encoded by any DNA sequence containing a nucleotide sequence homologous to the above nucleotide sequence but different from the MT-MMP-1 sequence as long as it is equivalent to a sequence for a species capable of activating pro MMP-2. The MT-MMP-3 nucleotide sequences can be modified (by addition, deletion, substitution), and those thus modified may be included herein.

The DNA containing a nucleotide sequence represented by SEQ ID NO: 1 or an equivalent thereof according to the present invention may be cloned and obtained, for example, by the following techniques:

It should be noted that gene recombination techniques may be conducted, for example, by the methods disclosed in T. Maniatis et al., "Molecular Cloning", 2nd Ed., Cold Spring Harbor Laboratory, Cold Spring Harbor, N. T. (1989); Nippon Seikagaku Kai (Biochemical Society of Japan) ed., "Zoku-Seikagaku Jikken Kouza 1, Idenshi Kenkyuho II (Lectures on Biochemical Experiments (Second Series; 1), Methods for Gene Study II)", Tokyo Kagaku Dojin, Japan (1986); Nippon Seikagaku Kai (Biochemical Society of Japan) ed., "Shin-Seikagaku Jikken Kouza 2, Kakusan III (Kumikae DNA Gijutsu) (New Lectures on Biochemical Experiments 2, Nucleic Acids III (Recombinant DNA Technique))", Tokyo Kagaku Dojin, Japan (1992); R. Wu (ed.), "Methods in Enzymology", Vol. 68, Academic Press, New York (1980); R. Wu et al. (ed.), "Methods in Enzymology", Vols. 100 & 101, Academic Press, New York (1983); R. Wu et al. (ed.), "Methods in Enzymology", Vols. 153, 154 & 155, Academic Press, New York (1987), etc. as well as by techniques disclosed in the references cited therein, the disclosures of which are hereby incorporated by reference, or by the substantially same techniques as they disclose or modified techniques thereof. Such techniques and means may also be those which are individually modified/improved from conventional techniques depending upon the object of the present invention. mRNA samples can be isolated from various human tissues (placenta, oral tumor, lung cancer, etc.), culture cells (human fibrosarcoma HT1080 cell line, human monocytic leukemia U937 cell line, etc.) and the like. In particular, mRNA can preferably be isolated from a human oral tumor cell (oral malignant melanoma). Although, in an embodiment, mRNA may be isolated with a method known in the art or by the substantially same method as it is or modifications thereof, the isolation and purification of mRNA can be conducted by methods disclosed in, for example, T. Maniatis, et al., "Molecular Cloning", 2nd Ed., Chapter 7, Cold Spring Harbor Laboratory, Cold Spring Harbor, N. T. (1989); L. Grossman, et al. ed., "Methods in Enzymology", Vol. 12, Parts A & B, Academic Press, New York (1968); S. L. Berger et al. ed., "Methods in Enzymology", Vol. 152, p. 33 & p. 215, Academic Press, New York (1987); Biochemistry, 18, 5294–5299, 1979; etc., the disclosures of which are hereby incorporated by reference. Examples of such mRNA isolating and purifying techniques are a guanidine-cesium chloride method, a guanidine thiocyanate method, a phenol method, etc. If necessary, the resulting total RNA may be subjected to a purification process using an oligo(dT)-cellulose column, etc. to give poly(A)$^+$mRNA.

cDNAs are prepared by using, as a template; the resulting mRNA and a reverse transcriptase, etc. The reverse transcriptase synthesis of cDNA using mRNA may be carried out by standard techniques known in the art, by the substantially same techniques or by modified techniques thereof. Detailed techniques are found in, for example, H. Land et al., "Nucleic Acids Res.", Vol. 9, 2251 (1981); U.

Gubler et al., "Gene", Vol. 25, 263–269 (1983); S. L. Berger et al. ed., "Methods in Enzymology", Vol. 152, p. 307, Academic Press, New York (1987); etc., the disclosures of which are hereby incorporated by reference.

Then, based upon the cDNA thus prepared, CDNA libraries can be constructed. Besides the technique using a phage vector, transformations of host cells including *Escherichia coli* may be conducted according to techniques known in the art, such as a calcium technique and a rubidium/calcium technique, or the substantially same methods (D. Hanahan, J. Mol. Biol., Vol. 166, p. 557 (1983), etc.). Various commercially available cDNA libraries derived from human tissues (for example, obtainable by CLONTECH, etc.) can also be used directly. A polymerase chain reaction (PCR) is conducted using the prepared cDNA as a template. In an embodiment, primers are synthesized which have degenerate oligonucleotides designed from highly conserved regions selected from amino acid sequences in a family of known MMPs. Preparation of primers may be carried out by techniques which are known in the art. For example, the primers may be synthesized by means of a phosphodiester method, a phosphotriester method, a phosphoamidite method, etc. using an automatic DNA synthesizer. The PCR amplification is carried out using said primers and the template CDNA thus prepared. The PCR may be carried out by techniques known in the art or by methods substantially equivalent thereto or modified techniques. The reaction may be conducted by the methods disclosed, for example, in R. Saiki, et al., Science, Vol. 230, pp. 1350 (1985); R. Saiki, et al., Science, Vol. 239, pp. 487 (1985); and PCR Technology, Stockton Press; etc., the disclosures of which are hereby incorporated by reference.

The resulting PCR products are cloned, and sequenced. As a result, DNA fragments having a novel MMP gene sequence are acquired. Sequencing of nucleotide sequences may be carried out by a dideoxy technique (such as an M13 dideoxy method), a Maxam-Gilbert method, etc. or may be carried out using a commercially available sequencing kit such as a Taq dyeprimer cycle sequencing kit or an automated nucleotide sequencer such as a fluorescent DNA sequencer. In particular, cDNA libraries constructed from various human tissues (placenta, oral tumors, lung cancers, etc.) or culture cells (human fibrosarcoma HT1080 cell line, human monocytic leukemia U937 cell line, etc.) are screened using the DNA fragment as a probe, and the target DNA can be isolated by sequencing of nucleotide sequences. Preferably, a human placenta CDNA library is screened, a detected DNA is sequenced, and the target DNA is isolated and identified. Labeling of probes, etc. with a radioisotope, etc., may be carried out using a commercially available labeling kit such as a random primed DNA labeling kit (Boehringer Mannheim).

The detailed description thereof is given below.

The inventors designed and synthesized the following: 5' primer having the following sequence:
5P-4 (SEQ ID NO: 3)

SGNVVNGCWGAYATMRTSAT wherein S=C or G, N=A, C, G or T, V=A, C, or G, W=A or T, Y=C or T, M=A or C, and R=A or G; mixed bases; and 3' primer having the following sequence:
3P-2 (SEQ ID NO: 4)

YTCRTSNTCRTCRAARTGRRHRTCYCC wherein Y=C or T, R=A or G, S=C or G, N=A, C, G or T, and H=A, C or T; mixed bases, based on highly conserved amino acid sequences GEADILV (SEQ ID NO: 9) and GDAHFDDDE (SEQ ID NO: 10), selected from the catalytic enzyme domain among the known MMP family.

In the above-mentioned sequences, symbols (S, N, V, W, Y, M, R, and H) indicate the incorporation of plural bases, leading to multiple oligonucleotides in the primer preparation. In other words, SEQ ID NO: 3 and SEQ ID NO: 4 are degenerate nucleotide primers.

Primers can be designed, synthesized, and used based on amino acid sequences in the area specific to the MMP family.

PCR was carried out using these primers and the cDNA library prepared from a human oral malignant melanoma. The obtained PCR products having a size (90 to 120 b.p.) expected from the primer design were sub-cloned and sequenced. As a result, there were obtained DNA fragments with a novel sequence homologous to the known MMPs, other than PCR products having a sequence identical with either MMP-1 or MMP-9.

Similarly, by using these primers and cDNA libraries derived from various human cells, PCR products with a novel sequence homologous to the known MMPs may be searched, other than PCR products with the same sequence as that of either MMP-1 or MMP-9.

The 93 b.p. DNA fragment was employed as a probe to screen for a human placenta cDNA library. As a result, 2.1-kilobase pair DNA fragments were obtained. The obtained DNA fragments were sequenced and the nucleotide sequence of SEQ ID NO: 1 was determined.

The same nucleotide sequence as that represented by SEQ ID NO: 1 does not exist in GENEBANK/EMBL DNA Data Base. Therefore, it has been recognized that DNA having the nucleotide sequence of SEQ ID NO: 1 is absolutely novel.

The nucleotide sequence of the above mentioned clone possessing a nucleotide sequence represented by SEQ ID NO: 1 has a 3' non-translational sequence together with an open reading frame potentially coding for a 607 amino acid protein. It has been recognized that a deduced signal sequence follows immediately downstream of the initiation codon and a hydrophobic domain which is composed of aligned 24 amino acid residues with higher hydrophobicity and is characteristic of membrane-type proteins is present at the C-terminal area from the 564th to 587th amino acid residues.

The novel MMP thus obtained has been named "MT-MMP-3" (the inventors first called it as "MT-MMP-2" in Japanese Patent Application Nos. 7-200319 and 7-200320, both filed on Jul. 14, 1995; however, the inventors has agreed to rename it as "MT-MMP-3", based on the agreements in the conference of Gordon Research Conference on Matrix Metalloproteinases (Andover, N.H. Jul. 16–21, 1995)).

MT-MMP-3 gene products are confirmed using suitable animal cells, such as COS-1 cells, transfected with the MT-MMP-3 gene. The foreign gene can be introduced into mammal animal cells with known methods in the art or with methods substantially similar thereto, including a calcium phosphate technique (for example, F. L. Graham et al., "Virology", Vol. 52, pp. 456 (1973), etc.), a DEAE-dextran technique (for example, D. Warden et al., "J. Gen. Virol.", Vol. 3, pp. 371 (1968), etc.), an electroporation technique (for example, E. Neumann et al., "EMBO J", Vol. 1, pp. 841 (1982), etc.), a microinjection technique, a liposome technique, a virus infection technique, a phage particle technique, etc.

Thus, the gene products which were produced by animal cells transfected with the MT-MMP-3 gene were examined by means of immunoprecipitation experiments using monoclonal anti-MT-MMP-3 antibodies. As a result, a 64 kDa protein was immunologically precipitated from the lysate of cells transfected with the MT-MMP-3 gene while no corresponding protein was detected in the culture medium. In other words, it is suggested that MT-MMP-3 gene products are expressed on the cell surface layer without being secreted.

The MT-MMP-3 protein has been examined for the homology with the reported amino acid sequences of the known MMP family. As shown in FIGS. 1A to 1E, it is revealed that MT-MMP-3 has high homology to the known MMP family. The MT-MMP-3 protein maintains the sequence at or near the processing site for conversion of a precursor form to a mature form (corresponding to the sequence conserved in the MMP family) as well as the sequence of the active site best. In addition, the propeptide domain characteristic of the primary structure of MMPs, the $Zn^+$ binding catalytic domain, the proline-rich hinge domain, and the C-terminal hemopexin coagulation enzyme-like domain are also well conserved in the MT-MMP-3 protein.

Similarly to MT-MMP-1 (the inventors rename the previously isolated and identified MT-MMP as "MT-MMP-1" in order to distinguish MT-MMP-3 therefrom), MT-MMP-3 has a sequence composed of aligned hydrophobic amino acids in the C-terminal region. It is therefore suggested that MT-MMP-3 is a membrane-type MMP. Such a sequence with aligned hydrophobic amino acids does not exist in the other MMP family members. In fact, when fusion proteins in which the aligned sequence composed of the hydrophobic amino acid residues is fused with a secretory protein by genetic engineering are constructed and expressed in culture cells, secretion of the fusion proteins was suppressed and expressed on the cell membranes. As a result, the aligned sequence composed of the hydrophobic amino acids is shown to function as a transmembrane (TM) domain.

Therefore, it is apparent that MT-MMP-3 gene codes for a novel MMP protein. Consequently, recombinant plasmids produced using MT-MMP-3 gene are all novel recombinant products, and transformants transformed or transfected with the plasmid are novel.

Any plasmid into which the MT-MMP-3 gene is incorporated may be used as long as said DNA can be expressed in host cells conventionally used in gene engineering techniques (such as procaryotic host cells including *Escherichia coli, Bacillus subtilis,* etc. and eucaryotic host cells including yeasts, CHO cell, and insect host cells such as Sf21). In such a sequence of the plasmid, it is possible, for example, to incorporate codons suitable for expressing the cloned DNA in selected host cells or to construct restriction enzyme sites. It is also possible to have control sequences, promotion sequences, etc. for facilitating the expression of the aimed gene; linkers, adaptors, etc. useful for ligating the aimed gene; sequences useful in controlling resistance to antibiotics or in controlling metabolism or in selection; and the like.

Preferably, suitable promoters may be used. For example, such promoters may include tryptophan (trp) promoter, lactose (lac) promoter, tryptophan-lactose (tac) promoter, lipoprotein (lpp) promoter, λ phage $P_L$ promoter, etc. in the case of plasmids where *Escherichia coli* is used as a host; SV40 late promoter, MMTV LTR promoter, RSV LTR promoter, CMV promoter, SRα promoter, etc. in the case of plasmids where an animal cell is used as a host; and GAL1, GAL10 promoters, etc. in the case of plasmids where yeast is used as a host.

Examples of the plasmid suitable for host *Escherichia coli* are pBR322, pUC18, pUC19, pUC118, pUC119, pSP64, pSP65, pTZ-18R/-18U, pTZ-19R/-19U, pGEM-3, pGEM-4, pGEM-3Z, pGEM-4Z, pGEM-5Zf(-), pBluescript KS™ (Stratagene), etc. Examples of the plasmid vector suitable for expression in *Escherichia coli* are pAS, pKK223 (Pharmacia), pMC1403, pMC931, pKC30, etc. The plasmid for host animal cells may include SV40 vector, polyomavirus vector, vaccinia virus vector, retrovirus vector or the like. Examples of the plasmid for host animal cells are pcD, pcD-SR α, CDM8, pCEV4, pME18S, pBC12BI, pSG5 (Stratagene) or the like. Examples of the plasmid for host yeasts are YIp vector, YEp vector, YRp vector, YCp vector, etc., including pGPD-2, etc. *Escherichia coli* host cells may include those derived from *Escherichia coli* K12 strains, such as NM533 XL1-Blue, C600, DH1, HB101 and JM109.

In the case where the host cells are animal cells, they may include COS7 cells, COS-1 cells, and CV-1 cells derived from African green monkey fibroblasts, COP cells, MOP cells, and WOP cells derived from mouse fibroblasts, CHO cells and CHO DHFR cells derived from chinese hamster, human HeLa cells, C127 cells derived from mouse cells, NIH 3T3 cells derived from mouse cells, etc. The insect cells may include *bombyx mori* larva, *bombyx mori* culture cells such as BM-N cells, etc. wherein *bombyx mori* nuclear polyhedrosis virus is employed as a vector.

In the gene engineering techniques of the present invention, it is possible to use various restriction enzymes, reverse transcriptases, DNA modifying and degrading enzymes which are used for modifying or converting a DNA fragment to a structure suitable for cloning, DNA polymerases, terminal nucleotidyltransferases, DNA ligases; etc., which are known or common in the art. Examples of the restriction enzyme are those disclosed in R. J. Roberts, "Nucleic Acids Res.", Vol. 13, r165 (1985); S. Linn et al. ed., "Nucleases", p. 109, Cold Spring Harbor Lab., Cold Spring Harbor, New York, 1982; etc., the disclosures of which are hereby incorporated by reference. Examples of the reverse transcriptase are those derived from mouse Moloney leukemia virus (MMLV), from avian myeloblastosis virus (AMV), etc. Particularly, RNase H-deficient reverse transferase or the like is preferably used. Examples of the DNA polymerase are *Escherichia coli* DNA polymerase, Klenow fragment which is a derivative of *E. coli* DNA polymerase, *E. coli* phage T4 DNA polymerase, *E. coli* phage T7 DNA polymerase, thermoduric bacteria DNA polymerase, etc.

The terminal nucleotidyltransferase includes TdTase capable of adding a dideoxynucleotide (dNMP) to a 3'—OH terminal, as disclosed in R. Wu et al. ed., "Methods in Enzymology", Vol. 100, p. 96, Academic Press, New York (1983). The enzyme for modifying and decomposing DNA includes exonuclease, endonuclease, etc. Examples of such enzymes are snake venom phosphodiesterase, spleen phosphodiesterase, *E. coli* DNA exonuclease I, *E. coli* DNA exonuclease III, *E. coli* DNA exonuclease VII, λ exonuclease, DNase I, nuclease S1, Micrococcus nuclease, etc. Examples of the DNA ligase are *E. coli* DNA ligase, T4 DNA ligase, etc.

The vector (or vehicle) which is suitable for cloning DNA genes and constructing DNA libraries includes plasmid, λ phage, cosmid, P1 phage, F factor, YAC, etc. Preferred examples of such vectors are vectors derived from λ phage, such as Charon 4A, Charon 21A, λ gt10, λ gt11, λ DASHII, λ FIXII, λ EMBL3 and λ ZAPII™ (Stratagene), etc.

Further, by relying on the nucleotide sequence of MT-MMP-3 gene according to the present invention, equivalent proteins or derivatives (or analogs) thereof wherein the amino acid sequence of MT-MMP-3 is altered may be produced with conventional gene technological methods. Such alterations includes substitution, deletion, insertion, transfer or addition of one or more amino acid residues, etc. Such methods for mutation, conversion, and/or modification may also include those described in Nippon Seikagaku Kai (Biochemical Society of Japan) ed., "Zoku-Seikagaku Jikken Kouza 1, Idenshi Kenkyuho II (Lectures on Biochemical Experiments (Second Series; 1), Methods for Gene Study II)", p.105 (Susumu HIROSE), Tokyo Kagaku Dojin, Japan (1986); Nippon Seikagaku Kai (Biochemical Society of Japan) ed., "Shin-Seikagaku Jikken Kouza 2, Kakusan III (Kumikae DNA Gijutsu) (New Lectures on Biochemical Experiments 2, Nucleic Acids III (Recombinant DNA Technique))", p.233 (Susumu HIROSE), Tokyo Kagaku Dojin, Japan (1992); R. Wu, L. Grossman, ed., "Methods in Enzymology", Vol.154, p.350 & p.367, Academic Press, New York (1987); R. Wu, L. Grossman, ed., "Methods in Enzymology", Vol.100, p.457 & p.468, Academic Press, New York (1983); J. A. Wells et al., "Gene", Vol.34, p.315 (1985); T. Grundstroem et al., "Nucleic Acids Res.", Vol.13, p.3305 (1985); J. Taylor et al., "Nucleic Acids Res.", Vol.13, p.8765 (1985); R. Wu ed., "Methods in Enzymology", Vol.155, p.568, Academic Press, New York (1987); A. R. Olipliant et al., "Gene", Vol.44, p.177 (1986), etc., the disclosures of which are hereby incorporated by reference. Examples of such techniques include site-directed mutagenesis (or site-specific mutagenesis) using synthetic oligonucleotides, Kunkel method, dNTP[αS] method (Eckstein method), area-directed mutagenesis using sulfite, nitrite, etc. and the like.

Further, the proteins thus obtained can be modified chemically for amino acid residues. The protein can also be modified or partially degraded with enzymes such as pepsin, chymotrypsin, papain, bromelain, endopeptidase, exopeptidase or the like to produce a derivative. In addition, the proteins may be expressed as fusion proteins when they are produced using gene recombinant techniques, which are subjected to in vivo and in vitro conversion into and/or processing to those having a biological activity substantially equivalent to native MT-MMP-3. The fusion protein production conventionally used in gene engineering can be employed. Further, such fusion proteins can be isolated and/or purified by means of affinity chromatography or the like wherein the technique employs a fusion portion thereof. The structure of proteins can be modified, improved, etc. by means of methods as described in Nippon Seikagaku Kai (Biochemical Society of Japan) ed., "Shin-Seikagaku Jikken Kouza 1, Tanpakushitsu VII, Tanpakushitsu Kougaku (New Lectures on Biochemical Experiments 1, Proteins VII, (Protein Engineering))", Tokyo Kagaku Dojin, Japan (1993), the disclosures of which are hereby incorporated by reference, or by techniques as described in references cited therein as well as methods substantially equivalent thereto.

In addition, as described herein below, the biological activity may include those having an immunological activity including an antigenic activity.

Hence, the present invention relates to proteins wherein one or more amino acid residues may differ from native amino acid residues from the viewpoint of homology, and proteins wherein the positions of one or more amino acid residues may differ from those of native residues. The present invention includes deletion analogs wherein one or more amino acid residues (for example, 1 to 80 residues, preferably 1 to 60 residues, more preferably 1 to 40 residues, further more preferably 1 to 20 residues, particularly 1 to 10 residues, etc.) characteristic of MT-MMP-3 are deleted; substitution analogs wherein one or more amino acid residues (for example, 1 to 80 residues, preferably 1 to 60 residues, more preferably 1 to 40 residues, further more preferably 1 to 20 residues, particularly 1 to 10 residues, etc.) characteristic of MT-MMP-3 are replaced with other amino acid residues; and addition analogs wherein one or more amino acid residues (for example, 1 to 80 residues, preferably 1 to 60 residues, more preferably 1 to 40 residues, further more preferably 1 to 20 residues, particularly 1 to 10 residues, etc.) are added. All of the above mentioned variants or the like are included in the present invention as long as domain structures or C-terminal transmembrane domains commonly characteristic of MMPs are maintained. It is thought that MT-MMP-3 of the present invention may include proteins having a primary structural conformation identical with or substantially equivalent to native MT-MMP-3 or a part thereof. It is also thought that MT-MMP-3 may include proteins having a biological activity identical with or substantially equivalent to native MT-MMP-3. It may be one of mutants (variants) naturally produced or occurred. The MT-MMP-3 according to the present invention can be separated, isolated and purified as described herein below.

The protein or a salt thereof, which (i) belongs to a member of MMPs having the capability of activating pro MMP-2, (ii) has an activity identical with or substantially equivalent to native MT-MMP (particularly, MT-MMP-3), and (iii) is a pro MMP-2 activating factor, excluding MT-MMP-1; or a partial peptide (or peptide fragment) thereof or a salt thereof is useful and valuable in studies on development and research of enzyme inhibitors using said protein or the like, research and development of medicines, studies on biological phenomenon and reaction with which MT-MMP-3 is thought to be associated, etc. Further, the protein and partial peptide or a salt thereof can be used for production of antibodies thereagainst. The products of the present invention can be mused for investigation and research on specific targets to be assayed or measured.

The present invention also relates to DNA sequences coding for any of the above mentioned polypeptides, MT-MMP-3 polypeptides, and MT-MMP-3 analogs and derivatives, each having all or part of characteristics, unique properties, etc. of native MT-MMP-3.

The DNA sequences of the present invention provides information concerning the amino acid sequences of the mammal proteins that have not been known so far. Therefore, utilization of the above information is included in the present invention. Such utilization includes design of any of probes for isolating and detecting mammal, in particular human, genomic DNA or cDNA, encoding MT-MMP-3, related (or associated) proteins, etc.

The DNA sequences of the present invention are useful as probes for isolating and detecting mammal, most preferably human, genomic DNA and cDNA, coding for MT-MMP-3 or related proteins thereof. To isolate genes, PCR techniques or PCR using reverse transcriptase (RT) (RT-PCR) can be used. MT-MMP-3 cDNA and associated DNA thereof can be used in isolating and detecting MT-MMP-3-related genes, via selecting characteristic sequence regions based on amino acid sequences deduced from the cloned and sequenced MT-MMP-3 cDNA sequence, then designing and chemically synthesizing DNA primers, and carrying out PCR, RT-PCR, or any other techniques with the obtained DNA primers.

Since MT-MMP-3 conserves well the structural characteristics of MT-MMP-1, there is assumed the possibility that MT-MMP-3 also acts as an activating factor for pro MMP-2. Therefore, mammal cells such as COS-1 cells have been cotransfected with a plasmid for expressing pro MMP-2 together with a plasmid for expressing MT-MMP-3. Zymography was carried out for the recollected culture medium of the cotransfectants. As a result, a 62 kDa active MMP-2 and a 64 kDa active intermediate have been detected, other than pro MMP-2 which is primarily observed at the position of molecule weight 68 kDa, and the activation of pro MMP-2 depending on the expression of MT-MMP-3 has been observed.

The expression of MT-MMP-3 mRNA in human tissues has been examined by Northern blotting for various tissue-derived poly (A)$^+$RNA. As a result, it has been recognized that MT-MMP-3 mRNA is highly expressed in human lungs, brains, and placentas. However, no expression has been found in human hearts, kidneys, livers, pancreas, and muscle tissues. In studies done by the inventors, the expression of MT-MMP-1 mRNA is significantly high in human lungs, kidneys, and placentas, while lowest in the human brains. These observations show that, although MT-MMP-3 is closely analogous structurally, and functionally in terms of the capability of activating pro MMP-2, to MT-MMP-1, expression of the genes for MT-MMP-3 and MT-MMP-1 in the actual tissues is differently regulated. When the cDNA according to the present invention is employed as a probe, techniques including Northern blotting, Southern blotting, in situ hybridization or the like enable us to detect and/or measure MT-MMP-3 mRNA expression or MT-MMP-3 genes per se in human tissues, which may contribute greatly to applications to studies on diagnosis and treatment of tumors (including cancers) such as diagnosis of the presence and absence of tumor cells, malignancy of cancers, on diagnosis of Alzheimer's diseases, etc.

According to inventor's investigation results as described herein above, techniques are provided for transferring MT-MMP-3 genes and recombinant DNA molecules into hosts, expressing MT-MMP-3 therein, and isolating and obtaining target MT-MMP-3. Thus, according to the present invention, transformants or transfectants capable of substantially expressing MT-MMP-3 genes and production processes thereof are provided.

In another aspect, the present invention related to nucleic acids, such as DNA or RNA, which enable us to express
(i) a protein or a salt thereof, (a) being a member of MMPs capable of activating pro MMP-2 but not MT-MMP-1, and (b) having an activity identical with or substantially equivalent to native MT-MMP that is an activator for pro MMP-2,
(ii) more preferably a polypeptide or a salt (a) having a biological property or a primary structural conformation, identical with or substantially equivalent to MT-MMP-3 or a salt thereof, and (b) having at least part or all of the protein,
in a prokaryotic cell such as *E. coli* or an eukaryotic cell such as a mammal cell.

In addition, such nucleic acids, particularly DNA, may include (a) sequences coding for an amino acid sequence represented by SEQ ID NO: 2 in Sequence Listing or sequences complementary thereto; (b) sequences capable of hybridizing with the DNA sequences (a) or fragments thereof; and (c) sequences having degenerate codons hybridizable with either of the sequences (a) and (b). The unique features of the present invention also reside in transformed prokaryotic cells, such as *E. coli*, and transformed eukaryotic cells, such as mammal cells, which are transformed with said nucleic acid and can express the polypeptides according to the present invention.

The present invention further provides antibodies, such as monoclonal antibodies, capable of specifically binding with MT-MMP-3. The antibodies, such as monoclonal antibodies, of the present invention contribute to development and supply of tools useful for researches associated with diagnosis of malignant tumors or cancers, as well as studies on invasion and metastasis of cancers and means useful for researches associated with the crisis mechanism or diagnostic techniques Alzheimer's disease. Such tools and means are within the scope of the present invention.

The antibody, such as monoclonal antibody, according to the present invention can be produced by immunizing animals with, as an immunogen, human MT-MMP-3 obtained according to the present invention based on techniques known or widely applicable in the art. Examples of such techniques are found in Milstein et al., Nature, 256: 495 to 497, 1975, etc., the disclosures of which are hereby incorporated by reference. In this technique, the antigen used may include any of naturally-occurring (native) MT-MMP-3, recombinant human MT-MMP-3, synthetic peptides having an amino acid sequence composed of at least continuous 8 amino acids which are part of MT-MMP-3, etc. The monoclonal antibody can be labeled using conventional techniques. The labels (markers) may include enzymes, prosthetic molecules, pigment (chromophore) substances, fluorescent substances, chemiluminescent compounds, photoluminescent substances, radioactive substances or the like.

Described herein below is the production of antibodies.

It goes without saying that the monoclonal antibody to be used in the present invention may be a monoclonal antibody obtained by utilizing cell fusion techniques with myeloma cells.

The monoclonal antibody to be used in the present invention can be produced by the following processes:
1. Preparation of immunogenic antigens (immunogens)
2. Immunization of animals with immunogenic antigens
3. Preparation of myeloma cells
4. Cell fusion between antibody-producing cells and myeloma cells
5. Selection and cloning of hybridomas (hybrid cells)
6. Production of monoclonal antibodies 1. Preparation of Immunogenic Antigens The antigen used includes naturally occurring MT-MMP-3 and recombinant MT-MMP-3 as prepared according to the present invention. Although MT-MMP-3 may be used after formation of immunogenic conjugates, it can be used to immunize animals after being mixed with a suitable adjuvant without any modifications. Such antigens can be separated, isolated and purified from various sources, for example, antigen-producing sources including cultured cells, cultured tissues, transformant cells, etc. by conventional techniques. Such conventional techniques are, for example, salting out such as ammonium sulfate fractionation, etc.; gel filtration on Sephadex™, etc.; ion exchange chromatography using carriers having, for example, a diethylaminoethyl or carboxymethyl group, etc.; hydrophobic chromatography using carriers having, for example, a hydrophobic group such as butyl, octyl, or phenyl, etc.; pigment (or chromophore) gel chromatography; electrophoresis; dialysis; ultrafiltration; affinity chromatography; high performance liquid chromatography; etc. Preferably, the antigen to be used is separated and purified by polyacrylamide electrophoresis, affinity chromatography in which an antibody for specifically recognizing an antigen, such as a monoclonal antibody, is immobilized. Examples of such techniques also include gelatine-agarose affinity chromatography, heparin-agarose chromatography, etc.

MT-MMP-3 may be fragmented or may include a synthetic polypeptide fragment obtained via selecting specific (or characteristic) sequence areas based on amino acid sequences deduced from the cloned and sequenced cDNA sequences followed by design and chemical synthesis. The fragments may be coupled with various carrier proteins via suitable coupling agents to form immunogenic conjugates such as hapten-proteins. The immunogenic conjugates can be used to design monoclonal antibodies that can recognize only specific sequences. A cysteine residue or the like can be added to the polypeptide thus designed so as to prepare an immunogenic conjugate easily. To fix with a carrier protein or the like, the carrier protein is first activated. This activation may include incorporation of an activated binding group hereinto, etc. The activated binding groups include (1) active ester or active carboxyl groups such as a nitrophenyl ester group, a pentafluorophenyl ester group, a 1-benzotriazol ester group, and an N-succinimide ester group; (2) active dithio groups such as a 2-pyridyldithio group, etc. The carrier proteins include keyhole limpet haemocyanin (KLH), bovine serum albumin (BSA), ovalbumin, globulin, polypeptides such as polylysine, bacterial components such as BCG or the like.

2. Immunization of Animals with Immunogenic Antigens

Animals can be immunized according to techniques as described in Shigeru MURAMATSU et al. ed., "Jikken Seibutsu Gaku Kouza 14, Men-eki Seibutsu Gaku (Lectures on Experimental Biology 14, Immunobiology)", Maruzen K. K., 1985; Nippon Seikagaku Kai (Biochemical Society of Japan) ed., "Zoku-Seikagaku Jikken Kouza 5, Men-eki Seikagaku Kenkyuho (Lectures on Biochemical Experiments (Second Series; 5), Methods for Immunological and Biochemical Study)", Tokyo Kagaku Dojin, Japan (1986); Nippon Seikagaku Kai (Biochemical Society of Japan) ed., "Shin-Seikagaku Jikken Kouza 12, Bunshi Men-eki Gaku III (Kougen-Koutai-Hotai) (New Lectures on Biochemical Experiments 12, Molecular Immunology III (Antigen-Antibody-Complement))", Tokyo Kagaku Dojin, Japan (1992); etc., the disclosures of which are hereby incorporated by reference. The adjuvant to be used with the antigen includes Freund's complete adjuvant, Ribi adjuvant, *Bordetella pertussis* vaccine, BCG, lipid A, liposome, aluminium hydroxide, silica, etc. Immunization is carried out with animals, including mice such as BALB/c. The antigen dose is, for example, approximately 1 to 400 µg/animal for mice. Generally, the antigen is injected intraperitoneally or subcutaneously into a host animal, followed by additional immunization by repeated courses wherein intraperitoneal, subcutaneous or intravenous administrations are carried out approximately 2 to 10 times at 1- to 4-week intervals, preferably 1- to 2-week intervals. For immunization, BALB/c mice, as well as F1 mice between BALB/c mice and other mice, etc. can be used.

As required, the degree of animal immunization can be assessed by constructing a system for measuring a titre of antibody and measuring the titre of an antibody. Furthermore, the present invention relates to polyclonal antibodies against MT-MMP-3 and the production thereof using recombinant MT-MMP-3. In this case, the animal used may include mammals, birds or the like. Examples of such animals are cow, horse, goat, sheep, swine, rabbit, mouse, rat, guinea pig, monkey, dog, cat, cock, hen, etc. The antibody may be anti-serum. Also, the antibody may be a higher purified form. For example, its isolation and purification can be carried out in the same manner as the monoclonal antibody described herein below.

3. Preparation of Myeloma Cells

Immortal cell strains (tumor cell lines) to be used for cell fusion can be selected from non-immunoglobulin-producing cell lines. The cell strains to be used for cell fusion may include, for example, P3-NS-1-Ag4-1 (NS-1, Eur. J. Immunology, 6, 511 to 519, 1976), SP2/0-Ag14 (SP2, Nature, 276, 269 to 270, 1978), mouse myeloma MOPC-21 cell line-derived P3-X63-Ag8-U1 (P3U1, Current topics in Microbiol. and Immunol., 81, 1 to 7, 1978), P3-X63-Ag8 (X63, Nature, 256, 495 to 497, 1975), P3-X63-Ag8-653 (653, J. Immunol., 123, 1548 to 1550, 1979), etc. 8-azaguanine resistant mouse myeloma cell lines can be sub-cultured in a medium for cell culture wherein antibiotics such as penicillin, amikacin or the like, fatal calf serum (FCS) or the like and 8-azaguanine (for example, 5 to 45 µg/ml) are added to a medium for cell culture, such as Dulbecco's modified Eagle's medium (DMEM) or RPMI-1640 medium. The specified number of cell lines can be prepared by passing the normal medium two or five days before cell fusion. The cell lines to be used may be cultured on the normal medium after the frozen and preserved strains have been completely thawed at approximately 37° C. and have been washed on the normal medium such as RPMI-1640 three or more times, and the specified number of cell strains may be prepared.

4. Cell Fusion Between Antibody-producing Cells and Myeloma Cells

After animals such as mice are immunized according to the above step 2, their spleens are removed in two to five days from final immunization, and the spleen cell suspension is obtained. In addition to the spleen cells, lymph node cells at various sites of organisms can be obtained and used for cell fusion. The spleen cell suspension thus obtained and the myeloma cell strains obtained by the above step 3 are placed in a medium such as minimum essential medium (MEM), DMEM or RPMI-1640 medium, and an agent for cell fusion, fusogen, such as polyethylene glycol, is added. A widely-used agent for cell fusion can be used, including HVJ: Hemagglutinating virus of Japan (Sendai virus). Preferably, 0.5 to 2 ml of 30 to 60% polyethylene glycol can be added. Polyethylene glycol with 1,000 to 8,000 in molecule weight can be employed, more preferably, polyethylene glycol between 1,000 and 4,000 in molecule weight. The preferred concentration of polyethylene glycol in the fusion medium is between 30 and 60%. As required, a small amount of dimethyl sulfoxide or the like is added to promote fusion. The ratio of spleen cells (lymphocytes) : myeloma cell lines to be used for fusion is preferably 1:1 to 20:1, and preferably falls between 4:1 and 7:1.

The fusion reaction is conducted for one to 10 minutes, before the addition of a medium such as RPMI-1640 medium. Fusion reaction processing can be done several times. After fusion reaction processing, cells are separated by a centrifuge, then transferred to the selection medium.

5. Selection and Cloning of Hybridomas (Hybrid Cells)

The selection media include conventionally known "HAT medium", i.e., PCS-containing MEM, RPMI-1640 medium, etc., supplemented with hypoxanthine, aminopterin, and thymidine. The replacement method for the selection medium is to replenish an amount equivalent to the capacity dispensed to the medium plate on the following day, after which the medium is replaced by half an amount in HAT medium every one to three days. The replacement can be modified depending on situations. Eight to sixteen days after fusion, the medium may be replaced every one to four days with conventionally known "HT medium" wherein aminopterin is excluded from HAT medium. As a feeder cell, for example, mouse thymocyte can be used, which is sometimes effective.

The supernatant of the culture well with highly growing hybridoma is screened by using MT-MMP-3 or a peptide fragment thereof as an antigen or by using a labeled antimouse antibody for measuring target antibodies, with a measuring system such as radioimmunoassay (RIA), enzyme-linked immunosorbent assay (ELISA), fluorescence immunoassay (FIA) or by the fluorescence activated cell sorter (FACS), etc. The target antibody-producing hybridoma is cloned. Cloning is carried out by picking up colonies in the agar medium or preferably by the limiting dilution. Cloning should be performed several times.

6. Production of Monoclonal Antibodies

The obtained hybridoma cells are cultured in a suitable growth medium such as FCS-containing MEM, RPMI-1640 medium or the like, and a desired monoclonal antibody can be obtained from the culture supernatant. Large amounts of monoclonal antibodies can be produced by propagating hybridomas as ascites tumors. In this case, each hybridoma is implanted intraperitoneally in a histocompatible animal isogenic to an animal from which the myeloma cell is derived and is propagated. Or each hybridoma can be inoculated, for example, in nude mice, and propagated to produce the monoclonal antibody in the ascites of the animals. The produced monoclonal antibody can be collected from the ascetic fluid and obtained. Prior to implantation of hybridomas, the animal is pretreated intraperitoneally with mineral oils such as pristane (2,6,10,14-tetramethylpentadecane). After the preconditioning, the hybridoma can be propagated therein and the ascitic fluid can be harvested. The ascitic fluid can be used as a monoclonal antibody without purification or after purification by conventionally known methods, including salting out such as precipitation with ammonium sulfate, gel filtration with Sephadex, ion exchange chromatography, electrophoresis, dialysis, ultrafiltration, affinity chromatography, high-performance liquid chromatography, and can be employed. Preferably, the monoclonal antibody-containing ascitic fluid is fractionated with ammonium sulfate and separated and purified by treatments with cationic ion exchange gel such as DEAE-Sepharose, an affinity column such as protein A column, etc. More preferably, it is treated with affinity chromatography with immobilized antigens or antigen fragments (for example, synthetic peptides, recombinant antigen proteins or peptides, portions capable of specifically recognizing the antibody); affinity chromatography with immobilized protein A; etc.

It is possible to produce antibodies by recombinant DNA techniques wherein the antibody thus obtained in a large amount is sequenced and/or a nucleotide sequence coding for the antibody obtained from the hybridoma cell line is employed.

These antibodies may be treated with enzymes such as trypsin, papain, pepsin or the like to produce antibody fragments including Fab, Fab', and F (ab')$_2$ that are occasionally obtained by reduction. These antibody fragments may be occasionally used.

The antibody to be labeled with a marker may include IgG fractions, and specific bonding fragments Fab' obtainable by reduction after pepsin digestion. The labels include enzymes (peroxidase, alkaline phosphatase, or β-D-galactosidase or the like), chemical substances, fluorescences, radioisotopes, or the like.

In the present invention, detection and measurement can be carried out by immunostaining including, for example, staining of tissues and cells, immunoassays including, for example, competitive immunoassay and non-competitive immunoassay, radioimmunoassay, ELISA, or the like. The detection and measurement can also be carried with or without B-F separation. Preferably, the detection and measurement is carried out by means of radioimmunoassay, enzyme immunoassay or sandwich assay. In the sandwich-type assay, one of the antibody pair against MT-MMP-3 is detectably labeled. The other antibody capable of recognizing the same antigen is immobilized on a solid phase. Incubation is carried out to sequentially react a sample to be assayed, labeled antibodies, and immobilized antibodies as required. After the non-binding antibodies are separated, the label or marker is detected or measured. The amount of the measured label is proportional to the amount of antigen, i.e., MT-MMP-3. For this assay, simultaneous sandwich assay, forward sandwich assay, or reverse-sandwich assay or the like is called according to the addition sequence of the insolubilized antibody and the labeled antibody. For example, washing, stirring, shaking, filtration, pre-extraction for antigen, etc. is optionally adopted in the measurement process under specific conditions. The other measurement conditions such as specific regents, concentration of buffering solution, temperature or incubation time can vary according to the elements, such as concentration of the antigens in the sample or the nature of samples to be measured. Any person ordinary skilled in the art can suitably select and determine optimal conditions effective for each measurement while using the general experimentation and perform the selected measurement.

Various carriers capable of immobilizing antigens or antibodies are available in the art, and they can be arbitrarily and suitably selected in the present invention. For the carrier, various carriers which can be used for antigen and antibody reactions are known. It goes without saying that any well-known carrier can be selected and used in the present invention. Preferred examples are inorganic materials including, for example, glass such as activated glass and porous glass, silica gel, silica-alumina, alumina, magnetized iron, magnetized alloy, etc.; organic high molecular substances including, for example, polyethylene, polypropylene, polyvinyl chloride, polyvinylidene fluoride, polyvinyl acetate, polymethacrylate, polystyrene, styrene/butadiene copolymer, polyacrylamide, cross-linked polyacrylamide, styrene/methacrylate copolymer, polyglycidyl methacrylate, acrolein/ethylene glycol dimethacrylate copolymer, etc., cross-linked albumin, collagen, gelatin, dextran, agarose, cross-linked agarose, natural or modified cellulose such as cellulose, microcrystalline cellulose, carboxymethylcellulose, cellulose acetate and the like, cross-linked dextran, polyamide such as nylon, polyurethane, polyepoxy resin and the like; those obtained by emulsifying polymerization thereof; cells, erythrocytes and the like; and those into which a functional group may be introduced, as required, by using a silane coupling agent.

Also included are solid materials such as filtration paper, beads, inner wall of test container such as test tube, titer plates, titer wells, glass cells, cells made of synthetic materials such as plastic resin cells, glass rods, rods made of synthetic materials, rods thickened or thinned at the end, rods whose end is round or flat, and thin-plated rods.

Antibodies can be coupled with these carriers, and preferably the monoclonal antibodies according to the present invention which are capable of specifically binding with MT-MMP-3, can be coupled therewith. Coupling between the carrier and those associated with these antigen-antibody reactions can be carried out by techniques including physical method such as adsorption; a chemical method using a coupling agent, etc. or an activated reactant; a method using a chemically interactional coupling.

The label may include enzyme, enzyme substrates, enzyme inhibitors, prosthetic groups, coenzymes, enzyme precursors, apoenzymes, fluorescent substances, pigments, chemical luminescent compounds, light-emitting substances, coloring substances, magnetic substances, metal particles such as gold colloids, radioactive substances and the like.

The enzyme may include oxidation-reduction enzymes such as dehydrogenase, reductase, and oxidase; transferases that catalyze the transfer of an amino, carboxyl, methyl, acyl, phosphate group or the like; hydrolases that hydrolyze an ester, glycoside, ether, peptide bond or the like; lyase; isomerase; ligase; and the like. Plural enzymes can be used in a conjugated form for detection (for example, enzymatic cycling may also be utilizable).

Typical radioactive isotopes for the label include $[^{32}P]$, $[^{125}I]$, $[^{131}I]$, $[^3H]$, $[^{14}C]$, $[^{35}S]$, and the like.

Typical enzymes for the label include peroxidases such as horseradish peroxidase; galactosidase such as $E.\ coli$ $\beta$-D-galactosidase; maleate dehydrogenase; glucose-6-phosphate dehydrogenase; glucose oxidase; gluocoamylase; acetylcholine esterase; catalase; alkaline phosphatase such as calf intestinal alkaline phosphatase and $E.\ coli$ alkaline phosphatase, and the like.

In the case where alkaline phosphatase is used, fluorescence or emitted light can be measured by using a substrate such as umbelliferone derivatives including 4-methylumbellipheryl phosphate; phenol phosphate derivatives including nitrophenyl phosphate; enzymatic cycling systems utilizing NADP; luciferin derivatives; dioxetane derivatives; and the like. It is also possible to use a luciferin/luciferase system.

When catalase is used, the reaction takes place with hydrogen peroxide to produce oxygen which can be detected with an electrode or the like. The electrode may be a glass electrode, an ionic electrode using an insoluble salt membrane, a liquid-membrane type electrode, a polymer membrane electrode and the like.

It is possible to replace the enzyme label with a biotin label and an enzyme-labeled avidin (streptoavidin).

For the label, a plurality of many different kinds of labels or markers can be used. In this case, it is possible to perform plural measurements continuously or discontinuously and/or simultaneously or separately.

According to the present invention, a signal can be formed by using a combination of 4-hydroxyphenylace uic acid, 1,2-phenylenediamine, tetramet hiylbenzidine, or the like with horseradish peroxidase, by using a combination of umbelliferyl galactoside, nitrophenyl galactoside, or the like with enzyme reagents such as $\beta$-D-galactosidase and glucose-6-phosphoric acid dehydrogenase. There can be further used those that are capable of forming a quinol compound such as hydroquinone, hydroxybenzoquinone or hydroxyanthraquinone, a thiol compound such as lipoic acid or glutathione, phenol derivatives or ferrocene derivatives by utilizing the action of enzymes.

The fluorescent substance and chemiluminesce it compounds may include fluorescein isothiocyanate, Rhodamine derivatives such as Rhodamine B isothiocyanate, and tetramethyl Rhodamine isothiocyanate, dansyl chloride (5-(dimethylamino)-1-naphtalenesulfonyl chloride), dansyl fluoride, fluorescamine (4-phenylspiro[furan-2(3H) , 1'-(3'H)-isobenzofuran]-3,3'-dione) , phycobiliprotein, acridinium salts, luminol compounds such as lumiferin, luciferase, and aequorin, imidazole, oxalic acid ester, rare earth chelate compounds, cumarin derivatives, etc.

The labelling can be accomplished by utilizing the reaction of a thiol group with a maleimide group, reaction of a pyridyldisulfide group with a thiol group, the reaction of an amino group with an aldehyde group, etc. Additionally, it can be selected from widely known methods, methods that can be easily put into practice by an artisan skilled in the art, or any of methods modified therefrom. The coupling agents used for producing the foregoing immunoconjugate or for coupling with carriers are also applicable and usable.

The coupling agents include, for example, glularaldehyde, hexamethylene diisocyanate, hexamethylene diisothiocyanate, N,N'-polymethylene bisiodoacetamide, N,N'-ethylene bismaleimide, ethylene glycol bissuccinimidyl succinate, bisdiazobenzidine, 1-ethyl-3-(3-dimethylaminopropyl) carbodiimide, succinimidyl 3-(2-pyridyldithio)propionate (SPDP), N-succinimidyl 4-(N-maleimidometyl)cyclohexane-1-carboxylate (SMCC), N-sulfosuccinimidyl 4-(N-maleimidomethyl)-cyclohexane-1-carboxylate, N-succinimidyl (4-iodoacetyl)-aminobenzoate, N-succinimidyl 4-(1-maleimidophenyl) butyrate, N-($\epsilon$-maleimidocaproyloxy)succinimide (EMCS), iminothiolane, S-acetylmercaptosuccinic anhydride, methyl-3-(4'-dithiopyridyl)propionimidate, methyl-4-mercaptobutyrylimidate, methyl-3-mercaptopropionimidate, N-succinimidyl-S-acetylmercaptoacetate, etc.

According to the measurement of the present invention, substances to be measured can be made to react sequentially with labeled antibody reagents such as monoclonal antibodies labeled with enzymes or the like, and with antibodies coupled (immobilized) on a carrier, or all the members can be reacted each other simultaneously. The sequence of adding reagents (members) may vary depending on the type of carrier system selected. In the case where beads such as sensitized plastics are used, the labeled antibody regents such as monoclonal antibodies labeled with enzymes or the like are first put in a suitable test tube, together with a sample including substances to be measured, followed by addition of the plastic beads. Measurement can be then carried out.

For quantitative measurements according to the present invention, the immunological measurement is applied. For the measurement, the solid phase carriers used may include various materials and shapes which can be selected from balls, microplates, sticks, microparticles, test tubes, and the like, made of polystyrene, polycarbonate, polypropylene, polyvinyl and other materials capable of adsorbing proteins such as antibodies.

The measurement can be carried out in a suitable buffer system so as to maintain an optimal pH (for example, between pH about 4 and about 9). In particular, the preferred buffers may include acetate buffer, citrate buffer, phosphate buffer, tris buffer, triethanolamine buffer, borate buffer, glycine buffer, carbonate buffer, tris-hydrochloride buffer, etc. The buffers can be used optionally in a mixed form at an arbitrary rate. Preferably, the antibody and antigen reaction is carried out at a temperature between about 0 and 60° C.

The antibody regents (for example, monoclonal antibodies labeled with enzymes), the regents such as antibodies immobilized on (coupled to) a carrier, and substances (samples) to be measured can be incubated until equilibrium is reached. However, the reaction can be stopped after limited incubation by separating the solid phase from the liquid phase at a time well before the antibody/antigen equilibrates, and the degree of the presence of markers such as enzymes in either of the liquid and solid phases can be measured. Measurement operation can be performed by using automated measuring instruments, and data can be measured by permitting a substrate to be converted by the action of enzymes and by detecting produced indication signals with a luminescence detector, a photo detector or the like.

In the antibody/antigen reaction, adequate means can be taken so as to stabilize regents to be used, substances (samples) to be measured, and labels (markers) such as enzymes, respectively, and/or to stabilize antibody/antigen reactions per se. Further, for eliminating non-specific reaction, reducing inhibitory influences acting thereon, and/or activating measurement reaction, proteins, stabilizers, surfactants, chelating agents or the like can be added to solutions which are incubated. The chelating agent is more preferably ethylenediamine tetraacetate (EDTA). The blocking techniques for preventing non-specific binding reaction, which techniques are generally employed in the art or well-known among the persons skilled in the art, may be employed. The blocking can be achieved by treatments with normal serum proteins, albumin, skim milk or the like from mammals, etc., fermented milk products, collagen, gelatin, or the like. These methods or techniques can be used without any limitation since the purpose is to prevent non-specific binding reaction.

The samples to be measured according to the present invention may include various types of solutions such as colloid solution, non-fluid samples and the like. Preferably, the samples are biological samples including, for example, blood, serum, plasma, articular fluid, cerebrospinal fluid, saliva, amniotic fluid, urine, any other humoral fluids, cell culture liquids, tissue culture liquids, tissue homogenate, biopsy samples, tissues, cells and the like.

It should be understood that the DNA of the present invention can be treated in the similar manner as the foregoing antibodies (for example, the DNA can be labeled by well-known techniques or substantially equivalents thereto, and can be used for measurements or assays).

By utilizing the foregoing various preferred embodiments according to the present invention, there can be provided diagnostic means useful for researches regarding diagnosis or therapy of cancers (malignant tumors), including diagnosis of the presence or absence of tumor cells, estimation of malignancy of cancers and tumors as well as a variety of technological means to be applied to the other medical and physiological applications.

By referring to the working examples, the present invention is described below in detail. It should be understood that the present invention is not limited to such examples and a variety of preferred embodiments within the spirit of this specification are enabled.

In the case where nucleotides (bases), amino acids or the like are indicated by abbreviations in the specification and in the drawings, they must conform with an "IUPAC-IUB Commission on Biochemical Nomenclature" or are based on the meanings of the terms which are commonly used in the art. When optical isomers are present in amino acids, an L-isomer is referred to unless otherwise specified.

The transformant *Escherichia coli,* designated NM533 XL1-Blue (XL1-Blue/MMP-X2), obtained in Example 1 (e) mentioned herein below has been deposited as from Jul. 5, 1995 (original deposit date) with the National Institute of Bioscience and Human Technology (NIBH), Agency of Industrial Science and Technology, Ministry of International Trade and Industry, Japan, located at 1–3, Hligashi 1-chome, Tsukuba-shi, IBARAKI (zip Code: 305), JAPAN and has been assigned the Accession Number FERM P-15033. The original deposit of the transformant *E. coli* NM533 XL1-Blue (XL1-Blue/MMP-X2) has been transferred to one under the Budapest Treaty by a request dated Jul. 1, 1996 and is on deposit with the Accession Number FERM BP-5573 under the terms of the Budapest Treaty at NIBH.

The mouse-derived monoclonal anti-human membrane-type matrix metalloproteinase-3 (MT-MMP-3) antibody producing hybridoma, designated 117-4E1, obtained in Example 3 (f) to (h) mentioned herein below has been deposited as from Jul. 5, 1995 (original deposit date) with NIBH and has been assigned the Accession Number FERM P-15031. The original deposit of the hybridoma 117-4E1 has been transferred to one under the Budapest Treaty by a request dated Jul. 1, 1996 and is on deposit with the Accession Number FERM BP-5572 under the terms of the Budapest Treaty at NIBH.

EXAMPLES

Described below are examples of the present invention which are provided only for illustrative purposes, and not to limit the scope of the present invention. In light of the present disclosure, numerous embodiments within the scope of the claims will be apparent to those of ordinary skill in the art.

Example 1

Isolation of Novel Metalloproteinase (MT-MMP-3) cDNA

Isolation of novel MMP cDNA is basically carried out according to the following methods:

1) Degenerate primers were synthesized based on the conservative sequences in an MMP family. Screening for cDNA derived from human tissues was carried out, and PCR products were obtained. 2) The obtained partial clones were used as probes, and full length cDNA was screened from cDNA libraries.

(a) Construction of cDNA Libraries

Total RNA extracts from various human tissues (placenta, oral cancers, lung cancers or the like) or cultured cells (human fibrosarcoma cell HT1080, human monocytic leukemia cell U937 or the like) can be used as RNA sources in producing cDNA libraries. mRNA samples derived from an oral malignant melanoma were used as starting materials in Example 1.

Extraction of total RNA from the tissues was carried out according to the guanidine-cesium chloride technique (Biochemistry, 18: 5294 to 5299, 1979), and the total RNAs thus obtained was purified using oligo(dT) cellulose column to afford poly (A)$^+$mRNA. cDNA was synthesized according to the Gubler & Hoffman's method (Gene, 25: 263 to 269, 1983). The purified poly (A)$^+$mRNA as a template was treated with SuperScript™ reverse transcriptase (Stratagene) using, as primers, random hexamers or oligo dT to synthesize first-strand cDNA. The first strand cDNA product was treated with RNase H, followed by treatment with *E. coli* DNA polymerase I, whereby second strand cDNA was synthesized to form double-stranded cDNA. For the synthesis of first strand cDNA, a mixture of 5 $\mu$l of poly A$^+$mRNA fraction samples, 2 $\mu$l of random hexamers (80 $\mu$M), and 4.5 $\mu$l of reaction buffer solution was incubated for 10 minutes at 70° C. and ice-cooled. To the reaction mixture were added 4 $\mu$l of 5×reaction buffer solution, 2 $\mu$l of 0.1M dithiothreitol (DDT), 1 $\mu$l of 10 mM dNTPs and 1 $\mu$l of RNase inhibitor. The mixture was well mixed, to which 0.5 $\mu$l (approximately 100 units) of SuperScript™ reverse transcriptase (GIBCO BRL) was added. The resultant mixture was incubated for one hour at 37° C., and then for 10 minutes at 70° C. The synthesis of the second chain of cDNA can be similarly processed and carried out.

Construction of cDNA libraries can be carried out, for example, using λ gt11. The synthesized double strand cDNA was blunted with T$_4$ DNA polymerase, followed by methylation of EcoRI site existing in the cDNA with EcoRI methylase. The CDNA was ligated with EcoRI linker d(pGGAATTCC) by $T_4$ DNA ligase, and digested with EcoRI to construct cDNA having both EcoRI ends. The resulting cDNA was cloned into EcoRI site of λ gt11. Then, the cDNA was packaged by an in vitro packaging kit, and cDNA libraries were constructed. A variety of commercially available human tissue-derived cDNA libraries (CLONTECH) can be used directly herein.

(b) Amplification of Novel MMP cDNA Fragments

A polymerase chain reaction (PCR) with Taq DNA polymerase was carried out using the obtained cDNA as a template and degenerate primers synthesized based on the amino acid sequences conserved in the MMP family. PCR amplification of novel MMP cDNA fragments was done using, for example, methods as described in R. Saiki, et al., Science, Vol. 230, pp, 1350 (1985); R. Saiki, et al., Science, Vol. 239, pp. 487 (1985); PCR Technology, Stockton Press, etc.

One μl of the reaction product obtained in the above process as a template, 5 μl of 10×PCR buffer solution, 1 μl of 25 mM dNTPs, 1 μl of primers for amplification, and 1 unit of Taq polymerase was mixed together with sterile distilled water such that the total amount was 50 μl. This reaction mixture was subjected to PCR amplification with 30 cycles wherein one cycle includes 93° C. for one minute, 55° C. for one minute, and 72° C. for one minute.

The degenerate primers were designed and synthesized as follows:

GEADIMI (SEQ ID NO: 11)(corresponding to $Gly^{155}$ to $Ile^{161}$ of MMP-1, $Gly^{165}$ to $Ile^{171}$ of MMP-2, $Gly^{155}$ to $Ile^{161}$ of MMP-3, $Gly^{150}$ to $Ile^{156}$ of MMP-7, $Gly^{154}$ to $Ile^{160}$ of MMP-8, $Arg^{162}$ to $Ile^{168}$ of MMP-9 1 $Gly^{154}$ to $Ile^{160}$ of MMP-10, $Gly^{151}$ to $Ile^{157}$ of MMP-11, and $Gly^{155}$ to $Val^{161}$ of MMP-12, respectively; numbering of amino acid residues is according to FIGS. 1A to 1E), and GDAHFDDDE (SEQ ID NO: 10)(corresponding to $Gly^{192}$ to $Glu^{201}$ of MMP-1, $Gly^{203}$ to $Glu^{211}$ of MMP-2, $Asn^{192}$ to $Glu^{201}$ of MMP-3, $Gly^{187}$ to $Glu^{196}$ of MMP-7, $Gly^{191}$ to $Glu^{201}$ of MMP-8, $Gln^{199}$ to $Glu^{208}$ of MMP-9, $Tyr^{191}$ to $Glu^{200}$ of MMP-10, $Glu^{188}$ to $Glu^{197}$ of MMP-11, and $Gly^{192}$ to $Glu^{201}$ of MMP-12, respectively; numbering of amino acid residues is according to FIGS. 1A to 1E) were selected as well conserved amino acid sequences from the catalytic domains among the known MMP family members (each amino acid residue in the sequences served as primers is represented by a standard single character symbol). Based on above amino acid sequences, the degenerate oligonucleotide primers for 5'-primer (5'-primer: 5P-4) of the following sequence:

(SEQ ID NO: 3)

5'-(C or G)G(A, C, G or T)(A, C or G)(A, C or G)(A, C, G or T)GC(A or T)GA(C or T)AT(A or C)(A or G)T(C or G)AT-3' and 3'-primer (3'-primer: 3P-2) of the following sequence: (SEQ ID NO: 4)

5'-(C or T)TC(A or G)T(C or G)(A, C, G or T)TC(A or G)TC(A or G)AA(A or G)TG(A or G)(A or G)(A, C or T)(A or G)TC(C or T)CC were synthesized according to β-cyanoethylphosphoamidite techniques with a DNA synthesizer: Model 392 (Applied Biosystems).

In the above-mentioned sequences, the parentheses indicate the incorporation of a plurality of bases, leading to multiple oligonucleotides in the primer preparation. The plural bases in parentheses were incorporated in the presence of a mixture of plural bases upon synthesis.

Upon the synthesis, a BamHI site was introduced onto the 5'-end of the primer: 5P-4, and an EcoRI site onto the 3'-end of the primer: 3P-2. The obtained primers 5P-4 and 3P-2 were purified with a Nick column (Pharmacia) equilibrated with a 10 mM sodium phosphate buffer solution (pH 6.8). Absorption at 260 nm was measured and the primer solution was made to 20 μM.

The obtained PCR products were separated with 10% agarose electrophoresis. Seven types of PCR products with predicted sizes (90 to 120 base pairs) from a set of the primers used were extracted and purified. Each purified PCR product was treated with BamHI and EcoRI, followed by subcloning into, for example, the BamHI, EcoRI site of a suitable plasmid such as pBluescript™ or pUC18. For example, 10 μl of PCR products were separated and confirmed by means of 10% polyacrylamide gel electrophoresis (PAGE), and approximately 120 to 130 bp PCR products were subcloned into a plasmid pBluescript™ vector. A reaction mixture of 1 μl of PCR products, 1μl of 10×ligation buffer solution, 2 μl of resuspended vector solution and 1 μl of T4 DNA ligase were incubated at 12° C. overnight. The obtained recombinant vector was introduced into suitable competent cells (for example, competent E. coli HB101 and competent XL1-Blue can be used) and subcloned in accordance with the protocols of a TA Cloning Kit (Invitrogen). Additionally, vectors such as pUC119 and pCR™ can be used. The nucleotide sequences of the cloned PCR products were sequenced using a fluorescent DNA sequencer Model 373A (Applied Biosystems) and a Taq dyeprimer cycle sequencing kit (Applied Biosystems).

The nucleotide sequences of these seven isolated and sequenced PCR products were compared with the nucleotide sequences of the known MMP members. As a result, two of the seven cloned cDNA fragments matched a portion of the already reported nucleotide sequence of MMP-2 (J. Biol. Chem., 261: 6600 to 6605, 1986) and the one matched a part of the nucleotide sequence of MMP-9 (J. Biol. Chem., 264: 17213 to 17221, 1989). Among four other PCR products, two cloned cDNA fragments were the nucleotide sequence irrelevant to MMPs; however, the remaining two were 93 bp, have the same sequence each other and conserve the deduced amino-acid sequence showing homology to the reported MMP genes. For convenience, this PCR product was named "MMP-X2 fragment".

(c) Screening of Novel MT-MMP-3 Genes from cDNA Library and Sequencing

Twenty-five ng of MMP-x2 fragments (cDNA fragments) obtained in the foregoing (b) were labeled with $[α-^{32}P]$ dCTP (Amersham), for example, using a random primed DNA labeling kit (Boehringer Mannheim), thereby the obtained probe having a specific activity of 2 to 5.0 CPM/μg. This was used as a probe for screening for cDNA libraries derived from various human tissues and cells.

Host cells, E. coli Y1090, were infected with human oral malignant melanoma cDNA libraries constructed in λ gt11 as described in the above (a) at a concentration of $4×10^4$ plaque forming units/15 cm² plate to form plaques. The E. coli Y1090 cell was first cultured in a L medium containing 0.02% maltose overnight, collected, and then suspended in 10 mM $MgSO_4$. This cell suspension was mixed with a phage solution and the resultant mixture was incubated at 37° C. for 15 min. to allow the adsorption of phages on host cells. The infected cells were spread on 15 cm² L plates prepared in advance by addition of soft agar. The plates were incubated at 42° C. overnight to form plaques. Then a nylon filter (for example, Hybond-N: Amersham, etc.) or nitrocellulose filter (for example, HATF: Millipore, etc.) was placed on the plate and was allowed to stand for about 30 seconds. The membrane (filter) was gently removed and dipped in an alkali denaturing solution (0.5 M NaOH and 1.5 M NaCi) for 1 min., and then in a neutralizing solution (0.5 M Tris-HCl buffer (pH 8) containing 1.5 M NaCi) for 15 min. This filter was washed with 2×SSPE (0.36 M NaCl, 20 mM $NaH_2PO_4$, and 2 mM EDTA), and then was air-dried. Transfer of the plaques to filters was repeated, and at least two filters were replicated. However, the contact time for the second and subsequent filters with the plates was extended to approximately 2 minutes.

These filters were baked at 80° C. for two hours to fix DNAs thereon. At least two filters prepared from a single plate were rinsed with a washing solution (50 mM Tris-HCl buffer (pH 8.0) containing 1M NaCl, 1 mM EDTA, and 0.1% sodium dodecylsulfate (SDS)) at 42° C. for an hour, respectively, then placed into a bag for hybridization and dipped in a prehybridization solution (50% formamide, 5×Denhardt's solution (0.2% bovine serum albumin, 0.2% polyvinylpyrolidone), 5×SSPE, 0.1% SDS, 100 µg/ml thermally-denatured salmon sperm DNA), followed by prehybridization at 42° C. for 6 to 8 hours. Next, to the prehybridization solution was added the $^{32}P$-labeled probe described in the above (c) which was thermally denatured at 100° C. for 5 min., and hybridization was carried out at 42° C. overnight. After completion of hybridization, the filters were rinsed in a large amount of 2×SSC solution containing 0.1% SDS at room temperature. Next, the filters were placed in a 0.2×SSC solution containing 0.1% SDS at 55° C. for 30 min. After this treatment was repeated twice, the filters were air-dried. Then each filter was put on an X-ray film (Kodak XR) and autoradiography was carried out at −80° C. for 12 hours. The X-ray films were developed. Two films obtained from a single plate were superposed, and overlapping signals were marked. Plaques corresponding to the marked signals were picked up and suspended in an SM solution (50 mM Tris-HCl buffer (pH 7.5) containing 100 mM NaCl and 10 mM $MgSO_4$). This phage suspension was suitably diluted, preferably diluted at a concentration of 10 to 100 plaque forming units/10 $cm^2$ plate, and plated on 10 $cm^2$ plates on which E. coli was cultured. Then screening was carried out in the same manner as above, and recombinant phages were obtained.

(d) Preparation of Recombinant λ gt11 DNA Having Novel MT-MMP-3 Gene

The cloned phages were plated respectively in the same manner as that described in the foregoing (c), and incubated at 42° C. for 3 hours, and then at 37° C. overnight. To the SM solution were added several drops of chloroform, and the plates were allowed to stand at room temperature for 30 min. A plug of soft agar in the upper layer was obtained by scratching together with the SM solution, followed by centrifugation. To the centrifuged supernatant was added polyethylene glycol-6000 (PEG-6000) until a final concentration of 10% was reached, the mixture was stirred, and allowed to stand at 4° C. for 1 hour. This was centrifuged, the supernatant was discarded, and phage particles were recollected. The phage particles were suspended in a SM solution and purified by glycerol-gradient ultracentrifugation (Molecular cloning, a laboratory manual, Ed. T. Maniatis, Cold Spring Harbour Laboratory, 2nd Ed. 78, 1989). The obtained phages were suspended in a TM solution, and treated with DNase I and RNase A, to which then was added a mixture of 20 mM EDTA, 50 µg/ml Proteinase K, and 0.5% SDS. The mixture was incubated for 1 hour at 65° C. The resultant mixture was extracted with phenol, then with diethyl ether, and precipitated with ethanol to afford DNA. The obtained DNA was washed with 70% ethanol, dried, and dissolved in a TE solution (10 mM Tris-HCl buffer (pH 8) containing 10 mM EDTA).

(e) Sequencing of Inserts

The λ gt11 DNA prepared in the foregoing (d) was cleaved with EcoRI. The inserts were separated and purified, then subcloned into the EcoRI site of a vector pBluescript™ (Stratagene). Host cells, E. coli NM533 XL1-Blue, were transformed with this recombinant pBluescript. After selection of the transformed cells, the cells were infected with helper phages, VCSM13 (Stratagene), and cultured overnight. The cultured medium was centrifuged to remove bacterial cells, and PEG/NaCl was added to this medium to precipitate phages. The precipitate was suspended in a TE solution, then extracted with phenol and precipitated with ethanol to recover single strand DNAs. The single strand DNA was sequenced using a fluorescent DNA sequencer Model 373A (Applied Biosystems) and a Taq dyeprimer cycle sequencing kit (Applied Biosystems). The sequenced full-length nucleotide sequence was 2116 base pairs, and described in SEQ ID NO: 1 of the Sequence Listing. For the nucleotide sequence of SEQ ID NO: 1, a matching sequence was checked using GENBANK/EMBL DNA Data Base; however, there exists no same sequence. It has been recognized that an open reading frame potentially encoding a putative 607-amino acid protein is present in this approximately 2.1-kilobase pair DNA sequence, of which amino acid sequence is shown in SEQ ID NO: 2 in the Sequence Listing. The deduced protein has been named "MT-MMP-3". The obtained DNA fragments can be incorporated into vectors including plasmids, such as PEX, pMEMneo, or pKG and can be expressed in host cells such as E. coli or CHO cells.

The Escherichia coli, designated NM533 XL1-Blue (XL1-Blue/MMP-X2), harboring a vector (p SG5™ (Stratagene)) into which a nucleotide sequence coding for the above MT-MMP-3 is incorporated has been deposited as from Jul. 5, 1995 (original deposit date) with NIBH and has been assigned the Accession Number FERM P-15033. The original deposit of the transformant E. coli NM533 XL1-Blue (XL1-Blue/MMP-X2) has been transferred to one under the Budapest Treaty by a request dated Jul. 1, 1996 and is on deposit with the Accession Number FERM BP-5573 under the terms of the Budapest Treaty at NIBH.

(f) Amino Acid Sequence Analysis of MT-MMP-3

FIGS. 1A to 1E show an alignment when the amino acid sequence (described in SEQ ID NO: 2 in Sequence Listing) deduced from the MT-MMP-3 nucleotide sequence (described in SEQ ID NO: 1 in Sequence Listing) is compared with the known amino acid sequences of MMP members. The amino acid sequence as shown in SEQ ID NO: 2 in Sequence Listing shows high homology to the MMP family, and conserves well characteristic domain structures of the MMP family, i.e., a signal peptide removable during secretion and production, a propeptide domain, a catalytic domain, a hinge domain, and a hemopexin-like domain. In particular, PRCGVPD (SEQ ID NO: 12), which is the most conservative sequence among the MMP family members and positioned at or near a cleavage site for converting a pro form into an active form, is conserved completely in MT-MMP-3, and the sequence of an active domain is also highly conservative. Comparison of MT-MMP-3 with the other known MMP family members for the amino acid sequences of the active domain including a $Zn^{2+}$-binding site, reveals that the homology of MT-MMP-3 protein is the highest to MT-MMP-1 (68%) and significantly to others, including MMP-12 (49%), MMP-2 (52%), MMP-9 (48%, ), MMP-1 (49%), MMP-3 (48%), MMP-8 (49%), MMP-11 (42%), and MMP-7 (44%).

In addition, MT-MMP-3 has three characteristic insertions compared with the other MMP family members. They are the 11-amino acid insertion, GSSKFHIRRKR (IS-1: $Gly^{109}$ to $Arg^{119}$ of SEQ ID NO: 2), between a propeplide domain and a catalytic domain, the 8-amino acid insertion, PYSELENG (TS-2: $Pro^{171}$ to $Gly^{178}$ of SEQ ID NO: 2), in the catalytic domain, and the 75-amino acid insertion (IS-3: $Asp^{538}$ to $Val^{607}$ of SEQ ID NO: 2) containing the continuous transmembrane-like 24-hydrophobic amino acid sequence, AIAIVIPCILALCLLVLVYTVFQF(SEQ ID NO: 13). Such three insertion sequences are present only in MT-MMP-1 among the MMP family members but not recognized in the other MMPs. With regard to three insertion sequences in MT-MMP-3, the number and position of constituting amino acid residues thereof is almost same as in MT-MMP-1; however, the amino acid composition thereof is clearly different from that of MT-MMP-1, and IS-3 has 37% homology to that in MT-MMP-1. Incidentally, the homology of entire sequences is 53%. A similar sequence to the first insertion IS-1 is exceptionally present in MMP-11; however, the RXKR (SEQ ID NO: 14) sequence conserved in IS-1 is a potential processing region for subtilisin-like enzymes, and it is known that the amino acid sequence RXKR (SEQ ID NO: 14) is the subtilisin-like protease-cleavage site of various eucaryotic secretory proteins (J. Biol. Chem., 266: 12127 to 12130, 1991). The continuous sequence composed of hydrophobic amino acids in IS-3 is believed to be a transmembrane (TM) domain (TM is specifically characteristic of MT-MMP-1 (J. Biol. Chem.: 270, 801 to 805, 1995)). Thus, the continuous sequence of hydrophobic amino acids existing in IS-3 of MT-MMP-3 is also expected to be a transmembrane domain (see: Example 5). The amino acid sequence encoded by MT-MMP-3cDNA isolated according to the present invention is highly homologous to the other MMP family and is similar to MT-MMP-1 previously discovered by the present inventors; however, it is obviously different in the detailed points and differed in molecule weight. The protein of the present invention has a molecule weight of approximately 69 kDa.

These features on the sequences suggest that MT-MMP-1 and MT-MMP-3 form a sub-family in the MMP family.

Example 2

Expression of MT-MMP-3 mRNA (a) Expression in Human Tissues

Northern blotting was carried out by using the membrane, Human Multiple Tissue Northern Blots (Clontech) onto which poly (A)+RNA samples derived from human tissues such as heart, brain, placenta, lung, liver, skeletal muscle, kidney, and pancreas were applied and by using as a probe the $^{32}$P-labeled 2.1 kb cDNA as described in Example 1 (e). Labeling of the probe was done in the same manner as in Example 1 (c). Multiple Tissue Northern Blots filters wetted with 3×SSC (0.45 M NaCl, 0.045 M trisodium citrate $2H_2O$, pH7.0) were dipped in 10 ml of pre-hybridization solution (0.75M NaCl, 2.5 mM EDTA, 0.5×Denhardt's solution, 50% formamide, and 20 mM Tris-HCl buffer (pH 7.5) containing 1% SDS). Pre-hybridization was carried out at 42° C. for two or three hours with gentle stirring. Next, the pre-hybridization solution was exchanged with a solution obtained by addition of heat-denatured probes to 10 ml of hybridization solution (in which 10% sodium dextran and 20u g/ml denatured salmon sperm DNA were added to a pre-hybridization solution). Hybridization was carried out at 43° C. overnight. After completion of hybridization, the filters were washed with a 2×SSC solution containing 0.1% SDS.

Next, the blots were placed in a 1×SSC solution containing 0.1% SDS at 55° C. for 30 min. The blots were traced with a Bioimage Analyzer BAS1000 (Fuji Photo Film Co., Ltd.), and expression intensities of mRNAs in each tissue was assessed. At this time, the same blots were probed with $^{32}$P-labeled glyceraldehyde-3-phosphate dehydrogenase (GAPDH) gene (CLONTECH) for using as a mRNA internal standard.

The results are shown in FIG. 2A. The size of MT-MMP-3 mRNA is 12 kb in any tissue. Among the tissues examined, a band specific MT-MMP-3 cDNA probe was detected in lung, brain, and placenta, with high expression; however, it was undetectable in the heart, kidney, liver, pancreas, and skeletal muscle.

On the other hand, when northern blotting was carried out by using Human Multiple Tissue Northern Blots (Clontech), and using as a probe $^{32}$P-labeled MT-MMP-1 cDNA, MT-MMP-1mRNA detected at 4.5 kb was significantly expressed in lung, kidney, and placenta. The lowest expression occurred in the brain. Cross-hybridization of MT-MMP-1 and MT-MMP-3 was not generated.

(b) Expression in Cultured Tumor Cells

The expression of MT-MMP-3 mRNA in various cultured human tumor cell lines was examined. The human tumor cell lines used were larynx carcinoma-derived Hep2 cell, bladder carcinoma-derived T24 cell, lung carcinoma-derived PC-3 cell, stomach tumor-derived cells KKLS, NKPS, and MKN-28, osteosarcoma-derived cells SK-ES-1 and U-20S, squamous cell carcinoma-derived OSC-19, and malignant melanoma A375 cell. The fibroblasts used were human embryonal lung-derived fibroblasts HEL.

RNA samples extracted from each cells (10 µg per sample) were dissolved in 2% MOPS (pH 7.5) containing 50% formamide and 17.5% formalin and reacted at 65° C. for 10 min. The products were applied to 1% agarose gel electrophoresis in 2% MOPS. After electrophoresis, the gel was transferred onto a nylon membrane (for example, Hybond-N, Amersham). After the transfer, the membrane was fixed by irradiating ultraviolet rays with 254 nm in wavelength by 1200 micro Joule. The blots were hybridized with $^{32}$P-labeled cDNA for 16 hours in the same manner as in the foregoing (a), and were traced with a Bioimage Analyzer BAS1000 (Fuji Photo Film Co., Ltd.). Signals were detected and their intensity was assessed.

MT-MMP-3 mRNA was detected in bladder carcinoma T24 and larynx carcinoma Hep2 cells with higher expression than in the other cells. However, the expression of MT-MMP-1 mRNA was at low levels in these cells.

On the other hand, in OSC-19 cells and HEL cells in which the significant expression of MT-MMP-1 mRNA was detected, the expression level of MT-MMP-3 mRNA was lower than in other cells (FIG. 2B).

Although MT-MMP-1 and MT-MMP-3 have, from the comparison of the amino acid sequences, a quite similar domain structure and have the same action on activating pro MMP-2 (see: Example 6), expression of the genes for MT-MMP-1 and MT-MMP-3 shows a completely different pattern in the tissues or cell level. This shows that MT-MMP-1 and MT-MMP-3 are subject to different expression controls although they have the similar structure and function.

Example 3

Preparation of Monoclonal Antibodies (a) Preparation of Antigen Polypeptides

For sequences specific to MT-MMP-3 in which their homology to the other MMP family is low, the following four sequences were selected from the amino acid sequence of MT-MMP-3 as described in SEQ ID NO: 2 in the Sequence Listing, and synthesized:

(SEQ ID NO: 5)

QTRGSSKFHIRRKR (corresponding to Sequence: Gln$^{106}$ to Arg$^{119}$ of SEQ ID NO: 2; abbreviated as "polypeptide A")
(SEQ ID NO: 6)

EEVPYSELENGKRD (corresponding to Sequence: Glu$^{168}$ to Asp$^{181}$ of SEQ ID NO: 2; abbreviated as "polypeptide B")
(SEQ ID NO: 7)

PTSPRMSVVRSAETMQSA (corresponding to Sequence: Pro$^{55}$ to Ala$^{72}$ of SEQ ID NO: 2; abbreviated as "polypeptide C")
(SEQ ID NO: 8)

TLGNPNHDGNDLFL (corresponding to Sequence: Thr$^{229}$ to Leu$^{242}$ of SEQ ID NO: 2; abbreviated as "polypeptide D").

These peptides were synthesized using a peptide synthesizer (peptide synthesizer 9600, MilliGen/Bipserch) with Fmoc-bop techniques. Cysteine was introduced on the N-terminus of each polypeptide. The synthetic peptides were purified with high performance liquid chromatography using µ Bondasphere, C18 column (Waters).

(b) Preparation of Polypeptide-BSA Conjugates

Each peptide was coupled with bovine serum albumin (BSA) via a cysteine residue to form an antigen-conjugate. BSA (20 mg) was dissolved in 2 ml of 0.1 M phosphate buffer, pH 7.5. Also, 18.13 mg of N-(6-maleimidocaproyloxy)-succinimide was dissolved in 200 µl of dimethylformamide. A mixture of the BSA solution and the N-(6-maleimido-caproyloxy)succinimide solution was reacted at 30° C. for 30 min., and then subjected to gel filtration through PD-10 (Pharmacia) equilibrated with a 0.1 M phosphate buffer, pH 7.0. Maleimido-coupled BSA fractions were collected and concentrated to 1.5 ml or less. Each synthetic polypeptide obtained in the above (a) (molar ratio of polypeptide: maleimido-coupled BSA=50: 1) was dissolved in 1 ml of 0.1 M phosphate buffer, pH 7.0, then mixed with the maleimido-coupled BSA thus prepared. The mixture was incubated at 4° C. for 20 hours to form a BSA-polypeptide conjugate.

(c) Preparation of Antibody-Producing Cells

An eight-week old female Balb/c mouse was primarily immunized by administering intraperitoneally 200 µg of each BSA-polypeptide conjugate (conjugate of BSA with any of four polypeptides A, B, C, and D, prepared in the above (b) step) together with complete Freund's adjuvants. Eighteen days later, 200 µg of each BSA-polypeptide conjugate dissolved in a 0.1 M phosphate buffer, pH7.5, was administered intraperitoneally to the primarily immunized mouse for additional immunization. Further 32 days later, 100 µg of each BSA-polypeptide conjugate was administered intraperitoneally to the mouse for final immunization in the similar manner to that during additional immunization. Next three days later, the spleen was taken out, and the spleen cell suspension was prepared.

(d) Cell Fusion (1) The following materials and methods were used:
RPMI-1640 medium:
To RPMI-1640 (Flow Lab.) were added sodium bicarbonate (24 mM), sodium pyruvate (1 mM), penicillin G potassium (50 U/ml), amikacin sulfate (100 µg/ml), and the mixture was adjusted pH to 7.2 with dry ice, sterilized and filtered through a 0.2 µm Toyo Membrane Filter.

NS-1 medium:
To the above RPMI-1640 medium was added sterilized and filtered FCS (M. A. Bioproducts) until a concentration of FCS reached 15% (v/v).

PEG 4000 solution:
To RPMI-1640 medium was added polyethylene glycol 4000 (PEG 4000, Merck & Co.) until a concentration of PEG 4000 reached 50% (w/w). Thus, the serum-free solution was prepared.

Cell fusion using 8-azaguanine-resistant myeloma SP2 cells (SP2/0-Ag14) was carried out by slightly modified methods according to Oi, et al. techniques disclosed in "Selected Method in Cellular Immunology pp.351 to 372 (ed. B. B. Mishell and S. N. Shiigi), W. H. Freeman and Company (1980)".

(2) Described below is cell fusion between murine nucleated spleen cells immunized with polypeptide A-BSA conjugates and myeloma SP2 cells.

The respective nucleated spleen cells (viable cell rate: 100%) prepared in the foregoing (c) were fused with myeloma cells (viable cell rate: 100%) in a ratio of 5:1 according to the following procedure:

The polypeptide A-immunized spleen cell suspension and the myeloma cells were washed respectively with a RPMI 1640 medium followed by resuspending in the same medium. For fusion, 1.1×10$^9$ nucleated spleen cells and 2.1×10$^8$ myeloma cells were mixed together. The cell suspension was pelleted by centrifugation and the supernatant fluid was completely aspirated off. To the cell pellet was added 7.1 ml of PEG 4000 solution (RPMI 1640 medium containing 50% (w/v) polyethylene glycol 4000) pre-warmed to 37° C. dropwise for 1 min., and stirred for 1 min. to allow the cells to be resuspended and dispersed. Next, after 14.2 ml of 37° C. pre-warmed RPMI 1640 medium was added dropwise for 2 min., 49.7 ml of the same medium was added dropwise within 2 to 3 min. with stirring to allow the cells to be dispersed. This cell dispersion was centrifuged, and the supernatant fluid was completely aspirated off. To the cell pellet was added 71 ml of 37° C. pre-warmed NS-1 medium (RPMI 1640 medium supplemented with filtered sterile 15% (w/v) fetal calf serum (JRH Bioscience)) quickly, and a large cell mass was carefully dispersed by pipetting. Next, the cell suspension was diluted with 142 ml of the same medium, and 6.0×10$^5$ cells/0.1 ml was plated on each well of a polystyrene 96-well microtiter tray. The cell-containing microwell was incubated at 37° C. under a 100% humidified atmosphere containing 7% CO$_2$/93% air.

For mouse-derived spleen cells immunized with the polypeptide B-BSA conjugate, the spleen cells (6.2×10$^8$ cells) were mixed with 1.24×10$^8$ myeloma cells, and PEG 4000 solution, RPMI 1640 medium, and NS-1 medium as used above were used by 4.1 ml, 36.9 ml, and 123 ml, respectively.

For mouse-derived spleen cells immunized with the polypeptide C-BSA conjugate, the spleen cells (3.6×10$^8$ cells) were mixed with 7.5×10$^7$ myeloma cells, and PEG 4000 solution, RPMI 1640 medium, and NS-1 medium were used by 2.5 ml, 22.5 ml, and 75 ml, respectively.

For mouse-derived spleen cells immunized with the polypeptide D-BSA conjugate, the spleen cells (6.0×10$^8$ cells) were mixed with 1.2×10$^8$ myeloma cells, and PEG 4000 solution, RPMI 1640 medium, and NS-1 medium were used by 4.0 ml, 36.0 ml, and 120 ml, respectively.

(e) Selective Growth of Hybridomas in Selection Medium (1) Media to be used were as follows:

HAT medium: To NS-1 medium as described in foregoing (d) (1) was added further hypoxanthine (100 µM), aminopterin (0.4 µM), and thymidine (16 µM).

HT medium: The medium has the same composition as the foregoing HAT medium except that aminopterin was excluded.

(2) Next day (first day) from culture initiation of the foregoing (d), two drops of HAT medium (approximately 0.1 ml) was added to the cells with a Pasteur pipette.

On the 2nd, 3rd, 5th, and 8th days, a half of the medium (approximately 0.1 ml) was replaced with fresh HAT medium, respectively. On the 11th day, a half of the medium was replaced with fresh HT medium. On the 14th day, positive wells were examined by solid phase-antibody binding test (enzyme-linked immunosorbent assay; ELISA) for all wells wherein the growth of hybridomas was visually recognized.

Polystyrene 96-well plates were coated with polypeptides A, B, C, and D, respectively, used as an antigen, and washed with PBS (containing 0.05% Tween 20) for washing to remove unadsorbed peptides. Next, the uncoated portions of each well were blocked with 1% BSA. To each polypeptide-coated well was added 0.1 ml of supernatant fluid from the hybridoma well in which hybridomas were grown and the polypeptide-coated well was allowed to stand at room temperature for approximately one hour. To the polypeptide-coated well was added, as a second antibody, horseradish peroxidase (HRP)-labeled goat anti-mouse immunoglobulin (Cappel Lab.), and the well was further allowed to stand at room temperature for approximately 1 hour. Next, to the well was added substrates, hydrogen peroxide and o-phenylenediamine, and OD readings at 492 nm were obtained by a microplate OD reader (MRP-A4, Toso, Japan).

(f) Cloning of Hybridomas

Hybridomas in the well positive against each antigen peptide obtained in the foregoing (e) were cloned by limiting dilution to establish monoclones.

That is, a cloning medium containing, as feeder cells, $10^7$ mouse thymocytes per 1 ml of NS-1 medium was prepared. Into a 96-well microtiter tray was plated hybridomas at a cell density of 5, 1, or 0.5 cells per well, respectively, with dilutions wherein the 5, 1, or 0.5 hybridoma cells per well was plated to 36, 36, and 24 wells, respectively. On the 5th and 12th days, about 0.1 ml of NS-1 medium was added to all the wells. Approximately two weeks later from the initiation of cloning, ELISA as described in the above (e) was conducted for groups wherein the sufficient growth of hybridomas was visually recognized and the rate of colony formation-negative wells is 50% or more. In cases where all the examined wells were negative, 4 to 6 wells each containing 1 colony were selected from antibody-positive wells, and recloned. Finally, as shown in Tables 1 to 4, 7 anti-polypeptide A antibody-producing, 16 anti-polypeptide B antibody-producing, 11 anti-polypeptide C antibody-producing, and 4 anti-polypeptide D antibody-producing hybridoma cells were obtained, respectively.

(g) Cultivation of hybridomas and Purification of Monoclonal Antibodies

Each hybridoma cell thus obtained was cultured in NS-1 medium to afford monoclonal antibodies with a concentration of 10 to 100 µg/ml in the culture supernatant. Further, $10^7$ hybridoma cells thus obtained were administered intraperitoneally to a mouse (inbred BALB/c mouse, ♀, six-week old) intraperitoneally primed with pristane 1 week prior to injection, and one or two weeks later an ascitic fluid containing 4 to 7 mg/ml monoclonal antibody was recollected. The obtained ascitic fluids were salted out with 40% ammonium sulfate saturation, IgG class antibodies were adsorbed on protein A affigel (Bio-Rad), followed by elution with a 0.1 M citrate buffer (pH 5) to afford purified forms.

(h) Determination of Class and Sub-class for Monoclonal Antibody

To microtiter plates on which polypeptides A, B, C, and D were coated according to ELISA as described herein above, was added each supernatant obtained in the above (f). Next, after PBS washing, iso-type specific rabbit anti-mouse IgG antibodies (Zymed Lab.) was added. After PBS washing, horseradish peroxidase-labeled goat anti-rabbit IgG (H+L) was added, and visualization was carried out with hydrogen peroxide and 2,2'-azinodi(3-ethylbenzothiazolinic acid). As a result, the class and sub-class were determined. Finally, as shown in Tables 1 to 4, plural monoclonal anti-MT-MMP-3 antibody-producing hybridomas were obtained.

TABLE 1

| Polypeptide | Clone No. | Subclass/Chain |
| --- | --- | --- |
| A | 116-1E7 | γ 1/κ |
|  | 116-2G6 | γ 1/κ |
|  | 116-6A11 | γ 1/κ |
|  | 116-7B2 | µ/κ |
|  | 116-10E10 | µ/κ |
|  | 116-11B2 | µ/κ |
|  | 116-12E3 | µ/κ |

TABLE 2

| Polypeptide | Clone No. | Subclass/Chain |
| --- | --- | --- |
| B | 117-1F6 | γ 1/κ |
|  | 117-2H5 | γ 1/κ |
|  | 117-3B9 | γ 1/κ |
|  | 117-4E1 | γ 1/κ |
|  | 117-5A6 | γ 1/κ |
|  | 117-6C11 | γ 1/κ |
|  | 117-9H5 | γ 1/κ |
|  | 117-10C6 | γ 1/κ |
|  | 117-13B6 | γ 2a/κ |
|  | 117-14E3 | γ 1/κ |
|  | 117-15C5 | γ 1/κ |
|  | 117-16E10 | γ 1/κ |
|  | 117-17E10 | γ 2b/κ |
|  | 117-18D9 | γ 1/κ |
|  | 117-19D1 | γ 1/κ |
|  | 117-20B3 | γ 1/κ |

TABLE 3

| Polypeptide | Clone No. | Subclass/Chain |
| --- | --- | --- |
| C | 157-3G4 | γ 1/κ |
|  | 157-4A5 | γ 2b/κ |
|  | 157-6F5 | γ 1/κ |
|  | 157-11E1 | µ/κ |

TABLE 4

| Polypeptide | Clone No. | Subclass/Chain |
| --- | --- | --- |
| D | 158-2D6 | γ 2a/κ |
|  | 158-3E12 | γ 2a/κ |
|  | 158-8E6 | γ 1/κ |

TABLE 4-continued

| Polypeptide | Clone No. | Subclass/Chain |
|---|---|---|
| | 158-9F6 | γ 2b/κ |
| | 158-11D10 | μ/κ |
| | 158-16F12 | γ 1/κ |
| | 158-17F1 | γ 1/κ |
| | 158-18D8 | γ 1/κ |
| | 158-19F10 | γ 1/κ |
| | 158-20D5 | γ 2a/κ |
| | 158-21F11 | γ 1/κ |

The clone No. 117-4 E1 has been deposited as from Jul. 5, 1995 (original deposit date) with NIBH and has been assigned the Accession Number FERM P-15031. The original deposit of the hybridoma 117-4E1 has been transferred to one under the Budapest Treaty by a request dated Jul. 1, 1996 and is on deposit with the Accession Number FERM BP-5572 under the terms of the Budapest Treaty at NIBH.

(i) Specificity of Anti-MT-MMP-3 Monoclonal Antibody

The cross-reactivity of each monoclonal anti-MT-MMP-3 antibodies (clone Nos. 117-4E1, 157-6F5 and 158-8E6) wherein each antibody positively reacts with a human MT-MMP-3 peptide was examined by solid phase-antibody binding tests (ELISA), as described in the above (e), using as an antigen pro MMP-1 (Clin. Chim. Acta, 219: 1 to 14, 1993), pro MMP-2 (Clin. Chim. Acta, 221: 91 to 103, 1993), and pro MMP-3 (Clin. Chim. Acta, 211: 59 to 72, 1992), purified from the culture supernatant of human embryonal fibroblasts (NB1RGB), respectively; pro MMP-7 purified from the culture supernatant of human rectal carcinomas (CaR-1) (Cancer Res., 50: 7758 to 7764, 1990); pro MMP-8 from human neutrophiles (Biol. Chem. Hoppe-Seyler, 371: Supplement, 295 to 304, 1990); or pro MMP-9 from the culture supernatant of human fibrosarcomas (HT1080) (J. Biol. Chem., 267: 21712 to 21719, 1992), respectively.

That is, polystyrene 96-well plates were used. Purified MMP-1, MMP-2, MMP-3, MMP-7, MMP-8, and MMP-9 were added in 50 ng/well to each well, respectively, to coat the well. After the wells were washed with PBS for washing to remove unadsorbed antigens, uncoated portions of each well were blocked with PBS containing 3% skim milk. To each well was added each anti-MT-MMP monoclonal antibody with 1 μg/well, and the well was allowed to stand at room temperature for approximately 1 hour. After the plates were washed, peroxidase-labeled goat anti-mouse immunoglobulin was added as a second antibody and further was reacted at room temperature for approximately 1 hour. Next, substrates, hydrogen peroxide and o-phenylenediamine, were added, and optical density (OD) readings at 492 nm were obtained by a microplate OD reader (MRP-A4, Toso, Japan).

As a result, none of the anti-MT-MMP-3 monoclonal antibodies had reactivity with purified MMPs samples, other than MT-MMP-3.

The methods as described in Example 3 are repeated, by using, as an antigen, recombinant MT-MMP-3, for example, recombinant MT-MMP-3 obtained in Examples 4 and 5 described herein below, instead of the synthetic peptide antigen, to produce monoclonal anti-MT-MMP-3 antibodies similarly.

Example 4

Expression and Identification of Gene Products

To express MT-MMP-3 in animal cells as hosts, cDNA was ligated with an expression vector.

In this Example, pSG5 (Stratagene) containing the SV40 promoter, enhancer, poly A signal, small T antigen gene intervening sequence was used for the expression vector. The recombinant pBluescript™ (Stratagene) wherein cloned MT-MMP-3 gene was integrated and which were constructed in Example 1 (e) was cleaved with EcoRI to produce 2.1 kb insertion fragments which were inserted into the EcoRI site of eukaryotic expression vector pSG5 to form expression plasmid pSGMT2. Ligation was carried out in accordance with the protocols attached with ligation kits. African green monkey kidney-derived COS-1 cells were cultured in Dulbecco's modified Eagle's medium (DMEM) supplemented with 5% fetal calf serum and 2 mM glutamine. The cultured COS-1 cells were cotransfected with pSGMT2 and pSGT1 (TIMP-1 cDNA was cloned in pSG5) according to calcium phosphate techniques (Virology, 52: 456, 1973). For a control, COS-1 was transfected with pSG5 alone.

That is, to distilled water was added 2 μg of recombinant pSG5 or pSG5 alone, to which 60 μl of 0.25 M $CaCl_2$ was added. Then 62.5 μl of 2×BBS solution (50 mM BES buffer (pH7.9) containing 2.8 mM $Na_2HPO_4$ and 280 mM NaCl) was added to the bottom of the tube. After mixing, the mixture was allowed to stand at room temperature for 30 minutes, until sufficient precipitation occurred. After the precipitates were dispersed by pipetting and added dropwise to COS-1 cells, the resultant cells were incubated in a $CO_2$ incubator for approximately 24 hours. Then the medium was removed, the cells were washed with PBS, followed by addition of fresh methionine-free DMEM supplemented with 30 μCi/ml $^{35}$S-methionine. The cultivation was continued for 5 hours to label cell proteins with $^{35}$S. The cells and condition medium were separated by centrifugation, and the cells were incubated at 4° C. for 1 hour in a lysis buffer solution (10 mM Tris-HCl buffer, pH7.5, containing 0.15 M NaCl, 0.1% sodium deoxycholate, 0.1% SDS, 1 mM Triton X-100, 1% NP-40, 1 mM EDTA, 1 mM phenylmethanesulfonyl fluoride (PMSF)). The cell lysates were centrifuged to recollect supernatants. Both the cell lysate supernatants and conditioned medium were reacted with anti-MT-MMP-3 polypeptide antibody clones Nos. 117-4E1 or 117-13B6 (obtained in Example 3), and for a control with anti-TIMP-1 antibody clone No. 50-1H7 at 4° C. for 16 hours. Clone Nos. 117-4E1 or 117-13B6 antibody were selected because they have low non-specific reactivity among the anti-MT-MMP-3 monoclonal antibodies. To these antigen-antibody complexes was added protein A-coupled Sepharose™-4B (Pharmacia) and the mixture was incubated at 4° C. for 2 hours with stirring to carry out immunoprecipitation. Then, the Sepharose™-4B coupled with immunoprecipitated monoclonal antibodies was precipitated by centrifugation, and washed three times with a lysis buffer solution, and finally with a 0.05 M Tris-HCl buffer solution, pH6.8. To this washed Sepharose™-4B was added a SDS polyacrylamide electrophoresis sample buffer solution (50 mM Tris-HCl buffer (pH 6.5) containing 10% glycerol, 2% SDS, 2% β-mercaptoethanol, 0.1% bromophenol blue) and the mixture was heated at 100° C. for 3 min., and then applied to 12% SDS polyacrylamide electropl horesis. After electrophoresis, the gel was detected using a Bioimage Analyzer BAS1000 (Fuji Photo Film Co,. Ltd.).

The results are shown in FIG. 3.

Both anti-MT-MMP-3 polypeptide mAbs 117-4E1 and 117-13B6 used were precipitated immunologically a 64-kDa protein specifically from the lysate of cells transfected with MT-MMP-3 genes. Neither of the mAbs was precipitated from that of cells transfected the control vector pSG5 wherein no MT-MMP-3 gene was included. The molecular size 64 kDa of the proteins detected in immunoprecipitation almost matched the molecule weight calculated from the amino acid sequence of SEQ ID NO: 2 in Sequence Listing.

In addition, three bands equivalent to molecular sizes 30, 33, and 52 kDa were detected only from cell lysates of cells transfected with MT-MMP-3 genes. However, none of these bands were detected in the control.

On the other hand, none of these proteins as immunoprecipitated from cell lysates were detected from the conditioned culture medium. To the contrary, TIMP-1 was a secretory protein. In fact, most of the expressed TIMP-1 was detected in the conditioned culture medium and it was confirmed that TIMP-1 was surely secreted outside the cells.

The foregoing results show that MT-MMP-3 is not easily secreted though the presence of a signal peptide is suggested from its amino acid sequence. This finding is very similar to the previous finding obtained by the present inventors in which MT-MMP-1 was expressed on the cell surface layer, but was not detected in the culture medium (Nature, 370; 61 to 65, 1994).

Since MT-MMP-3 cDNA is a full-length cDNA synthesized with reverse-transcriptase from mRNA, MT-MMP-3 can be mass-produced via transferring this cDNA to a suitable expression vector wherein *E. coli, bacillus subtilis*, yeasts, animal cells or the like are used as a host. In the Example in which pSGMT2 was introduced into COS-1, MT-MMP-3 is transiently expressed in the transformant COS-1; however, cell strains capable of producing the targets for a long period can be obtained using expression vectors having a suitable selection marker (for example, neo genes, dehydrofolate reductase genes, etc.) and introducing it into CHO cells or the like.

Example 5

Function of the C-terminal Hydrophobic Amino Acid Continuous Sequence of MT-MMP-3

(a) Preparation of Chimeric Protein (TIMP/MT-3) between MT-MMP-3 C-Terminal Hydrophobic Amino Acid Continuous Sequence and TIMP-1 and of Chimeric Protein (TIMP/MT-1) between MT-MMP-1 C-Terminal Hydrophobic Amino Acid Continuous Sequence and TIMP-1

Preparation of chimeric proteins between MT-MMP C-terminal hydrophobic amino acid continuous sequence and TIMP-1 was carried out according to techniques for preparation of chimeric proteins between MT-MMP-1 transmembrane domain and TIMP-1 in Cao, et al. (J. Biol. Chem. 13; 801 to 805, 1995).

cDNA fragments encoding the the amino acid sequence ($Ala^{559}$ to $Val^{607}$) containing MT-MMP-3 C-terminal hydrophobic amino acid sequence were amplified by PCR techniques and recollected. Similarly, cDNA fragments encoding the the amino acid sequence ($Gly^{535}$ to $Val^{582}$) containing MT-MMP-1 C-terminal hydrophobic amino acid continuous sequence were amplified by PCR and recollected. PCR amplification was carried out in the similar manner to that in Example 1 (b).

Each DNA fragment thus obtained was ligated into the 3'-terminal side of TIMP-1 cDNA, and subjected to subcloning to pSG5. Thus, expression plasmid pSGTlM2 for TIMP-1/MT-3 chimeric protein was produced. Similarly, expression plasmid pSGTlM1 for TIMP-1/MT-1 chimeric protein was produced. Ligation was carried out in accordance with the protocols accompanying with the ligation kit.

Transfection of these plasmids into COS-1 was carried out in the similar manner to that described in Example 4. COS-1 cells cultured in DMEM supplemented with 5% fetal calf serum and 2 mM glutamine were transfected with pSGTlM2, pSGTlM1, and pSGT1, respectively, by the calcium phosphate technique. As a control, COS-1 was transfected with pSG5 alone.

That is, to 2 µg of plasmid DNA was added 60 µl of 0.25 M $CaCl_2$. Then 62.5 µl of 2×BBS solution (50 mM BES buffer, pH7.9 containing 2.8 mM $Na_2UPO_4$ and 280 mM NaCl) into the bottom of the tube. After mixing, the mixture was allowed to stand at room temperature for approximately 30 min to form precipitates sufficiently. The precipitates were dispersed by pipetting and added dropwise to COS-1 cells, and then the mixture was incubated in a $CO_2$ incubator for approximately 24 hours. After removal of the medium, the cells were washed with PBS, to which then fresh methionine-free DMEM containing $^{35}$S-methionine was added. The cultivation was continued for 5 hours to label cell proteins with $^{35}$S.

The cells and the conditioned culture medium were from each other by centrifugation, and the cells were incubated at 4° C. for 1 hour in a lysis buffer solution (10 mM Tris-HCl buffer, pH 7.5 containing 0.15 M NaCl, 0.1% sodium deoxycholate, 0.1% SDS, 1 mM Triton X-100, 1% NP-40, 1 mM EDTA, and 1 mM PMSF), and supernatants were collected. The lysed cell supernatants and the conditioned culture medium were reacted with anti-TIMP-1 antibody, clone No. 50-1H7 (obtained in Example 3), at 4 ° C. for 16 hours.

To the antigen-antibody complexes thus obtained was added a protein A-coupled Sepharose™-4B (Pharmacia) and the mixture was incubated with stirring at 4° C. for 2 hours to carry out immunoprecipitation. The immunoprecipitated Sepharose™-4B coupled with the monoclonal antibody was precipitated by centrifugation, the precipitate was washed 3 times with a lysis solution, and then finally washed with 0.05 M Tris-HCl buffer, pH 6.8. To this washed Sepharose™-4B was added an SDS polyacrylamide electrophoresis sample buffer solution (50 mM Tris-HCl buffer, pH 6.5 containing 10% glycerol, 2% SDS, 2% β-mercaptoethanol, 0.1% bromophenol blue) and the mixture was heated at 100° C. for 3 min., and then applied to 12% SDS polyacrylamide gel electrophoresis. After the electrophoresis, signals of the gel were detected by a Bioimage Analyzer-BAS1000 (Fuji Photo Film Co., Ltd.).

TIMP-1, TIMP-1/MT-1, and TIMP-1/MT-3 were detected as 28, 32, and 32 kDa proteins in the cell lysate, respectively. The molecule sizes of the detected chimeric proteins TIMP-1/MT-1 and TIMP-1/MT-3 matched the molecule weights estimated from the construct of the fused genes. TIMP-1 was predominantly detected in the conditioned culture medium, though it was found in the cell lysate. However, TIMP-1/MT-1 was detected exclusively in the cell lysate, but not in the conditioned culture medium (J. Biol. Chem., 13; 801 to 805, 1995). TIMP-1/MT-3 was detected exclusively from the cell lysate, similar to TIMP-1/MT-1. The localization of TIMP-1/MT-3 was exactly the same as that of TIMP-1/MT-1 (FIG. 4).

These results show that the hydrophobic amino acid continuous sequence at the MT-MMP-3 C-terminal region suppresses secretion of the fusion proteins to the outside of the cells with a function similar to the hydrophobic amino acid continuous sequence at the MT-MMP-1 C-terminal region.

(b) Expression of Chimeric Proteins in Cell Surface Layers

It was examined whether in fact the hydrophobic amino acid continuous sequence in the MT-MMP-3 C-terminal region is functioning as a transmembrane domain by indirect immunofluorescence staining for TIMP-1/MT-3 expression cells. COS-1 cells were transfected with pSGT1 or pSGTlM2 by the calcium phosphate technique in the similar manner to that described in Example 4. In this Example, the cells were cultured on a slide chamber without using an isotope-labeled medium. After 24-hour culturing, the cells were reacted at 37° C. for 40 minutes in PBS containing 5 µg / ml anti-TIMP-1 antibody, clone No. 50-1H7, and 3% BSA. Then the cells were washed three times with PBS containing 3% BSA, air-dried, and fixed with acetone for 5 min. The cells were soaked in PBS containing 3% BSA, and then reacted with 1500×diluted fluorescein isothiocyanate (FITC)-conjugated goat anti-(mouse IgG) IgG (Capel) at 37° C. for 30 min. Then an excessive amount of antibodies was washed out with PBS containing 3% BSA. Finally, the specimens were overlaid with glycerin and observed under a immunofluorescence microscope.

As a result, in pSGTlM2-expressing cells (chimeric protein TIMP-1/MT-3-producing cells), fluorescence was observed on the cell surface, confirming that the TIMP-1 portion of the chimeric protein was expressed on the cell surface layer. On the other hand, no fluorescence was observed in pSGT1-expressing cells (non-chimeric TIMP-1-producing cells), and the expression of TIMP-1 was not observed on the cell surface layer (FIG. 5).

This result shows that the MT-MMP-3 C-terminal hydrophobic amino acid continuous sequence is functioning as a transmembrane (TM) domain.

Example 6

Activation of Pro MMP-2 due to Expression of MT-MMP-3

COS-1 cells were cotransfected with plasmid pSG5M2 for MT-MMP-3 cDNA as constructed in Example 4, plasmid pSG5M1 for MT-MMP-1 CDNA, or vector pSG5, respectively, together with plasmid pSGGA for pro MMP-2, by the calcium phosphate technique as described in Example 4. In the experiments, a conventional fresh medium was used instead of a fresh medium containing $^{35}$S-methionine. In addition, human fibrosarcoma HT-1080 cell lines were cotransfected with PSGT1, pSGT2, or pSG5,. respectively, together with pSGM2. In the immunoprecipitation experiments, it was confirmed that transformed HT-1080 cell lines secret pro MMP-2 and pro MMP-9 constitutively (corresponding to 68 kDa and 97.4 kDa bands, respectively, in FIG. 6), and MT-MMP-3 cDNA-transfected cells express MT-MMP-3 (see: Example 4).

The transfectants thus obtained were cultured for 24 hours in serum-free DMEM, and the recollected culture supernatants were applied to zymography. The culture supernatants were mixed with a SDS polyacrylamide electrophoresis sample buffer solution (no-reducing agent; 50 mM Tris-HCl buffer, pH 6.5 containing 10% glycerol, 2% SDS, 0.1% bromophenol blue) and the mixture was incubated at 37° C. for 20 min., and applied to electrophoresis employing the following conditions: 20 mA, 4° C., 10% polyacrylamide gel containing 0.1% gelatin.

After electrophoresis, the gel was washed in a 2.5% Triton X-100 solution with gentle shaking for 1 hour, and then incubated in a gelatinase buffer solution (50 mM Tris-HCl, pH7.6 containing 10 mM $CaCl_2$, 0.15 M NaCl, and 0.02% $NaN_3$) with slow shaking at 37° C. for 24 hours. The buffer solution was discarded, and the gel was stained in 0.1% Coomassie Brilliant Blue R250 (dissolved in 50% methanol-10% acetic acid) for 1 hour, then was soaked in a decoloring solution (5% methanol- 7.5% acetic acid) and decolored. The results of the zymography was shown in FIG. 6.

Similarly to that in MT-MMP-1 cDNA-transfected COS-1, 64 kDa and 62 kDa bands corresponding to activate intermediate MMP-2 and active MMP-2, respectively, were newly expressed in MT-MMP-3 cDNA-transfected COS-1. Thus, the activation of pro MMP-2 was confirmed. On the other hand, in vector pSG5-transfected cells, only 68 kDa band of pro MMP-2 was detected, but the molecule size change accompanied with activation was not observed (FIG. 6A).

For COS-1 cells, the pro MMP-2 activation due to the expression plasmid was observed by cotransfection of pro MMP-2 expression plasmid (pSGGA). For HT1080 that constitutively expresses pro MMP-2, the pro MMP-2 activation accompanied with MT-MMP-3 expression was observed. The active form pro MMP-2 observed in this HT1080 has the same molecular size as the pro MMP-2 molecule induced by treating HT1080 cells with 100 µg/ml concanavalin A, and was specifically reacted with monoclonal anti-MMP-2 antibody. This activation was not observed in control cells transfected with the vector alone. On the other hand, for pro MMP-9, the change of the molecule size was not recognized as was in the control cells, and the activation was not recognized.

The activation of pro MMP-2 was suppressed in TIMP-1 and MT-MMP-3-cotransfected cells. It was suppressed in TIMP-2 and MT-MMP-3-cotransfected cells, too. The inhibitory degree in the TIMP-2 co-transfected cells was more significant than that in the TIMP-1, and this tendency was similar in MT-MMP-1 and MT-MMP-3 (FIG. 6B).

In an embodiment, the present invention relates to:

(A) a protein or a salt thereof, which (i) has an activity identical with or substantially equivalent to native MT-MMP, (ii) is a member of MMPs having the capability of activating pro MMP-2, (iii) is an activator for pro MMP-2, and (iv) is different from MT-MMP-1;

(B) the protein according to the above (A), wherein the protein has an activity or a primary structural, conformation identical with or substantially equivalent to that of MT-MMP-3 or a salt thereof; wherein the protein has activity substantially equivalent to MT-MMP-3 or its salt or has the primary structure conformation substantially equivalent thereto;

(C) the protein according to the above (A) or (B), wherein a C-terminal area of the protein has (i) an amino acid sequence from Ala$^{564}$ to Phe$^{587}$ in the sequence represented by SEQ ID NO: 2 in the Sequence Listing or (ii) an amino acid sequence substantially equivalent thereto;

(D) the protein according to any of the above (A) to (C), wherein the protein is MT-MMP-3 or a salt thereof which has (i) an amino acid sequence represented by SEQ ID NO: 2 in the Sequence Listing or (ii) an amino acid sequence equivalent thereto;

(E) the protein according to any of the above (A) to (D), wherein the protein is a product obtained by expressing a foreign DNA sequence in prokaryotes or eukaryotes;

(F) the protein according to any of the above (A) to (E), wherein the protein has (i) the amino acid sequence of SEQ ID NO: 2 in the Sequence Listing or (ii) the substantially same amino acid sequence;

(G) a partial peptide (or a peptide fragment) or its salt of the protein according to any of the above (A) to (F);

(H) a nucleic acid comprising a nucleotide sequence coding for the protein according to any of the above (A) to (F) or a partial peptide thereof;

(I) the nucleic acid according to the above (H) which is a DNA gene having a nucleotide sequence coding for MT-MMP-3 according to any of the above (B) to (D);

(J) the nucleic acid according to the above (H) or (I), having (i) an open reading frame region of the nucleotide sequence represented by SEQ ID NO: 1 in the Sequence Listing or (ii) a nucleotide sequence having an activity substantially equivalent thereto;

(K) a vector comprising the nucleic acid according to any of the above (H) to (J);

(L) a transformant wherein the nucleic acid according to any of the above (H) to (J) or the vector according to the above (K) is harbored; and (M) a process for producing the protein or its partial peptide according to any of the above (A) to (F), which comprises:

(i) culturing the transformant according to the above (L) in a nutrient medium capable of growing said transformant, and (ii) producing, as a recombinant species, the protein or its partial peptide according to any of the above (A) to (F), including MT-MMP-3 or a salt thereof.

Such a protein or a partial peptide thereof, and a nucleic acid are labeled and can be used for measurement and examination.

In another embodiment, the present invention relates to:

(a) a method for producing an antibody against a species selected from the group consisting of a protein or a salt thereof and a peptide thereof or a salt thereof according to any of claims 1 to 6, including MT-MMP-3 or a salt thereof, which comprises employing an antigen selected from the group consisting of said protein, said partial peptide and a salt thereof, and MT-MMP-3 or a salt thereof to raise the antibody thereagainst;

(b) an antibody against a species selected from the group consisting of a protein or a salt thereof according to any of claims 1 to 6, and MT-MMP-3 or a salt thereof, (c) the antibody according to the above (b), wherein the antibody is an anti-serum;

(d) the antibody according to the above (b), wherein the antibody is monoclonal;

(e) the antibody according to the above (b) or (d), which is a monoclonal antibody against MT-MMP-3 or a salt thereof;

(f) a method for producing the antibody according to above (d) or (e), which comprises (1) fusing an antibody-producing cell obtained from an immunized animal with an immortal cell, wherein said animal is immunized with a species selected from the group consisting of a protein or a salt thereof according to any of claims 1 to 6, a partial peptide of said protein or a salt thereof, and MT-MMP-3 or a salt thereof, and (2) selecting an immortal hybrid cell capable of an antibody against a species selected from the group consisting of a protein or a salt thereof according to any of claims 1 to 6, and MT-MMP-3 or a salt thereof;

(g) a method for detecting and/or measuring MT-MMP-3, which comprises using (A) a reagent selected from the group consisting of a protein or a salt thereof according to any of claims 1 to 6 and a partial peptide of said protein or a salt thereof, or (B) a reagent selected from the group consisting of the antibodies according to any of above (b) to (e);

(h) a labeled antibody against MT-MMP-3 for the method for detecting and/or measuring MT-MMP-3 (the detection and/or measurement of MT-MMP-3) according to above (g);

(i) a labeled protein or a salt thereof, for the method for detecting and/or measuring MT-MMP-3 (the detection and/or measurement of MT-MMP-3) according to above (g), wherein said labeled protein is a species selected from the group consisting of a protein or a salt thereof according to any of claims 1 to 6, and MT-MMP-3 or a salt thereof, or a labeled partial peptide of said protein or a salt thereof, for the method according to above (g);

(j) a labeled nucleic acid for detection and/or measurement of MT-MMP-3 expressing cells and/or tissues, wherein said nucleic acid is a species according to any of claims 8 to 10; and (k) the nucleic acid according to above (j), which is a probe for hybridization.

The protein or a salt thereof which (i) has an activity identical with or substantially equivalent to native MT-MMP that is a member of MMP capable of activating pro MMP-2, excluding MT-MMP-1, and (ii) is an activator for pro MMP-2 can be provided. Further, the nucleic acid encoding such proteins can be obtained. As a result, the diagnostic means useful for research & development regarding diagnosis and therapy of cancers including diagnosis of the presence or absence of tumor cells, estimation of malignancy of cancers or the like are provided. These are useful for the other medical and physiological applications. According to the present invention, there is provided: a novel matrix metalloproteinase specifically expressed on the cell surface layer of human tumors in particular; a DNA containing a nucleotide sequence coding for said matrix metalloproteinase; host cells transformed with said DNA; a process for producing the matrix metalloproteinase using the transformed host cells; a monoclonal antibody specifically binding with the matrix protease protein; and use of these proteins and antibodies. These enable us to investigate a matrix protease specifically expressed on the cell surface layer as a target of anti-metastatic drugs and as a marker for detection of cancers, judgment of malignancy, diagnosis of cancers, etc. In addition, the present invention is helpful for research of Alzheimer's diseases. Effective detection and therapeutic means is provided according to the present invention.

What is claimed is:

1. An isolated antibody which specifically binds to a matrix metalloproteinase (MMP) protein or a salt of said MMP protein, or a partial peptide of said MMP protein or a salt of said partial peptide, said matrix metalloproteinase protein or salt thereof comprising the following peptide fragments of SEQ ID No: 2: (a) $Gly^{109}$ to $Arg^{119}$, (b) $Pro^{171}$ to $Gly^{178}$, (c) $Thr^{229}$ to $Leu^{242}$ and (d) $Asp^{533}$ to $Val^{607}$, said matrix metalloproteinase protein having a maximum molecular weight of approximately 69kDa and is a pro MMP-2 activating factor, said partial peptide or salt thereof consisting of continuous antigenic amino acid residues of SEQ ID No: 2.

2. The antibody according to claim 1, wherein said matrix metalloproteinase protein or salt thereof further comprises the peptide fragment $Ala^{564}$ to $Phe^{587}$ of SEQ ID No: 2, said $Ala^{564}$ to $Phe^{587}$ fragment being located at or near the C-terminal of the protein.

3. The antibody according to claim 1, wherein said matrix metalloproteinase protein or salt thereof comprises the amino acid sequence as set forth in SEQ ID No: 2.

4. The antibody according to claim 1, wherein the antibody specifically binds against said partial peptide or salt thereof.

5. The antibody according to claim 1, wherein the antibody is polyclonal.

6. The antibody according to claim 1, wherein the antibody is monoclonal.

7. The antibody according to claim 1, wherein the antibody is labeled.

8. A method for producing an antibody which specifically binds to a matrix metalloproteinase (MMP) protein, a salt of said MMP protein, a partial peptide of said MMP protein, or a salt of said partial peptide, which comprises:

immunizing an animal with an antigen selected from the group consisting of a matrix metalloproteinase (MMP) protein, a salt of said MMP protein, a partial peptide of said MMP protein, and a salt of said partial peptide, said matrix metalloproteinase protein or salt thereof comprising the following peptide fragments of SEQ ID No: 2: (a) $Gly^{109}$ to $Arg^{119}$, (b) $Pro^{171}$ to $Gly^{178}$, (c) $Thr^{229}$ to $Leu^{242}$ and (d) $Asp^{533}$ to $Val^{607}$, said matrix metalloproteinase protein having a maximum molecular weight of approximately 69kDa and is a pro MMP-2 activating factor, said partial peptide or salt thereof comprising continuous antigenic amino acid residues of SEQ ID No: 2, and isolating an antibody which specifically binds to said antigen.

9. A method for producing an antibody which specifically binds to a matrix metalloproteinase (MMP) protein, a salt of said MMP protein, a partial peptide of said MMP protein, or a salt of said partial peptide, which comprises:

immunizing an animal with an antigen selected from the group consisting of a matrix metalloproteinase (MMP) protein, a salt of said MMP protein, a partial peptide of said MMP protein, and a salt of said partial peptide, said matrix metalloproteinase protein or salt thereof comprising the following peptide fragments of SEQ ID No: 2: (a) $Gly^{109}$ to $Arg^{119}$, (b) $Pro^{171}$ to $Gly^{178}$, (c) $Thr^{229}$ to $Leu^{242}$ and (d) $Asp^{533}$ to $Val^{607}$, said matrix metalloproteinase protein having a maximum molecular weight of approximately 69kDa and is a pro MMP-2 activating factor, said partial peptide or salt thereof comprising continuous antigenic amino acid residues of SEQ ID No: 2, to obtain an antibody-producing cell which produces an antibody which specifically binds to said antigen, fusing said antibody-producing cell with an immortal cell, and selecting an immortal hybrid cell which produces a monoclonal antibody which specifically binds to said antigen.

10. A method for detecting and/or measuring a matrix metalloproteinase protein or salt thereof, which comprises:

contacting a test sample with an antibody which specifically binds to a matrix metalloproteinase (MMP) protein or a salt of said MMP protein, or a partial peptide of said MMP protein or a salt of said partial peptide, said matrix metalloproteinase protein or salt thereof comprising the following peptide fragments of SEQ ID No: 2: (a) Gly$^{109}$ to Arg$^{119}$, (b) Pro$^{171}$ to Gly$^{178}$, (c) Thr$^{229}$ to Leu$^{242}$ and (d) Asp$^{533}$ to Val$^{607}$, said matrix metalloproteinase protein having a maximum molecular weight of approximately 69kDa and is a pro MMP-2 activating factor, said partial peptide or salt thereof comprising continuous antigenic amino acid residues of SEQ ID No: 2, and detecting and/or measuring the matrix metalloproteinase protein or salt thereof bound to the antibody.

11. The method according to claim 10, wherein the antibody is labelled.

12. The antibody according to claim 1, wherein said partial peptide or salt thereof consists of SEQ ID NO: 5, 6, 7 or 8.

13. The antibody according to claim 1, which is not crossreactive with any one of the matrix metalloproteinase (MMP) protein selected from the group consisting of MMP-1, MMP-2, MMP-3, MMP-7, MMP-8 and MMP-9.

14. The antibody according to claim 1, wherein said partial peptide or salt thereof consists of at least 8 continuous antigenic amino acid residues of SEQ ID No: 2.

* * * * *

UNITED STATES PATENT AND TRADEMARK OFFICE
CERTIFICATE OF CORRECTION

PATENT NO. : 6,780,412 B2
DATED : August 24, 2004
INVENTOR(S) : Motoharu Seiki et al.

It is certified that error appears in the above-identified patent and that said Letters Patent is hereby corrected as shown below:

<u>Title page,</u>
Item [73], Assignee, "Fuji Yakuhin Kogyo Kasushiki Kaisha" should read
-- Daiichi Fine Chemical Co., Ltd. --

Signed and Sealed this

Fourteenth Day of June, 2005

JON W. DUDAS
*Director of the United States Patent and Trademark Office*

UNITED STATES PATENT AND TRADEMARK OFFICE
CERTIFICATE OF CORRECTION

PATENT NO.    : 6,780,412 B2
DATED         : August 24, 2004
INVENTOR(S)   : Motoharu Seiki et al.

It is certified that error appears in the above-identified patent and that said Letters Patent is hereby corrected as shown below:

<u>Title page,</u>
Item [73], Assignee, "Fuji Yakuhin Kogyo Kabushiki Kaisha" should read
-- Daiichi Fine Chemical Co., Ltd. --

This certificate supersedes Certificate of Correction issued June 14, 2005.

Signed and Sealed this

Twenty-sixth Day of July, 2005

JON W. DUDAS
*Director of the United States Patent and Trademark Office*